(12) United States Patent
Vargeese et al.

(10) Patent No.: US 7,655,790 B2
(45) Date of Patent: *Feb. 2, 2010

(54) DEPROTECTION AND PURIFICATION OF OLIGONUCLEOTIDES AND THEIR DERIVATIVES

(75) Inventors: Chandra Vargeese, Broomfield, CO (US); Christopher Shaffer, Longmont, CO (US); Keith Bowman, Longmont, CO (US)

(73) Assignee: Sirna Therapeutics, Inc., San Francisco, CA (US)

(*) Notice: Subject to any disclaimer, the term of this patent is extended or adjusted under 35 U.S.C. 154(b) by 412 days.

This patent is subject to a terminal disclaimer.

(21) Appl. No.: 11/036,694

(22) Filed: Jan. 12, 2005

(65) Prior Publication Data
US 2005/0215777 A1   Sep. 29, 2005

Related U.S. Application Data

(63) Continuation-in-part of application No. PCT/US03/21775, filed on Jul. 14, 2003, which is a continuation-in-part of application No. 10/194,875, filed on Jul. 12, 2002, now Pat. No. 6,989,442.

(51) Int. Cl.
*C07H 21/04* (2006.01)
(52) U.S. Cl. .................... 536/25.33; 536/25.34
(58) Field of Classification Search .............. 536/25.31, 536/25.33, 25.34
See application file for complete search history.

(56) References Cited

U.S. PATENT DOCUMENTS

| | | | |
|---|---|---|---|
| 4,987,071 A | 1/1991 | Cech et al. | |
| 5,334,711 A | 8/1994 | Sproat et al. | |
| 5,475,096 A | 12/1995 | Gold et al. | |
| 5,552,539 A | 9/1996 | Duplaa et al. | |
| 5,567,588 A | 10/1996 | Gold et al. | |
| 5,625,047 A | 4/1997 | Been et al. | |
| 5,627,053 A | 5/1997 | Usman et al. | |
| 5,631,359 A | 5/1997 | Chowrira et al. | |
| 5,631,360 A | 5/1997 | Usman et al. | |
| 5,672,695 A | 9/1997 | Eckstein et al. | |
| 5,686,599 A * | 11/1997 | Tracz .................... | 536/25.31 |
| 5,716,824 A | 2/1998 | Beigelman et al. | |
| 5,804,683 A | 9/1998 | Usman et al. | |
| 5,831,071 A | 11/1998 | Usman et al. | |
| 5,977,343 A | 11/1999 | Tracz | |
| 5,989,912 A | 11/1999 | Arrow et al. | |
| 5,998,203 A | 12/1999 | Matulic-Adamic et al. | |
| 6,001,311 A | 12/1999 | Brennan et al. | |
| 6,117,657 A | 9/2000 | Usman et al. | |
| 6,353,098 B1 | 3/2002 | Usman et al. | |
| 6,362,323 B1 | 3/2002 | Usman et al. | |
| 6,437,117 B1 | 8/2002 | Usman et al. | |
| 6,469,158 B1 | 10/2002 | Usman et al. | |

FOREIGN PATENT DOCUMENTS

| | | |
|---|---|---|
| EP | 0360257 | 3/1990 |
| WO | 91/03162 | 3/1991 |
| WO | 92/07065 | 4/1992 |
| WO | 93/15187 | 8/1993 |
| WO | 93/23569 | 11/1993 |
| WO | 95/23225 | 8/1995 |
| WO | 97/26270 | 7/1997 |
| WO | 98/13526 | 4/1998 |
| WO | 98/28317 | 7/1998 |
| WO | 98/58057 | 12/1998 |
| WO | 98/58058 | 12/1998 |
| WO | 99/07409 | 2/1999 |
| WO | 99/16871 | 4/1999 |
| WO | 99/32619 | 7/1999 |
| WO | 99/54459 | 10/1999 |
| WO | 99/55857 | 11/1999 |
| WO | 00/01846 | 1/2000 |
| WO | 00/44895 | 8/2000 |
| WO | 00/44914 | 8/2000 |
| WO | 01/29058 | 4/2001 |
| WO | 01/36646 | 5/2001 |
| WO | 2004/07748 | 1/2004 |

OTHER PUBLICATIONS

Wincott et al, Nucleic Acid Research, 1995, 23(14), 2677-2684.*
U.S. Appl. No. 09/406,643, filed Dec. 27, 1999, Ludwig et al.
U.S. Appl. No. 10/190,359, filed Jul. 3, 2002, Vargeese et al.
U.S. Appl. No. 10/194,875, filed Jul. 12, 2002, Vargeese et al.
U.S. Appl. No. 10/444,853, filed May 23, 2003, McSwiggen et al.
U.S. Appl. No. 60/082,404, filed Apr. 20, 1998, Thompson et al.
U.S. Appl. No. 60/101,174, filed Sep. 21, 1998, Hartmann et al.
Allshire, "RNAi and Heterochromatin—A Hushed-up Affair," *Science* 297:1818-1819 (2002).
Bartel and Szostak, "Isolation of New Ribozymes from a Large Pool of Random Sequences," *Science* 261:1411-1418(1993).
Bass, "The short answer," *Nature* 411:428-429 (2001).
Beaucage and Iyer, "The Functionalization of Oligonucleotides Via Phosphoramidite Derivatives," *Tetrahedron* 49:1925-1963 (1993).
Beaudry and Joyce, "Directed Evolution of an RNA Enzyme," *Science* 257:635-641 (1992).
Beaudry et al., "In Vitro Selection of a Novel Nuclease-Resistant RNA Phosphodiesterase," *Chemistry & Biology* 7:323-334 (2000).
Beigelman et al., "Synthesis of 2'-modified nucleotides and their incorporation into hammerhead ribozymes," *Nucleic Acids Research* 23(21):4434-4442 (1995).

(Continued)

*Primary Examiner*—Shaojia Anna Jiang
*Assistant Examiner*—Ganapathy Krishnan

(57) ABSTRACT

Method for synthesis, deprotection, and/or purification of nucleic acid molecules, such as oligonucleotides comprising one or more ribonucleotides. Such nucleic acid molecules include siRNA, dsRNA, ribozymes, antisense, and aptamers.

24 Claims, 8 Drawing Sheets

OTHER PUBLICATIONS

Beigelman et al., "Chemical Modification of Hammerhead Ribozymes," *The Journal of Biological Chemistry* 270:25702-25708 (1995).

Bellon et al., "Amino-Linked Ribozymes: Post-Synthetic Conjugation of Half-Ribozymes," *Nucleosides & Nucleotides* 16:951-954 (1997).

Bellon et al., "Post-synthetically Ligated Ribozymes: An Alternative Approach to Iterative Solid Phase Synthesis," *Bioconiugate Chem.* 8:204-212 (1997).

Bernstein et al., "Role for a Bidentate Ribonuclease in the Initiation Step of RNA Interference," *Nature* 409:363-366 (2001).

Breaker and Joyce, "Inventing and improving ribozyme function: rational design versus iterative selection methods," *TIBTECH* 12:268-275 (1994).

Breaker, "Are engineered proteins getting competition from RNA?" *Current Opinion in Biotechnology* 7:442-448 (1996).

Brennan et al:, "Two-Dimensional Parallel Array Technology as a New Approach to Automated Combinatorial Solid-Phase Organic Synthesis," *Biotechnology and Bioengineering (Combinatorial Chemistry)* 61:33-45 (1998).

Brody and Gold, "Aptamers as therapeutic and diagnostic agents," *Reviews in Molecular Biotechnology* 74:5-13 (2000).

Brown et al., "The Preparation of Cyclic 2':3'-Phosphates of Adenosine, Cytidine, and Uridine," *Nucleotides. Part XII* 2530:2708-2714 (1952).

Burgin et al., "Chemically Modified Hammerhead Ribozymes with Improved Catalytic Rates," *Biochemistry* 35:14090-14097 (1996) (vol. No. mistakenly listed as 6).

Burlina et al., "Chemical Engineering of RNase Resistant and Catalytically Active Hammerhead Ribozymes," *Bioorganic & Medicinal Chemistry* 5:1999-2010 (1997).

Caruthers et al., "Chemical Synthesis of Deoxyoligonucleotides and Deoxyoligonucleotide Analogs," *Methods in Enzymology* 211:3-19 (1992).

Cech, "Ribozymes and Their Medical Implications," *JAMA* 260:3030-3034 (1988).

Chaix et al., "Solid Phase Synthesis of the 5'-Half of the Initiator t-RNA from *B.subtilis*," *Nucleic Acids Research* 17:7381-7393 (1989).

Christoffersen and Marr, "Riobozymes as Human Therapeutic Agents," *J. Med. Chem.* 38:2023-2037 (1995) (also referred to as Christofferson and Marr).

Cook et al., "Characterization of HIV-1 REV Protein: Binding Stoichiometry and Minimal RNA Substrate," *Nucleic Acids Research* 19:1577-1583 (1991).

Dreyfus, "Restriction Ribozymes?" *Einstein Quarterly Journal of Biology and Medicine*. 6:92-93 (1988).

Duval-Valentin, "Specific inhibition of transcription by triple helix-forming oligonucleotides," *Proc. Natl. Acad. Sci. USA* 89:504-508 (1992).

Eamshaw et al., "Modified Oligoribonucleotides as Site-Specific Probes of RNA Structure and Function," *Biopolymers* 48:39-55 (1998).

Egholm et al., "PNA hybridizes to complementary oligonucleotides obeying the Watson-Crick hydrogen-bonding rules," *Nature* 365:566-568 (1993).

Elbashir et al., "Duplexes of 21-nucleotide RNAs mediate RNA interference in cultured mammalian cells," *Nature* 411:494-498 (2001).

Elbashir et al., "Functional Anatomy of siRNAs for Mediating Efficient RNAi in *Drosophila Melanogaster* Embryo Lysate," *The EMBO Journal* 20:6877-6888 (2001).

Elbashir et al., "RNA Interference is Mediated by 21- and 22-Nucleotide RNAs," *Genes and Development* 15:188-200 (2001).

Fire et al., "Potent and Specific Genetic Interference by Double-Stranded RNA in *Caenorhabditis Elegans*," *Nature* 391:806-811(1998).

Fire, "RNA-triggered Gene Silencing," *TIG* 15:358-363(1999).

Forster and Altman, "External Guide Sequences for an RNA Enzyme," *Science* 249:783-786 (1990).

Francklyn and Schimmel, "Aminoacylation of RNA Minihelices with Alanine," *Nature* 337:478-481 (1989).

Gasparutto et al., "Chemical synthesis of a biologically active natural tRNA with its minor bases," *Nucleic Acids Research* 20(19):5159-5166 (1992).

Gold et al., "Diversity of Oligonucleotide Functions," *Annu. Rev. Biochem.* 64:763-797 (1995).

Gold, "Posttranscriptional Regulatory Mechanisms in *Escherichia coli*," *Ann. Rev.Biochem.* 57:199-233 (1988).

Guerrier-Takada et al., "The RNA Moiety of Ribonuclease P Is the Catalytic Subunit of the Enzyme," *Cell* 35:849-857 (1983).

Guo and Collins, "Efficent *trans*-cleavage of a stem-loop RNA substrate by a ribozyme derived from *Neurospora* VS RNA," *Embo J.* 14:368-376 (1995).

Hall et al., "Establishment and Maintenance of a Heterochromatin Domain," *Science*297:2232-2237 (2002).

Hammond et al., "An RNA-Directed Nuclease Mediates Post-Transcriptional Gene Silencing in *Drosophila* Cells," *Nature* 404:293-296 (2000).

Hampel and Tritz, "RNA Catalytic Properties of the Minimum (-)sTRSV Sequence," *Biochemistry* 28:4929-4933 (1989).

Hampel et al., "'Hairpin' Catalytic RNA Model: Evidence for Helices and Sequence Requirement for Substrate RNA," *Nucleic Acids Research* 18:299-304 (1990).

Haseloff and Gerlach, "Simple RNA Enzymes with New and Highly Specific Endoribonuclease Activities," *Nature* 334:585-591 (1988).

Hermann and Patel, "Adaptive Recognition by Nucleic Acid Aptamers," *Science* 287:820-825 (2000).

Hogrefe et al., "Effect of excess water on the desilylation of oligoribonucleotides using tetrabutylammonium fluoride," *Nucleic Acids Research* 21:4739-4741 (1993).

Hunziker et al., "Nucleic Acid Analogues: Synthesis and Properties, in Modern Synthetic Methods," *VCH*, 331-417 (1995) [sometimes mistakenly cited as Leumann].

Hutvagner and Zamore, "A MicroRNA in a Multiple-Turnover RNAi Enzyme Complex," *Science* 297:2056-2060 (2002).

Hutvagner et al., "A Cellular Function for the RNA-Interference Enzyme Dicer in the Maturation of the *let*-7 Small Temporal RNA," *Science* 293:834-838 (2001).

Ishizaka et al., "Isolation of Active Ribozymes from an RNA Pool of Random Sequences Using an Anchored Substrate RNA," *Biochemical and Biophysical Research Communication* 214(2):403-409 (1995).

Jayasena, "Aptamers: An Emerging Class of Molecules that Rival Antibodies in Diagnostics," *Clinical Chemistry* 45:1628-1650 (1999).

Jeffries and Symons, "A Catalytic 13-mer Ribozyme," *Nucleic Acids Research* 17:1371-1377 (1989) (also referred to as Jefferies).

Jenuwein, "An RNA-Guided Pathway for the Epigenome," *Science* 297:2215-2218 (2002).

Johnson and Benkovic, "Analysis of Protein Function by Mutagenesis," *The Enzymes* 19:159-211 (1990).

Joyce et al., "Amplification, mutation and selection of catalytic RNA," *Gene* 82:83-87 (1989).

Joyce, "Directed Molecular Evolution," *Scientific American* 267:90-97 (1992).

Karaoglu and Thu rlow, "A Chemical Interference Study on the Interaction of Ribosomal Protein L11 from *Escherichia coli* with RNA Molecules Containing its Binding Site from 23S rRNA," *Nucleic Acids Research* 19:5293-5300 (1991).

Karpeisky et al, "Highly Efficient Synthesis of 2'-O-Amino Nucleosides And Their Incorporation in Hammerhead Ribozymes," *Tetrahedron Letters* 39:1131-1134 (1998).

Kim and Cech, "Three-dimensional model of the active site of the self-splicing rRNA precursor of *Tetrahymena*," *Proc. Natl. Acad. Sci. USA* 84:8788-8792 (1987).

Kore, et al., "Sequence specificity of the hammerhead ribozyme revisistsed; the NIH rule," *Nucleic Acids Research*, 26(18):4116-4120 (1998).

Kumar and Ellington, "Artificial evolution and natural ribozymes," *FASEB J.* 9:1183-1195 (1995).

Kusser, "Chemically modified nucleic acid aptamers for in vitro selections: evolving evolution," *Reviews in Molecular Biotechnology* 74:27-38 (2000).

Limbach et al., "Summary: the modified nucleosides of RNA," *Nucleic Acids Research* 22(12):2183-2196 (1994).

Long and Uhlenbeck, "Kinetic characterization of intramolecular and intermolecular hammerhead RNAs with stem II deletions," *Proc. Natl. Acad. Sci. USA* 91:6977-6981 (1994).

Martinez et al., "Single-Stranded Antisense siRNAs Guide Target RNA Cleavage in RNAi," *Cell* 110:563-574 (2002).

McManus et al., "Gene Silencing Using Micro-RNA Designed Hairpins," *RNA* 8:842-850 (2002).

Mesmaeker et al, "Novel Backbone Replacements for Oligonucleotides," *American Chemical Society*, pp. 24-39 (1994).

Moore and Sharp, "Site-Specific Modification of Pre-mRNA: The 2'-Hydroxyl Groups at the Splice Sites," *Science* 256:992-996 (1992).

Mukhopadhyay et al., "Antisense Regulation of Oncogenes in Human Cancer," *Critical Reviews in Oncogenesis* 7:151-190 (1996).

Nakamaye and Eckstein, "AUA-Cleaving Hammerhead Ribozymes: Attempted Selection for Improved Cleavage," *Biochemistry* 33:1271-1277 (1994).

Nykanen et al., "ATP Requirements and Small Interfering RNA Structure in the RNA Interference Pathway," *Cell* 107:309-321 (2001).

Orgel, "Selection in vitro," *Proc. R. Soc. London B*. 205:435-442 (1979).

Perreault et al., "Mixed Deoxyribo- and Ribo-Oligonucleotides with Catalytic Activity," *Nature* 344:565-567 (1990) (often mistakenly listed as Perrault).

Perrotta and Been, "Cleavage of Oligoribonucleotides by a Ribozyme Derived from the Hepatitis δ Virus RNA Sequence," *Biochemistry* 31:16-21 (1992).

Pieken et al., "Kinetic Characterization of Ribonuclease-Resistant 2'-Modified Hammerhead Ribozymes," *Science* 253:314-317(1991).

Reddy et al., "Fast Cleavage and Deprotection of Oligonucleotides," *Tetrahedron Letters* 35:4311-4314 (1994).

Reddy et al., "Methylamine Deprotection Provides Increased Yield of Oligoribonucleotides," *Tetrahedron Letters* 36:8929-8932 (1995).

Reinhart and Bartel, "Small RNAs Correspond to Centromer Heterochromatic Repeats," *Science* 297:1831 (2002).

Reinhart et al., "MicroRNAs in Plants," *Genes & Development* 16:1616-1626 (2002).

Rossi et al., "Ribozymes as Anti-HIV-1 Therapeutic Agents: Principles, Applications, and Problems," *Aids Research and Human Retroviruses* 8:183-189 (1992).

Santoro and Joyce, "A general purpose RNA-cleaving DNA enzyme," *Proc. Natl. Acad. Sci. USA* 94:4262-4266 (1997).

Saville and Collins, "A Site-Specific Self-Cleavage Reaction Performed by a Novel RNA in *Neurospora* mitochondria," *Cell* 61:685-696 (1990).

Saville and Collins, "RNA-Mediated Ligation of Self-Cleavage Products of a *Neurospora* Mitochondrial Plasmid Transcript," *Proc. Natl. Acad. Sci. USA* 88:8826-8830 (1991).

Scaringe et al., "Chemical synthesis of biologically active oligoribonucleotides using β-cyanoethyl protected ribonucleoside phosphoramidites," *Nucl Acids Res*. 18:5433-5441 (1990).

SchWarz et al., "Evidence that siRNAs Function as Guides, Not Primers, in the *Drosophila* and Human RNAi Pathways," *Molecular Cell* 10:537-548 (2002).

Shabarova et al., "Chemical ligation of DNA: The first non-enyzmatic assembly of a biologically active gene," *Nucleic Acids Research* 19:4247-4251 (1991).

Sproat et al., "An Efficient Method for the Isolation and Purification of Oligoribonucleotides," *Nucleosides & Nucleotides* 14:255-273 (1995).

Stein and Cheng, "Antisense Oligonucleotides as Therapeutic Agents—Is the Bullet Really Magical?" *Science* 261:1004-1288 (1993).

Sullenger et al., "Overexpression of TAR Sequences Renders Cells Resistant to Human Immunodeficiency Virus Replication," *Cell* 63:601-608 (1990).

Sun, "Technology evaluation: SELEX, Giliad Sciences Inc," *Current Opinion in Molecular Therapeutics* 2:100-105 (2000).

Szostak, "In Vitro Genes," *TIBS* 17:89-93 (1993).

Tang et al., "Examination of the catalytic fitness of the hammerhead ribozyme by in vitro selection," *RNA* 3:914-925 (1997).

Torrence et al., "Targeting RNA for degradation with a (2'-5') oligoadenylate-antisense chimera," *Proc. Natl. Acad. Sci. USA* 90:1300-1304 (1993).

Tsai et al., "In vitro selection of an RNA epitope immunologically cross-reactive with a peptide," *Proc. Natl. Acad. Sci. USA* 89:8864-8868 (1992).

Uhlenbeck, "A Small Catalytic Oligoribonucleotide," *Nature* 328:596-600 (1987) (this is listed as Nature 327 in the various specifications, but it is actually 328).

Uhlmann and Peyman, "Antisense Oligonucleotides: A New Therapeutic Principle," *Chemical Reviews* 90:544-584 (1990).

Usman and Cedergren, "Exploiting the chemical synthesis of RNA," *TIBS* 17:334-339 (1992).

Usman and McSwiggen, "Ch. 30—Catalytic RNA (Ribozymes) as Drugs," *Annual Reports In Medicinal Chemistry* 30:285-294 (1995).

Usman et al., "Automated Chemical Synthesis of Long Oligoribonucleotides Using 2'-O-Silylated Ribonucleoside 3'-O-Phosphoramidites on a Controlled-Pore Glass Support: Synthesis of a 43-Nucleotide Sequence Similar to the 3'-Half Molecule of an *Escherichia coli* Formylmethoionine tRNA," *J. Am. Chem. Soc*. 109:7845-7854 (1987).

Usman et al., "Chemical modification of hammerhead ribozymes: activity and nuclease resistance," *Nucleic Acids Symposium Series* 31:163-164 (1994).

Usman et al., "Hammerhead ribozyme engineering," *Current Opinion in Structural Biology* 1:527-533(1996).

Vaish et al., "Isolation of Hammerhead Ribozymes with Altered Core Sequences by in Vitro Selection," *Biochemistry* 36:6495-6501 (1997).

Vargeese et al., "Efficient Activation of Nucleoside Phosphoramidites with 4,5-dicyanoimidazole During Oligonucleotide Synthesis," *Nucleic Acids Research* 26:1046-1050 (1998).

Verma and Eckstein, "Modified Oligonucleotides: Synthesis and Strategy for Users," *Annu. Rev. Biochem*. 67:99-134 (1998).

Volpe et al., "Regulation of Heterochromatic Silencing and Histone H3 Lysine-9 Methylation by RNAi," *Science* 297:1833-1837 (2002).

Warashina, et al., Extremely High and Specific Activity of DNA Enzymes in Cells with a Philadelphia Chromosome, *Chemistry &Biology*, 6(4):237-250 (1999).

Westman et al., "Removal of *t*-butyldimethylsilyl Protection in RNA-synthesis. Triethylamine trihydrofluoride (TEA, 3HR) is a More Reliable Alternative to Tetrabutylammonium Fluoride (TBAF)" *Nucleic Acids Research* 22:2430-2431 (1994).

Wianny and Zernicka-Goetz et al., "Specific Interference with Gene Function by Double-Stranded RNA in Early Mouse Development," *Nature Cell Biology* 2:70-75 (2000).

Wincott et al., "Synthesis, deprotection, analysis and purification of RNA and ribozymes," *Nucleic Acids Research* 23(14):2677-2684 (1995).

Wincott et al., "A Practical Method for the Production of RNA and Ribozymes," *Methods in Molecular Biology* 74:59-69 (1997).

Wu-Pong, "Oligonucleotides: Opportunities for Drug Therapy and Research," *BioPharm* pp. 20-33 (1994).

Zaug et al., "The *Tetrahymena* Ribozyme Acts Like an RNA Restriction Endonuclease," *Nature* 324:429-433 (1986).

\* cited by examiner

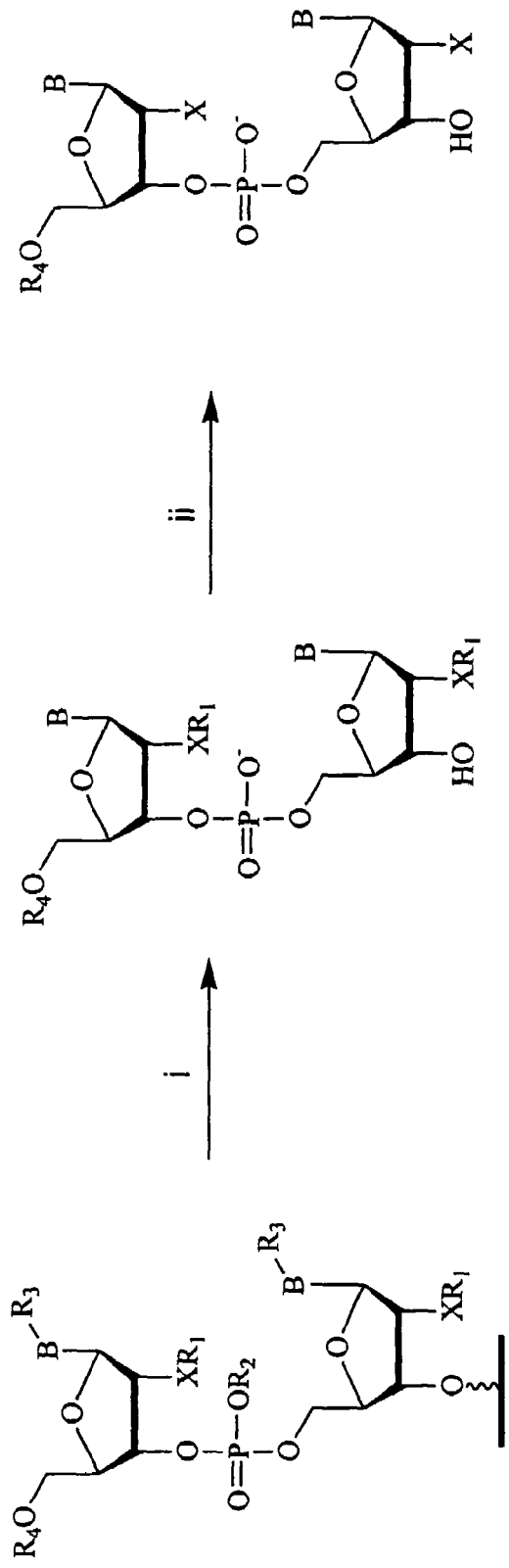
Figure 1: One Pot Deprotection of RNA containing molecules

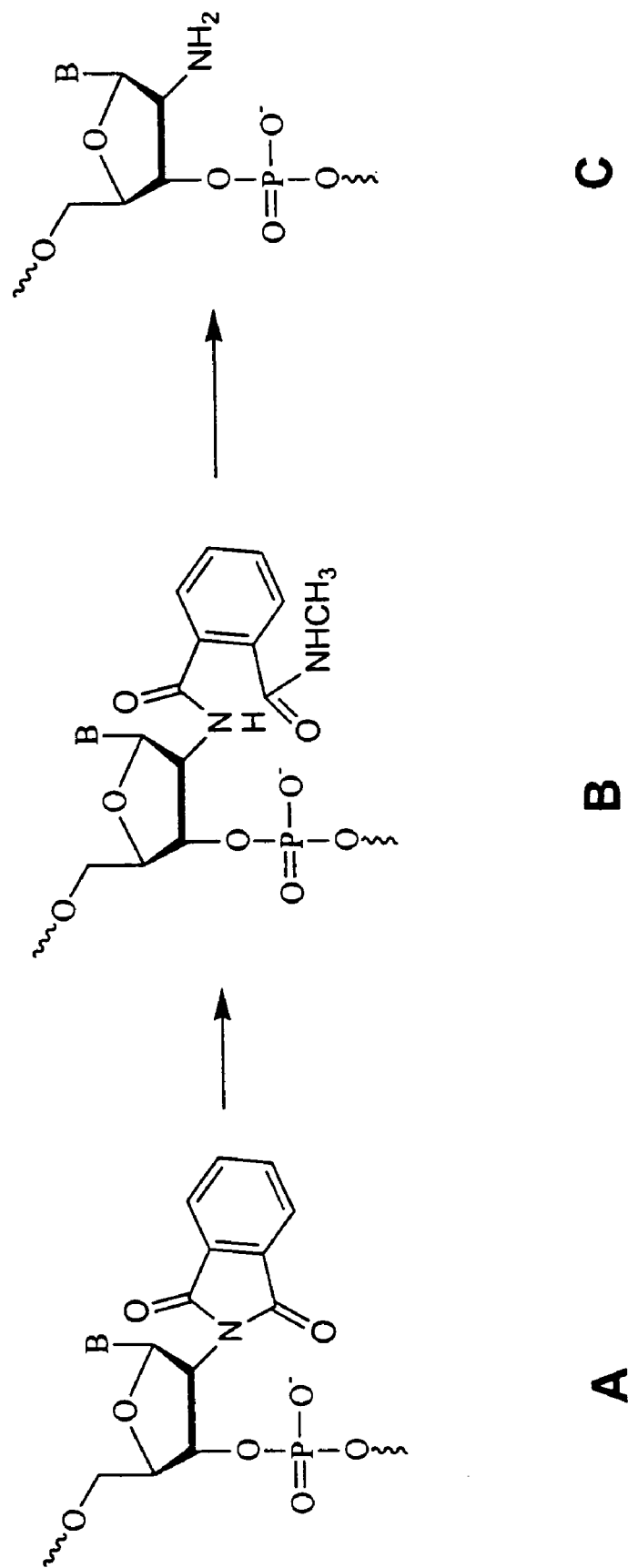
Figure 2: Incomplete Phthaloyl Deprotection

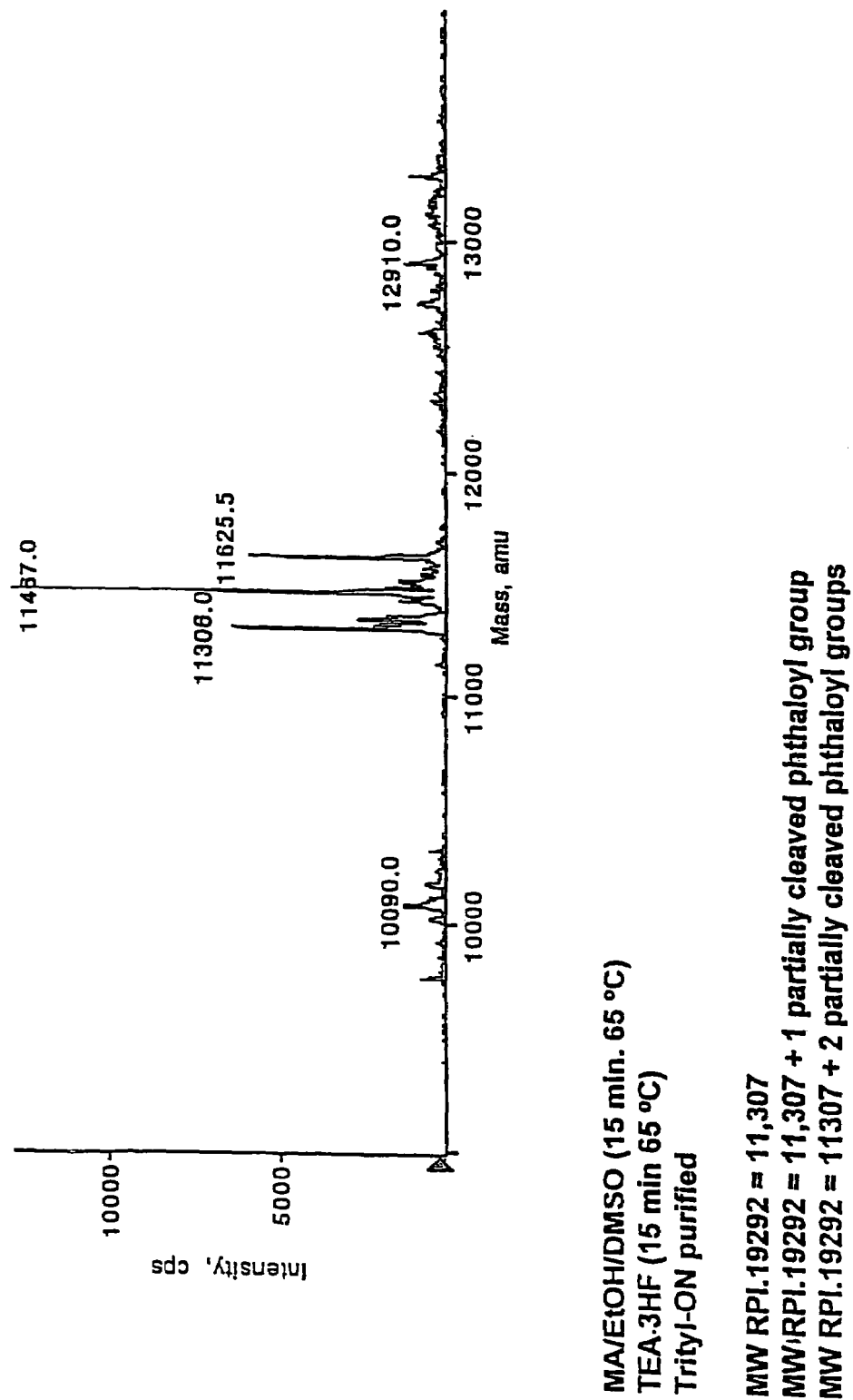
Figure 3A: MS Analysis of RPI.19292 After Anhydrous Deprotection

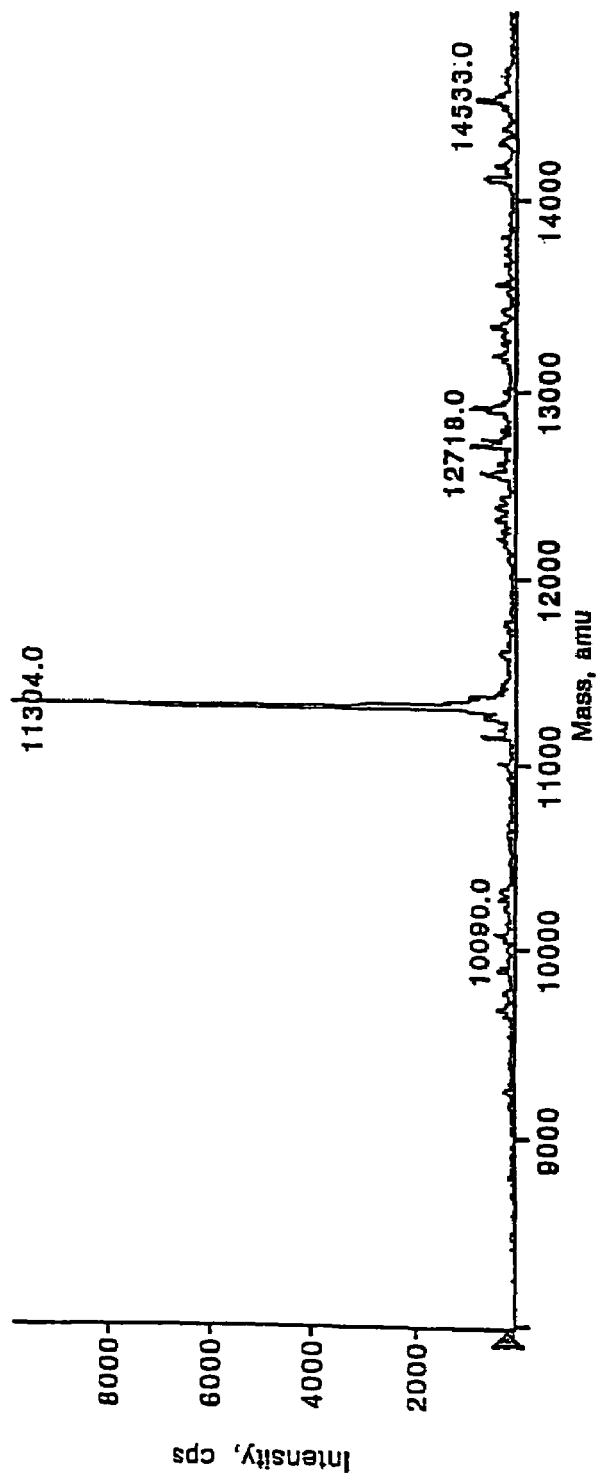
Figure 3B: MS Analysis of RPI.19292 After Aqueous Deprotection

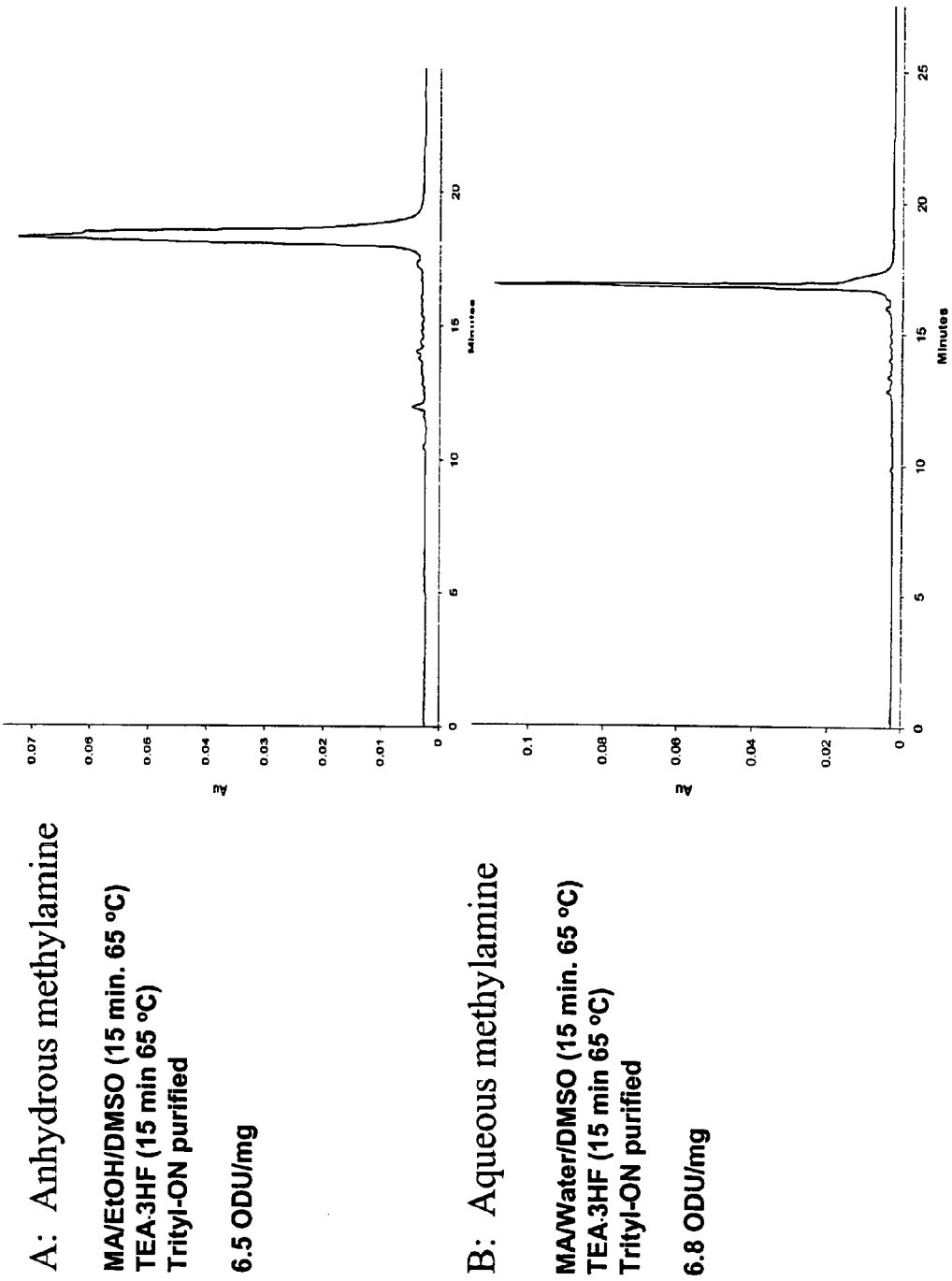

Figure 5
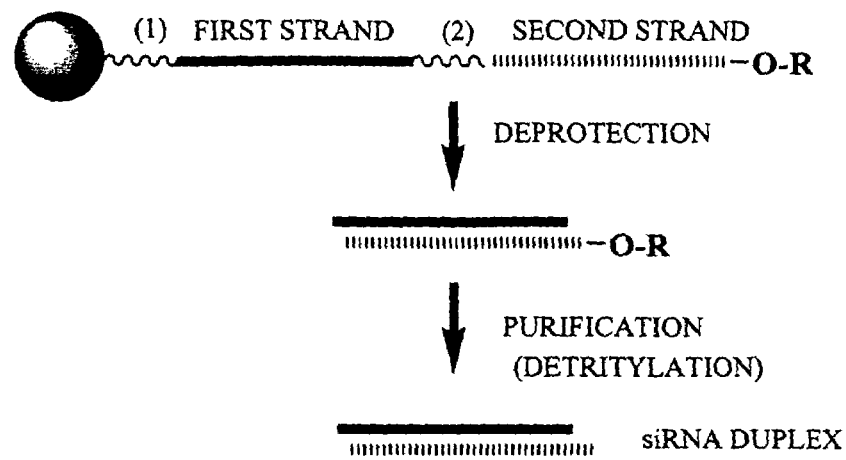
 = SOLID SUPPORT
R = TERMINAL PROTECTING GROUP
FOR EXAMPLE:
DIMETHOXYTRITYL (DMT)
(1) ∿∿∿ = CLEAVABLE LINKER
(FOR EXAMPLE: NUCLEOTIDE SUCCINATE OR
INVERTED DEOXYABASIC SUCCINATE)
(2) ∿∿∿ = CLEAVABLE LINKER
(FOR EXAMPLE: NUCLEOTIDE SUCCINATE OR
INVERTED DEOXYABASIC SUCCINATE)
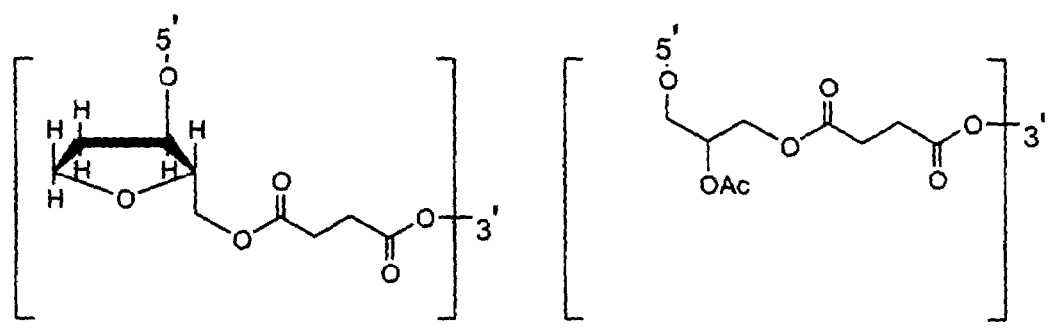
INVERTED DEOXYABASIC SUCCINATE LINKAGE
GLYCERYL SUCCINATE LINKAGE

SEQUENCE LISTING

```
<160> NUMBER OF SEQ ID NOS: 1

<210> SEQ ID NO 1
<211> LENGTH: 33
<212> TYPE: RNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(6)
<223> OTHER INFORMATION: 2'-O methyl
<220> FEATURE:
<221> NAME/KEY: misc_feature
<222> LOCATION: (1)..(4)
<223> OTHER INFORMATION: phosphorothioate internucleotide linkage
<220> FEATURE:
<221> NAME/KEY: misc_feature
<222> LOCATION: (8)..(14)
<223> OTHER INFORMATION: 2'-O methyl
<220> FEATURE:
<221> NAME/KEY: misc_feature
<222> LOCATION: (16)..(16)
<223> OTHER INFORMATION: 2'-deoxy-2'-amino cytidine
<220> FEATURE:
<221> NAME/KEY: misc_feature
<222> LOCATION: (18)..(18)
<223> OTHER INFORMATION: 2'-O methyl
<220> FEATURE:
<221> NAME/KEY: misc_feature
<222> LOCATION: (20)..(20)
<223> OTHER INFORMATION: 2'-O methyl
<220> FEATURE:
<221> NAME/KEY: misc_feature
<222> LOCATION: (22)..(22)
<223> OTHER INFORMATION: 2'-O methyl
<220> FEATURE:
<221> NAME/KEY: misc_feature
<222> LOCATION: (25)..(25)
<223> OTHER INFORMATION: 2'-O methyl
<220> FEATURE:
<221> NAME/KEY: misc_feature
<222> LOCATION: (26)..(26)
<223> OTHER INFORMATION: 2'-deoxy-2'-amino cytidine
<220> FEATURE:
<221> NAME/KEY: misc_feature
<222> LOCATION: (27)..(33)
<223> OTHER INFORMATION: 2'-O methyl
<220> FEATURE:
<221> NAME/KEY: misc_feature
<222> LOCATION: (33)..(33)
<223> OTHER INFORMATION: inverted deoxy abasic moiety

<400> SEQUENCE: 1
gcaguggccg aaaggcgagu gaggucuagc uca                          33
```

DEPROTECTION AND PURIFICATION OF OLIGONUCLEOTIDES AND THEIR DERIVATIVES

This application is a Continuation-in-part of International Application No. PCT/US03/21775 filed Jul. 14, 2003, which is a Continuation-in-part of U.S. patent application Ser. No. 10/194,875, filed Jul. 12, 2002. These applications are hereby incorporated by reference herein in its entirety, including the drawings.

SEQUENCE LISTING

The sequence listing submitted via EFS, in compliance with 37 CFR §1.52(e)(5), is incorporated herein by reference. The sequence listing text file submitted via EFS contains the file "SequenceListing63USCIP," created on Oct. 14, 2009, which is 1,931 bytes in size.

BACKGROUND OF THE INVENTION

This invention relates to the synthesis, deprotection, and purification of molecules comprising one or more ribonucleotides.

The following discussion relates to the synthesis, deprotection, and purification of oligonucleotides containing one or more ribonucleotides. The discussion is not meant to be complete and is provided only for understanding the invention that follows. The summary is not an admission that any of the work described below is prior art to the claimed invention.

Research in the many roles of ribonucleic acids has, in the past, been hindered by limited means of producing such biologically relevant molecules (Cech, 1992, *Nucleic Acids Research*, 17, 7381-7393; Francklyn and Schimmel, 1989, *Nature*, 337, 478-481; Cook et al., 1991, *Nucleic Acids Research*, 19, 1577-1583; Gold, 1988, *Annu. Rev. Biochemistry*, 57, 199-233). Although enzymatic methods existed, protocols that allowed one to probe structure function relationships were limited. Only uniform post-synthetic chemical modification (Karaoglu and Thurlow, 1991, *Nucleic Acids Research*, 19, 5293-5300) or site directed mutagenesis (Johnson and Benkovic, 1990, *The Enzymes*, Vol. 19, Sigman and Boyer, eds., 159-211) were available. In the latter case, researchers were limited to usage of natural bases. Fortunately, adaptation of the phosphoramidite protocol for DNA synthesis to RNA synthesis has greatly accelerated our understanding of RNA. Site-specific introduction of modified nucleotides to any position in a given RNA has now become routine. Furthermore, one is not confined to a single modification but can include many variations in each molecule.

It is seemingly out of proportion that one small structural modification could cause such a dilemma. However, the presence of a single hydroxyl at the 2'-position of the ribofuranose ring, has been the major reason that research in the RNA field has lagged so far behind comparable DNA studies. Progress has been made in improving methods for DNA synthesis that have enabled the production of large amounts of antisense deoxyoligonucleotides for structural and therapeutic applications. Only recently have similar gains been achieved for ribonucleotides (Wincott et al., 1995, *Nucleic Acids Research*, 23, 2677-2684; Sproat et al., 1995, *Nucleosides and Nucleotides*, 14, 255-273; Vargeese et al., 1998, *Nucleic Acids Research*, 26, 1046-1050).

The chasm between DNA and RNA synthesis is due to the difficulty of identifying orthogonal protecting groups for the 5'- and 2'-hydroxyls. Historically, two standard approaches have been taken by scientists attempting to solve the RNA synthesis problem; developing a method that is compatible with state-of the-art DNA synthesis or designing an approach specifically suited for RNA. Although adaptation of the DNA process provides a more universal procedure in which non-RNA phosphoramidites can easily be incorporated into RNA oligomers, the advantage to the latter approach is that one can develop a process that is best for RNA synthesis and as a result, better yields can be realized. However, in both cases similar issues are faced, for example identifying protecting groups that are compatible with synthesis conditions yet can be removed at the appropriate juncture. This problem does not refer only to the 2'- and 5'-OH groups, but includes the base and phosphate protecting groups as well. Consequently, the accompanying deprotection steps, in addition to the choice of ancillary agents, are impacted. Another shared issue is the need for efficient synthesis of the monomer building blocks.

Solid phase synthesis of oligoribonucleotides follows the same pathway as DNA synthesis. A solid support with an attached nucleoside is subjected to removal of the protecting group on the 5'-hydroxyl. The incoming phosphoramidite is coupled to the growing chain in the presence of an activator. Any unreacted 5'-hydroxyl is capped and the phosphite triester is then oxidized to provide the desired phosphotriester linkage. The process is then repeated until an oligomer of the desired length results. The actual reagents used may vary according to the 5'- and 2'-protecting groups. Other ancillary reagents may also differ.

Once the oligoribonucleotide has been synthesized, it must then be deprotected. This is typically a two-step process that entails cleavage of the oligomer from the support and deprotection of the base and phosphate blocking groups, followed by removal of the 2'-protecting groups. Occasionally, a different order of reactions or separate deprotection of the phosphate groups is required. In all cases, it is imperative that indiscriminate removal of protecting groups not occur, this is particularly an issue in the classic situation wherein the first step is base mediated. In this case, if the 2'-hydroxyl is revealed under these conditions, strand scission will result due to attack of the vicinal hydroxyl group on the neighboring phosphate backbone. Two other concerns that are prevalent in RNA synthesis but play no part in DNA are the propensity for 3'-2' phosphodiester migration to provide undesired 2'-5' linkages and the susceptibility of oligoribonucleotides to degradation by ribonucleases. The latter fact has led many researchers to develop 2'-protecting groups that can remain in place until the oligomer is required for the desired experiment.

In the past, deprotection of oligoribonucleotides containing a 2'-O-TBDMS (t-butyldimethylsilyl) group was a two step process that first entailed a basic step similar to that used for the deprotection of DNA in which the oligomer was cleaved from the support and the base and phosphate groups were removed. The initial step was accomplished in 1-4 h at 55° C. with 3/1 $NH_4OH/EtOH$. Since the oligomer is not exposed to severe deprotection conditions for prolonged periods, better yields of higher quality product result. More recently, a faster, two step, deprotection protocol, entailing the use of aqueous methylamine has been reported for RNA (Usman et al., U.S. Pat. No. 5,804,683; Wincott et al., 1995, supra; Reddy et al., 1995, *Tetrahedron Lett.*, 36, 8929-8932). Incubation times have been reduced to 10 min at 65° C. When compared with other RNA deprotection methods, treatment with this reagent gave greater full length product than the standard protocol using 3/1 $NH_4OH/EtOH$ (Wincott et al., 1995, supra). The only requirement is that acetyl must be used as the N-protecting group for cytidine because of a well-documented transamination reaction (Reddy et al., 1994, *Tet-* rahedron Lett., 35, 4311-4314). As stated earlier, through the use of methylamine this step has been reduced to 10 minutes. The second step is removal of the 2'-silyl protecting group from the oligonucleotide. In the past this had been accomplished with 1 M n-tetrabutyl ammonium fluoride (TBAF) in THF at room temperature over 24 h (Usman et al., 1987, J. Am. Chem. Soc., 109, 7845-7854; Scaringe et al., 1990, Nucleic Acids Research, 18, 5433-5341). Unfortunately, the use of this deprotecting agent produces salts which must be removed prior to analysis and purification. In addition, the long exposure time required for complete removal of the protecting group, coupled with the reagent's sensitivity to adventitious water (Hogrefe et al., 1994, Nucleic Acids Research, 21, 4739-4741), made it a less than ideal reagent. Although some reports have been published regarding the use of neat triethylamine trihydrofluoride (TEA.3HF) (Duplaa et al., U.S. Pat. No. 5,552,539, Gasparutto et al., 1992, Nucleic Acids Research, 20, 5159-5166; Westman et al., 1994, Nucleic Acids Research, 22, 2430-2431) as a desilylating reagent, results have been mixed. A cocktail of TEA.3HF in combination with N-methyl pyrrolidinone (NMP) (Usman and Wincott, U.S. Pat. No. 5,831,071; Wincott et al., 1995, supra) or DMF (Sproat et al., 1995, supra) has also been described in which full deprotection can be achieved in 30-90 min at 65° C. or 4-8 h at room temperature. As an added advantage, since no salts are produced, the product can be directly precipitated from the desilylating reagent.

Tracz, U.S. Pat. No. 5,977,343; Tracz, U.S. Pat. No. 5,686,599, describes a one-pot protocol for ribonucleotide deprotection using anhydrous methylamine and triethylamine trihydrogen fluoride. This procedure involves the use of anhydrous methylamine followed by neat triethylamine trihydrofluoride to effectively deprotect oligoribonucleotides in a one-pot fashion. However such a protocol may be cumbersome for deprotection of oligonucleotides synthesized on a plate format, such as a 96-well plate, because it may be necessary to separate the solid-support from the partially deprotected oligonucleotide prior to the 2'-hydroxyl deprotection. Also, since the methylamine solution used is anhydrous, it may be difficult to solubilize the negatively charged oligoribonucleotides obtained after basic treatment. More recently this procedure has been reported in which both the basic deprotection and the desilylation reaction can be accomplished in one-pot using a mixture of anhydrous methylamine in ethanol followed by addition of TEA-3HF (Bellon, 1999, Current Protocols in Nucleic Acid Chemistry, Beaucage, Bergstrom, Glick and Jones, eds., in press). This protocol allows for the complete deprotection of an oligoribonucleotide in less than 2 h without any evidence of 3'-2' migration.

The parameters of 2'-deprotection are dictated by the corresponding protecting groups utilized for differing 2'-chemistries present within a given oligonucleotide. The use of alternate 2'-ribofuranosyl carbocycle functions within the same oligonucleotide molecule can present potential problems with respect to the synthesis, deprotection, and purification of such molecules. The efficient synthesis of nucleic acids which are chemically modified to increase nuclease resistance while maintaining catalytic activity is of importance to the potential development of new therapeutic agents. Recently, Beaudry et al., 2000, Chemistry and Biology, 7, in press, describe the in vitro selection of a novel nuclease-resistant RNA phosphodiesterase. This enzymatic nucleic acid molecule can contain both ribo (2'-hydroxyl) and amino (2'-deoxy-2'-amino) functions. The large scale synthesis of oligonucleotides with both ribo and amino functions presents practical problems with regard to the concomitant removal of tert-Butyldimethylsilyl (TBDMSi) and N-phthaloyl protecting groups, while at the same time preserving the integrity of the ribonucleotide linkages. The use of the N-phthaloyl protecting group for the 2'-amino group during oligonucleotide synthesis offers the benefit of improved synthetic yields compared to the trifluoroacetyl (TFA) and FMOC groups (Usman et al., U.S. Pat. No. 5,631,360; Beigelman et al., 1995, Nucleic Acids Research, 23(21), 4434-4442). The phthaloyl group is readily cleaved with aqueous methylamine at 65° C. and the TBDMSi group is readily cleaved using a fluoride ion source, such as tetrabutylammonium fluoride (TBAF) or triethylammonium trihydrofluoride (TEA.3HF). Application of the "one pot" deprotection procedures described above results in the incomplete deprotection of N-phthaloyl protection. The two step deprotection procedure can be employed for the complete deprotection of oligonucleotides containing both ribo (2'-TBDMS) and amino (N-phthaloyl) protecting groups, however, this process is not readily amenable to large scale oligonucleotide synthesis or multiwell plate oligonucleotide synthesis.

As such there exists an unmet need for a fast, efficient method which allows for the complete deprotection of molecules containing both amino and ribo carbohydrate moieties. Such a method will enable the large scale synthesis of such molecules for use as therapeutic agents and the small scale synthesis of such molecules for combinatorial screening.

SUMMARY OF THE INVENTION

Current oligonucleotide deprotection methods for oligonucleotides comprising one or more ribonucleotides are limited by both the length of time needed for complete deprotection and by the incomplete deprotection of certain protecting groups (for example N-phthaloyl). The use of anhydrous methylamine and triethylamine trihydrofluoride as a "one pot" deprotection cocktail makes use of DMSO to solubilize the partially deprotected oligonucleotide under anhydrous conditions (Tracz, U.S. Pat. No. 5,977,343). The use of aqueous methylamine has been avoided in combination with triethylamine trihydrofluoride up to this point due to the presumed susceptibility of ribonucleotide linkages to degradation under these conditions (for example, see example 3 described herein) as a result of alkaline hydrolysis (Brown et al., 1952, J. Chem. Soc., London, 2708). This has been overcome with the separation of the aqueous methylamine treatment from the triethylamine trihydrofluoride treatment by making use of an intermediary drying step to remove the aqueous methylamine reagent prior to removal of the 2'-hydroxyl protecting group, thereby precluding alkaline hydrolysis of the ribonucleotide linkages. This two step process is not amenable to large scale oligonucleotide synthesis and oligonucleotide synthesis performed on a multi-well plate, high throughput format. The use of a "one-pot" deprotection method comprising treatment with anhydrous methylamine and triethylamine trihydrofluoride in the presence of DMSO as a co-solvent is benign to ribonucleotide linkages, however, this process may require additional optimization in terms of both total deprotection time and resulting oligonucleotide quality. In addition, the "one-pot" anhydrous method is not very effective for the complete removal of some protecting groups (for example N-phthaloyl). The deprotection method of the instant invention provides a rapid, "one-pot" method for the complete deprotection of oligonucleotides comprising one or more ribonucleotides, and is further capable of complete deprotection of a wide variety of oligonucleotide protecting groups, including the N-phthaloyl group.

This invention concerns a process for the deprotection and purification of molecules comprising one or more ribonucleotides. Specifically, the present invention features a method for the removal of protecting groups from nucleic acid base, phosphate, and 2'-hydroxyl (2'-OH) and/or 2'-deoxy-2'-amino (2'-NH$_2$) groups, which allows the deprotection and subsequent purification of molecules comprising one or more ribonucleotides in both a large scale and a high throughput manner.

In a preferred embodiment, the invention features a one-pot process for rapid deprotection of molecules comprising one or more ribonucleotides. In additional embodiments, the instant invention features a process for the rapid deprotection of molecules comprising ribonucleotides and/or 2'-deoxy-2'-amino ribofuranose moieties which are protected with alkyl-silyl and/or phthaloyl-based protecting groups respectively. Specifically, the invention provides a process for the rapid deprotection of molecules comprising both ribonucleotides and/or 2'-deoxy-2'-amino ribofuranose moieties which are protected with t-butyldimethylsilyl (TBDMSi) and/or N-phthaloyl protecting groups respectively In preferred embodiments, the instant invention features the use of an aqueous methylamine solution to partially deprotect molecules comprising one or more ribonucleotides followed by treatment with triethylammonium trihydrofluoride for the complete deprotection of molecules. In another embodiment, the treatment with triethylammonium trihydrofluoride is in the presence of a co-solvent (for example, DMSO).

In one embodiment, the invention features a process for the synthesis, deprotection, and purification of molecules comprising one or more ribonucleotides, comprising the steps of: (a) solid phase, solution phase, and/or hybrid phase, (e.g.; phosphoramidite-based or H-phosphonate-based) oligonucleotide synthesis comprising the steps of detritylation, activation, coupling, capping, and oxidation or the equivalent thereof, in any suitable order, followed by (b) deprotection comprising contacting the nucleic acid molecule having one or more ribonucleotides with aqueous alkylamine (where alkyl can be ethyl, propyl or butyl and is preferably methyl, e.g.; methylamine, for example 40% aqueous methylamine), and/or trialkylamine (where alkyl can be methyl, propyl or butyl and is preferably ethyl, e.g.; triethylamine) at about 10 to about 100° C., or about 20° C. to about 80° C., or about 30° C. to about 65° C., preferably about 35° C. or about 65° C. for molecules comprising N-phthaloyl protecting groups, for about 5 to about 240 minutes, about 20 to about 100 minutes, preferably about 60 minutes under conditions suitable for partial deprotection of the oligonucleotide, and contacting the partially deprotected molecule comprising one or more ribonucleotides with triethylamine.trihydrofluoride (TEA.3HF) in the presence of a solvent (for example DMSO, DMF, HMPA, ethanol, methanol, isopropanol, N-methylpyrrolidinone and others) and heating at about 10 to about 100° C., preferably at about 65° C., for about 5 to about 240 minutes, preferably about 60 minutes, to remove 2'-hydroxyl protecting groups (for example, t-butyldimethylsilyl), then quenching the deprotection reaction by using aqueous sodium acetate, ammonium bicarbonate, and/or triethylammonium bicarbonate or the equivalent thereof, preferably 50 mM aqueous sodium acetate, then (c) purifying the molecule comprising one or more ribonucleotides, comprising loading the deprotected products onto media comprising Pharmacia Source Q15 and Biorad Macroprep 25Q media, or the equivalent thereof such as Pharmacia Q-sepharose, Perceptive POROS HQ, TOSOHAAS Q-5PW-HR, Q-5PW, or super Q-5PW, equilibrated with a buffer comprising either 20% ethanol or acetonitrile in about 20 mM sodium phosphate and about 0.1 M NaCl, in a loading buffer comprising water, or either 20% ethanol or acetonitrile in about 20 mM sodium phosphate and about 0.1 M NaCl, and applying a suitable gradient of about 1.0 M NaCl as an elution buffer, then analyzing the fractions by a suitable technique and allowing for the pure fractions to be pooled and desalted via tangential flow filtration or the equivalent thereof, by using membranes comprising such membranes as those selected from the group consisting of Sartorius or Pall Filtron PES 1 K membranes, then lyophilizing the concentrated material.

In one embodiment, the invention features a process for the synthesis, deprotection, and purification of a nucleic acid molecule comprising one or more ribonucleotides and one or more chemical modifications, comprising the steps of: (a) solid phase, solution phase, and/or hybrid phase, (e.g.; phosphoramidite-based or H-phosphonate-based) oligonucleotide synthesis comprising the steps of detritylation, activation, coupling, capping, and oxidation or the equivalent thereof, in any suitable order, followed by (b) deprotection comprising contacting the nucleic acid molecule with aqueous alkylamine (where alkyl can be ethyl, propyl or butyl and is preferably methyl, e.g.; methylamine, for example 40% aqueous methylamine), and/or trialkylamine (where alkyl can be methyl, propyl or butyl and is preferably ethyl, e.g.; triethylamine) at about 10 to about 100° C., or about 20° C. to about 80° C., or about 30° C. to about 65° C., preferably about 35° C. or about 65° C. for molecules comprising N-phthaloyl protecting groups, for about 5 to about 240 minutes, about 20 to about 100 minutes, preferably about 60 minutes under conditions suitable for partial deprotection of the nucleic acid molecule, and contacting the partially deprotected molecule comprising one or more ribonucleotides with triethylamine.trihydrofluoride (TEA.3HF) in the presence of a solvent (for example DMSO, DMF, HMPA, ethanol, methanol, isopropanol, N-methylpyrrolidinone and others) and heating at about about 10 to about 100° C., preferably at about 65° C., for about 5 to about 240 minutes, preferably about 60 minutes, to remove 2'-hydroxyl protecting groups (for example, t-butyldimethylsilyl), then quenching the deprotection reaction by using aqueous sodium acetate, ammonium bicarbonate, and/or triethylammonium bicarbonate or the equivalent thereof, preferably 50 mM aqueous sodium acetate, then (c) purifying the nucleic acid molecule, comprising loading the deprotected products onto media comprising Pharmacia Source Q15 and Biorad Macroprep 25Q media, or the equivalent thereof such as Pharmacia Q-sepharose, Perceptive POROS HQ, TOSOHAAS Q-5PW-HR, Q-5PW, or super Q-5PW, equilibrated with a buffer comprising either 20% ethanol or acetonitrile in about 20 mM sodium phosphate and about 0.1 M NaCl, in a loading buffer comprising water, or either 20% ethanol or acetonitrile in about 20 mM sodium phosphate and about 0.1 M NaCl, and applying a suitable gradient of about 1.0 M NaCl as an elution buffer, then analyzing the fractions by a suitable technique and allowing for the pure fractions to be pooled and desalted via tangential flow filtration or the equivalent thereof, by using membranes comprising such membranes as those selected from the group consisting of Sartorius or Pall Filtron PES 1 K membranes, then lyophilizing the concentrated material. In another embodiment, the chemical modifications, which may be same or different, independently include sugar modifications, such as 2'-deoxy-2'-fluoro, 2'-O-methyl, 2'-C-alkyl, 2'-deoxy, 2'-deoxy-2'-amino or LNA (locked nucleic acid) nucleosides. In another embodiment, the chemical modifications in the nucleic acid molecule, which may be same or different, includes one or more phosphorothioate internucleotide linkages. In another embodiment, the chemical modification of nucleic acid molecule, which may be same or different, comprises modifying the terminal positions with one or more abasic moieties. In another embodiment, the chemically modified nucleic acid molecule comprises a terminal cap moiety at the 3'-end, 5'-end, or both 3' and 5' ends of the oligonucleotide.

In another embodiment the nucleic acid molecules synthesized, deprotected and/or purified according to the invention comprise a combination of sugar, phosphate backbone, base, and/or terminal end modifications.

In one embodiment, the invention features a process for the deprotection and subsequent purification of nucleic acid molecules having one or more ribonucleotides with protecting groups, comprising the steps of: (a) deprotection comprising contacting the nucleic acid molecule with aqueous alkylamine (where alkyl can be ethyl, propyl or butyl and is preferably methyl, e.g.; methylamine, for example 40% aqueous methylamine), and/or trialkylamine (where alkyl can be methyl, propyl or butyl and is preferably ethyl, e.g.; triethylamine) at about 10 to about 100° C., or about 20° C. to about 80° C., or about 30° C. to about 65° C., preferably about 35° C. or about 65° C. for molecules comprising N-phthaloyl protecting groups, for about 5 to about 240 minutes, or about 20 to about 100 minutes, preferably about 60 minutes under conditions suitable for partial deprotection of the oligonucleotide, and contacting the partially deprotected molecule with triethylamine.trihydrofluoride (TEA.3HF) in the presence of a solvent (for example DMSO, DMF, HMPA, ethanol, methanol, isopropanol, N-methylpyrrolidinone and others) and heating at about 10 to about 100° C., preferably at about 65° C., for about 5 to about 240 minutes, preferably about 60 minutes, to remove 2'-hydroxyl protecting groups (for example, t-butyldimethylsilyl), then quenching the deprotection reaction by using aqueous sodium acetate, ammonium bicarbonate, and/or triethylammonium bicarbonate or the equivalent thereof, preferably 50 mM aqueous sodium acetate, then (b) purifying the molecule comprising one or more ribonucleotides, comprising loading the deprotection products onto media comprising Pharmacia Source Q15 and Biorad Macroprep 25Q media, or the equivalent thereof, such as Pharmacia Q-sepharose, Perceptive POROS HQ, TOSOHAAS Q-5PW-HR, Q-5PW, or super Q-5PW, equilibrated with a buffer comprising either 20% ethanol or acetonitrile in about 20 mM sodium phosphate and about 0.1 M NaCl, in a loading buffer comprising water, or either 20% ethanol or acetonitrile in about 20 mM sodium phosphate and about 0.1 M NaCl, and applying a suitable gradient of about 1.0 M NaCl as an elution buffer, then analyzing the fractions by a suitable technique and allowing for the pure fractions to be pooled and desalted via tangential flow filtration or the equivalent thereof, by using membranes comprising such membranes as those selected from the group consisting of Sartorius or Pall Filtron PES 1 K membranes, then lyophilizing the concentrated material.

In one embodiment, the invention features a process for the deprotection and subsequent purification of nucleic acid molecules having one or more ribonucleotides one or more chemical modifications, and with protecting groups, comprising the steps of: (a) deprotection comprising contacting the nucleic acid molecule with aqueous alkylamine (where alkyl can be ethyl, propyl or butyl and is preferably methyl, e.g.; methylamine, for example 40% aqueous methylamine), and/or trialkylamine (where alkyl can be methyl, propyl or butyl and is preferably ethyl, e.g.; triethylamine) at about 10 to about 100° C., or about 20° C. to about 80° C., or about 30° C. to about 65° C., preferably about 35° C. or about 65° C. for nucleic acid molecules comprising N-phthaloyl protecting groups, for about 5 to about 240 minutes, or about 20 to about 100 minutes, preferably about 60 minutes under conditions suitable for partial deprotection of the nucleic acid molecule, and contacting the partially deprotected molecule with triethylamine.trihydrofluoride (TEA.3HF) in the presence of a solvent (for example DMSO, DMF, HMPA, ethanol, methanol, isopropanol, N-methylpyrrolidinone and others) and heating at about 10 to about 100° C., preferably at about 65° C., for about 5 to about 240 minutes, preferably about 60 minutes, to remove 2'-hydroxyl protecting groups (for example, t-butyldimethylsilyl), then quenching the deprotection reaction by using aqueous sodium acetate, ammonium bicarbonate, and/or triethylammonium bicarbonate or the equivalent thereof, preferably 50 mM aqueous sodium acetate, then (b) purifying the nucleic acid molecule, comprising loading the deprotection products onto media comprising Pharmacia Source Q15 and Biorad Macroprep 25Q media, or the equivalent thereof, such as Pharmacia Q-sepharose, Perceptive POROS HQ, TOSOHAAS Q-5PW-HR, Q-5PW, or super Q-5PW, equilibrated with a buffer comprising either 20% ethanol or acetonitrile in about 20 mM sodium phosphate and about 0.1 M NaCl, in a loading buffer comprising water, or either 20% ethanol or acetonitrile in about 20 mM sodium phosphate and about 0.1 M NaCl, and applying a suitable gradient of about 1.0 M NaCl as an elution buffer, then analyzing the fractions by a suitable technique and allowing for the pure fractions to be pooled and desalted via tangential flow filtration or the equivalent thereof, by using membranes comprising such membranes as those selected from the group consisting of Sartorius or Pall Filtron PES 1 K membranes, then lyophilizing the concentrated material. In another embodiment, the chemically modified nucleic acid molecule comprises independently one or more 2'-deoxy-2'-fluoro, 2'-O-methyl, 2'-C-alkyl, 2'-deoxy, 2'-deoxy-2'-amino or LNA (locked nucleic acid) nucleosides. In another embodiment, the chemically modified nucleic acid molecule comprises one or more phosphorothioate internucleotide linkages. In another embodiment, the chemically modified nucleic acid molecule comprises one or more abasic moieties. In another embodiment, the chemically modified nucleic acid molecule comprises a terminal cap moiety at the 3'-end, 5'-end, or both 3' and 5' ends of the oligonucleotide.

In yet another preferred embodiment, the invention features a process for one pot deprotection of nucleic acid molecules having one or more ribonucleotides with protecting groups, comprising the steps of: (a) contacting the nucleic acid molecule with aqueous alkylamine (where alkyl can be ethyl, propyl or butyl and is preferably methyl, e.g.; methylamine, for example 40% aqueous methylamine), and/or trialkylamine (where alkyl can be methyl, propyl or butyl and is preferably ethyl, e.g.; triethylamine) at about 10 to about 100° C., or about 20° C. to about 80° C., or about 30° C. to about 65° C., preferably about 35° C. or about 65° C. for molecules comprising N-phthaloyl protecting groups, for about 5 to about 240 minutes, or about 20 to about 100 minutes, preferably about 60 minutes, under conditions suitable for partial deprotection of the oligonucleotide, and (b) contacting the partially deprotected molecule with triethylamine.trihydrofluoride (TEA.3HF) in the presence of a solvent (for example DMSO DMF, HMPA, ethanol, methanol, isopropanol, N-methylpyrrolidinone and others) and heating at about 10 to 100° C., preferably at about 65° C., for about 5 to 240 minutes, preferably about 60 minutes, to remove 2'-hydroxyl protecting groups (for example, t-butyldimethylsilyl). In additional embodiments, other alkylamine.HF complexes may also be used, (e.g.; trimethylamine trihydrofluoride and/or diisopropylethylamine trihydrofluoride) under conditions suitable for the complete deprotection of the molecule.

In yet another preferred embodiment, the invention features a process for one pot deprotection of nucleic acid molecules having one or more ribonucleotides, one or more chemical modifications, and with protecting groups, comprising the steps of: (a) contacting the nucleic acid molecule with aqueous alkylamine (where alkyl can be ethyl, propyl or butyl and is preferably methyl, e.g.; methylamine, for example 40% aqueous methylamine), and/or trialkylamine (where alkyl can be methyl, propyl or butyl and is preferably ethyl, e.g.; triethylamine) at about 10 to 100° C., or about 20° C. to about 80° C., or about 30° C. to about 65° C., preferably about 35° C. or about 65° C. for molecules comprising N-phthaloyl protecting groups, for about 5 to about 240 minutes, or about 20 to about 100 minutes, preferably about 60 minutes, under conditions suitable for partial deprotection of the nucleic acid molecule, and (b) contacting the partially deprotected molecule with triethylamine.trihydrofluoride (TEA.3HF) in the presence of a solvent (for example DMSO DMF, HMPA, ethanol, methanol, isopropanol, N-methylpyrrolidinone and others) and heating at about 10 to 100° C., preferably at about 65° C., for about 5 to 240 minutes, preferably about 60 minutes, to remove 2'-hydroxyl protecting groups (for example, t-butyldimethylsilyl). In additional embodiments, other alkylamine.HF complexes may also be used, (e.g.; trimethylamine trihydrofluoride and/or diisopropylethylamine trihydrofluoride) under conditions suitable for the complete deprotection of the molecule. In another embodiment, the chemically modified nucleic acid molecule comprises independently one or more 2'-deoxy-2'-fluoro, 2'-O-methyl, 2'-C-alkyl, 2'-deoxy, 2'-deoxy-2'-amino or LNA (locked nucleic acid) nucleosides. In another embodiment, the chemically modified nucleic acid molecule comprises one or more phosphorothioate internucleotide linkages. In another embodiment, the chemically modified nucleic acid molecule comprises one or more abasic moieties. In another embodiment, the chemically modified nucleic acid molecule comprises a terminal cap moiety at the 3'-end, 5'-end, or both 3' and 5' ends of the oligonucleotide.

In a preferred embodiment, the invention features a process for purifying a nucleic acid molecule, comprising the steps of: (a) loading the crude deprotected molecule onto media comprising Pharmacia Source Q15 and Biorad Macroprep 25Q media, or the equivalent thereof such as Pharmacia Q-sepharose, Perceptive POROS HQ, TOSOHAAS Q-5PW-HR, Q-5PW, or super Q-5PW, equilibrated with a buffer comprising either 20% ethanol or acetonitrile in about 20 mM sodium phosphate and about 0.1 M NaCl, in a loading buffer comprising water, or either 20% ethanol or acetonitrile in about 20 mM sodium phosphate and about 0.1 M NaCl, and (b) applying a suitable gradient of about 1.0 M NaCl as an elution buffer, then analyzing the fractions by a suitable technique and allowing for the pure fractions to be pooled and desalted via tangential flow filtration or the equivalent thereof, by using membranes comprising such membranes as those selected from the group consisting of Sartorius or Pall Filtron PES 1 K membranes.

In a preferred embodiment, the invention features a process for purifying a chemically modified nucleic acid molecule, comprising the steps of: (a) loading the crude deprotected molecule onto media comprising Pharmacia Source Q15 and Biorad Macroprep 25Q media, or the equivalent thereof such as Pharmacia Q-sepharose, Perceptive POROS HQ, TOSOHAAS Q-5PW-HR, Q-5PW, or super Q-5PW, equilibrated with a buffer comprising either 20% ethanol or acetonitrile in about 20 mM sodium phosphate and about 0.1 M NaCl, in a loading buffer comprising water, or either 20% ethanol or acetonitrile in about 20 mM sodium phosphate and about 0.1 M NaCl, and (b) applying a suitable gradient of about 1.0 M NaCl as an elution buffer, then analyzing the fractions by a suitable technique and allowing for the pure fractions to be pooled and desalted via tangential flow filtration or the equivalent thereof, by using membranes comprising such membranes as those selected from the group consisting of Sartorius or Pall Filtron PES 1 K membranes. In another embodiment, the chemically modified nucleic acid molecule comprises independently one or more 2'-deoxy-2'-fluoro, 2'-O-methyl, 2'-C-alkyl, 2'-deoxy, 2'-deoxy-2'-amino or LNA (locked nucleic acid) nucleosides. In another embodiment, the chemically modified nucleic acid molecule comprises one or more phosphorothioate internucleotide linkages. In another embodiment, the chemically modified nucleic acid molecule comprises one or more abasic moieties. In another embodiment, the chemically modified nucleic acid molecule comprises a terminal cap moiety at the 3'-end, 5'-end, or both 3' and 5' ends of the oligonucleotide.

In an additional preferred embodiment, the nucleic acid molecule or chemically modified nucleic acid molecule is lyophilized after purification.

In preferred embodiments, the deprotection reaction can be quenched by using aqueous sodium acetate, ammonium bicarbonate, and/or triethylammonium bicarbonate or the equivalent thereof, preferably 50 mM aqueous sodium acetate.

In another preferred embodiment, the invention features a process for the deprotection of nucleic acid molecules comprising an oligonucleotide having 2'-N-phthaloyl and 2'-O-silyl protection comprising the steps of: (a) contacting the nucleic acid molecule with aqueous alkylamine (where alkyl can be ethyl, propyl or butyl and is preferably methyl, e.g.; methylamine, for example 40% aqueous methylamine), and/or trialkylamine (where alkyl can be methyl, propyl or butyl and is preferably ethyl, e.g.; triethylamine) at about 10 to 100° C., or about 20° C. to about 80° C., or about 30° C. to about 65° C., preferably about 35° C. or about 65° C. for molecules comprising N-phthaloyl protecting groups, for about 5 to about 240 minutes, or about 20 to about 100 minutes, preferably about 60 minutes, under conditions suitable for partial deprotection of the oligonucleotide, and (b) contacting the partially deprotected molecule with triethylamine.trihydrofluoride (TEA.3HF) in the presence of a solvent (for example DMSO DMF, HMPA, ethanol, methanol, isopropanol, N-methylpyrrolidinone and others) and heating at about 10 to 100° C., preferably at about 65° C., for about 5 to 240 minutes, preferably about 60 minutes, to remove 2'-hydroxyl protecting groups (for example, t-butyldimethylsilyl). In additional embodiments, other alkylamine.HF complexes may also be used, (e.g.; trimethylamine trihydrofluoride and/or diisopropylethylamine trihydrofluoride) under conditions suitable for the complete deprotection of the molecule. The nucleic acid molecule can further comprise chemical modifications, such as one or more 2'-deoxy-2'-fluoro, 2'-O-methyl, 2'-C-alkyl, 2'-deoxy, 2'-deoxy-2'-amino or LNA (locked nucleic acid) nucleosides; one or more phosphorothioate internucleotide linkages; one or more abasic moieties; or a terminal cap moiety at the 3'-end, 5'-end, or both 3' and 5' ends of the oligonucleotide.

In a preferred embodiment, the partially deprotected molecule is filtered using a suitable filtering medium, such as sintered glass, and washed with a polar solvent (for example, DMSO, DMF, ethanol, methanol, isopropanol, and/or N-methylpyrrolidinone) prior to treatment with TEA.3HF reagent.

In additional embodiments, the filtrate is cooled prior to treatment with TEA.3HF reagent, preferably to between about 0° C. and −78° C.

In another aspect the invention features a process for oligonucleotide deprotection where the deprotection reaction is performed with the aqueous methylamine solution at temperatures ranging from about 0° C. to 120° C. for a time of about 500 minutes to about 5 minutes.

In one embodiment, the invention features a process for deprotecting oligonucleotides including one or more 2'-deoxy-2'-fluoro nucleotides comprising: contacting the oligonucleotide with a solution of aqueous methylamine (e.g. 40% aqueous methylamine) at about 25° C. to about 45° C. for about 30 minutes. In another embodiment, the oligonucleotide is contacted with the solution of aqueous methylamine at about 35° C. for about 30 minutes.

In one embodiment, the invention features a process for deprotecting oligonucleotides including one or more 2'-deoxy-2'-fluoro nucleotides and one or more ribonucleotides comprising: (a) contacting the oligonucleotide with a solution of aqueous methylamine (e.g. 40% aqueous methylamine) at about 25° C. to about 45° C. for about 30 minutes, and (b) contacting the partially deprotected molecule of (a) with triethylamine.trihydrofluoride (TEA.3HF) in the presence of a solvent (for example DMSO DMF, HMPA, ethanol, methanol, isopropanol, N-methylpyrrolidinone and others) and heating at about 10 to 100° C., preferably at about 65° C., for an additional 5 to 60 minutes, preferably about 15 minutes, to remove 2'-hydroxyl protecting groups (for example, t-butyldimethylsilyl). In additional embodiments, other alkylamine.HF complexes may also be used, (e.g.; trimethylamine trihydrofluoride and/or diisopropylethylamine trihydrofluoride) under conditions suitable for the complete deprotection of the molecule. In another embodiment, the oligonucleotide in (a) is contacted with the solution of aqueous methylamine at about 35° C. for about 30 minutes.

In one embodiment, a process for deprotection of molecules comprising one or more ribonucleotides of the present invention is used to deprotect an oligonucleotide synthesized using a column format.

In one embodiment, a process for deprotection of molecules comprising one or more ribonucleotides of the present invention is used to deprotect an oligonucleotide synthesized according to methods described in Usman et al., U.S. Pat. Nos. 5,804,683; 5,831,071; 5,998,203; 6,117,657; 6,353,098; 6,362,323; 6,437,117; 6,469,158; and/or Vargeese et al., U.S. Ser. No. 10/190,359, all incorporated by reference herein in their entirety including the drawings.

In one embodiment, the invention features a method comprising: (a) synthesizing an oligonucleotide molecule having one or more ribonucleotides, (b) contacting the oligonucleotide with aqueous alkylamine (where alkyl can be ethyl, propyl or butyl and is preferably methyl, e.g.; methylamine, for example 40% aqueous methylamine), and/or trialkylamine (where alkyl can be methyl, propyl or butyl and is preferably ethyl, e.g.; triethylamine) at about 10 to about 100° C., or about 20° C. to about 80° C., or about 30° C. to about 65° C., preferably 35° C. or 65° C. for about 15 to 240 minutes, preferably about 30 to about 60 minutes, under conditions suitable for partial deprotection of the oligonucleotide, and (c) contacting the partially deprotected molecule with triethylamine.trihydrofluoride (TEA.3HF) in the presence of a solvent (for example DMSO DMF, HMPA, ethanol, methanol, isopropanol, N-methylpyrrolidinone and others) and heating at about 10 to about 100° C., preferably at about 65° C., for about 15 to 240 minutes, preferably about 30 to about 60 minutes, to remove 2'-hydroxyl protecting groups (for example, t-butyldimethylsilyl). In additional embodiments, other alkylamine.HF complexes may also be used, (e.g.; trimethylamine trihydrofluoride and/or diisopropylethylamine trihydrofluoride) under conditions suitable for the complete deprotection of the molecule.

In one embodiment, the invention features a method comprising: (a) synthesizing an oligonucleotide molecule having one or more ribonucleotides, (b) contacting the oligonucleotide with aqueous alkylamine (where alkyl can be ethyl, propyl or butyl and is preferably methyl, e.g.; methylamine, for example 40% aqueous methylamine), at about 35° C. to about 65° C. for about 15 to about 240 minutes, (e.g. about 30 to about 60 minutes, under conditions suitable for partial deprotection of the oligonucleotide, and (c) contacting the partially deprotected molecule with triethylamine.trihydrofluoride (TEA.3HF) in the presence of a solvent (for example DMSO DMF, HMPA, ethanol, methanol, isopropanol, N-methylpyrrolidinone and others) and heating at about 10 to 100° C., preferably at about 65° C., for about 15 to 240 minutes, preferably about 60 minutes, to remove 2'-hydroxyl protecting groups (for example, t-butyldimethylsilyl). In additional embodiments, other alkylamine.HF complexes may also be used, (e.g.; trimethylamine trihydrofluoride and/or diisopropylethylamine trihydrofluoride) under conditions suitable for the complete deprotection of the molecule.

In one embodiment, the invention features a method comprising: (a) synthesizing an oligonucleotide molecule having one or more 2'-deoxy-2'-fluoro nucleotides and one or more ribonucleotides, (b) contacting the oligonucleotide with aqueous alkylamine (where alkyl can be ethyl, propyl or butyl and is preferably methyl, e.g.; methylamine, for example 40% aqueous methylamine), and/or trialkylamine (where alkyl can be methyl, propyl or butyl and is preferably ethyl, e.g.; triethylamine) at about 10 to about 100° C., or about 20° C. to about 80° C., or about 30° C. to about 65° C., preferably 35° C. for about 15 to 240 minutes, preferably about 30 minutes, under conditions suitable for partial deprotection of the oligonucleotide, and (c) contacting the partially deprotected molecule with triethylamine.trihydrofluoride (TEA.3HF) in the presence of a solvent (for example DMSO DMF, HMPA, ethanol, methanol, isopropanol, N-methylpyrrolidinone and others) and heating at about 10 to about 100° C., preferably at about 65° C., for about 15 to 240 minutes, preferably about 15 to about 30 minutes, to remove 2'-hydroxyl protecting groups (for example, t-butyldimethylsilyl). In additional embodiments, other alkylamine.HF complexes may also be used, (e.g.; trimethylamine trihydrofluoride and/or diisopropylethylamine trihydrofluoride) under conditions suitable for the complete deprotection of the molecule.

In one embodiment, the invention features a method comprising: (a) synthesizing an oligonucleotide molecule having one or more 2'-deoxy-2'-fluoro nucleotides and one or more ribonucleotides, (b) contacting the oligonucleotide with aqueous alkylamine (where alkyl can be ethyl, propyl or butyl and is preferably methyl, e.g.; methylamine, for example 40% aqueous methylamine), at about 30° C. to about 65° C., preferably about 35° C. for about 15 to about 240 minutes, (e.g. about 30 to about 60 minutes, under conditions suitable for partial deprotection of the oligonucleotide, and (c) contacting the partially deprotected molecule with triethylamine.trihydrofluoride (TEA.3HF) in the presence of a solvent (for example DMSO DMF, HMPA, ethanol, methanol, isopropanol, N-methylpyrrolidinone and others) and heating at about 10 to 100° C., preferably at about 65° C., for about 15 to 240 minutes, preferably about 15 to about 30 minutes, to remove 2'-hydroxyl protecting groups (for example, t-butyldimethylsilyl). In additional embodiments, other alkylamine.HF complexes may also be used, (e.g.; trimethylamine trihydrofluoride and/or diisopropylethylamine trihydrofluoride) under conditions suitable for the complete deprotection of the molecule.

In one embodiment, the invention features a method comprising: (a) synthesizing an oligonucleotide molecule having one or more ribonucleotides, (b) contacting the oligonucleotide with aqueous alkylamine (where alkyl can be ethyl, propyl or butyl and is preferably methyl, e.g.; methylamine, for example 40% aqueous methylamine), and/or trialkylamine (where alkyl can be methyl, propyl or butyl and is preferably ethyl, e.g.; triethylamine) at about 10 to about 100° C., or about 20° C. to about 80° C., or about 30° C. to about 65° C., preferably 35° C. or 65° C. for about 15 to 240 minutes, preferably about 30 to about 60 minutes, under conditions suitable for partial deprotection of the oligonucleotide, (c) contacting the partially deprotected molecule with triethylamine.trihydrofluoride (TEA.3HF) in the presence of a solvent (for example DMSO DMF, HMPA, ethanol, methanol, isopropanol, N-methylpyrrolidinone and others) and heating at about 10 to about 100° C., preferably at about 65° C., for about 15 to 240 minutes, preferably about 30 to about 60 minutes, to remove 2'-hydroxyl protecting groups (for example, t-butyldimethylsilyl, and (d), purifying the deprotected oligonucleotide under conditions suitable for isolating the oligonucleotide.

In one embodiment, the invention features a method comprising: (a) synthesizing an oligonucleotide molecule having one or more ribonucleotides, (b) contacting the oligonucleotide with aqueous alkylamine (where alkyl can be ethyl, propyl or butyl and is preferably methyl, e.g.; methylamine, for example 40% aqueous methylamine), at about 35° C. to about 65° C. for about 15 to about 240 minutes, (e.g. about 30 to about 60 minutes, under conditions suitable for partial deprotection of the oligonucleotide, and (c) contacting the partially deprotected molecule with triethylamine.trihydrofluoride (TEA.3HF) in the presence of a solvent (for example DMSO DMF, HMPA, ethanol, methanol, isopropanol, N-methylpyrrolidinone and others) and heating at about 10 to 100° C., preferably at about 65° C., for about 15 to 240 minutes, preferably about 60 minutes, to remove 2'-hydroxyl protecting groups (for example, t-butyldimethylsilyl), and (d), purifying the deprotected oligonucleotide under conditions suitable for isolating the oligonucleotide.

In one embodiment, the invention features a method comprising: (a) synthesizing an oligonucleotide molecule having one or more 2'-deoxy-2'-fluoro nucleotides and one or more ribonucleotides, (b) contacting the oligonucleotide with aqueous alkylamine (where alkyl can be ethyl, propyl or butyl and is preferably methyl, e.g.; methylamine, for example 40% aqueous methylamine), and/or trialkylamine (where alkyl can be methyl, propyl or butyl and is preferably ethyl, e.g.; triethylamine) at about 10 to about 100° C., or about 20° C. to about 80° C., or about 30° C. to about 65° C., preferably 35° C. for about 15 to 240 minutes, preferably about 30 minutes, under conditions suitable for partial deprotection of the oligonucleotide, and (c) contacting the partially deprotected molecule with triethylamine.trihydrofluoride (TEA.3HF) in the presence of a solvent (for example DMSO DMF, HMPA, ethanol, methanol, isopropanol, N-methylpyrrolidinone and others) and heating at about 10 to about 100° C., preferably at about 65° C., for about 15 to 240 minutes, preferably about 15 to about 30 minutes, to remove 2'-hydroxyl protecting groups (for example, t-butyldimethylsilyl). In additional embodiments, other alkylamine.HF complexes may also be used, (e.g.; trimethylamine trihydrofluoride and/or diisopropylethylamine trihydrofluoride) under conditions suitable for the complete deprotection of the molecule, and (d), purifying the deprotected oligonucleotide under conditions suitable for isolating the oligonucleotide.

In one embodiment, the invention features a method comprising: (a) synthesizing an oligonucleotide molecule having one or more 2'-deoxy-2'-fluoro nucleotides and one or more ribonucleotides, (b) contacting the oligonucleotide with aqueous alkylamine (where alkyl can be ethyl, propyl or butyl and is preferably methyl, e.g.; methylamine, for example 40% aqueous methylamine), at about 30° C. to about 65° C., preferably about 35° C. for about 15 to about 240 minutes, (e.g. about 30 to about 60 minutes, under conditions suitable for partial deprotection of the oligonucleotide, and (c) contacting the partially deprotected molecule with triethylamine.trihydrofluoride (TEA.3HF) in the presence of a solvent (for example DMSO DMF, HMPA, ethanol, methanol, isopropanol, N-methylpyrrolidinone and others) and heating at about 10 to 100° C., preferably at about 65° C., for about 15 to 240 minutes, preferably about 15 to about 30 minutes, to remove 2'-hydroxyl protecting groups (for example, t-butyldimethylsilyl). In additional embodiments, other alkylamine.HF complexes may also be used, (e.g.; trimethylamine trihydrofluoride and/or diisopropylethylamine trihydrofluoride) under conditions suitable for the complete deprotection of the molecule, and (d), purifying the deprotected oligonucleotide under conditions suitable for isolating the oligonucleotide.

In one embodiment, an oligonucleotide of the invention is chemically modified. Non-limiting examples of chemically modifications include 2'-deoxy-2'-fluoro, 2'-O-methyl, 2'-C-alkyl, 2'-deoxy, 2'-deoxy-2'-amino or LNA (locked nucleic acid) nucleosides; phosphorothioate internucleotide linkages; abasic moieties; or a terminal cap moiety at the 3'-end, 5'-end, or both 3' and 5' ends of the oligonucleotide. Non-limiting examples of chemically modified siRNA or siNA molecules are described in Table III herein and in Beigelman et al., U.S. Ser. No. 10/444,853, incorporated by reference herein in its entirety including the drawings.

By "column format" is meant, solid phase synthesis wherein the solid support (for example, CPG, polystyrene) is loaded into a retaining device comprising a column, cartridge, or equivalent, which allows the solid support to be sequentially exposed to reagents suitable for the synthesis of polymeric molecules, for example, oligonucleotides and their derivatives.

In an additional preferred embodiment, the process for deprotection of molecules comprising one or more ribonucleotides of the present invention is used to deprotect a molecule synthesized using a multi-well plate format. Specifically, the instant invention provides a high throughput deprotection of oligonucleotides in a multi-well plate format (for example, a 96-well plate or a 256 well plate). More specifically rapid deprotection of enzymatic nucleic acid molecules in greater than microgram quantities with high biological activity is featured. It has been determined that the recovery of enzymatically active nucleic acid molecules in high yield and quantity is dependent upon certain critical steps used during its deprotection.

In additional embodiments, the process for deprotection of molecules comprising one or more ribonucleotides of the present invention is used to deprotect a molecule synthesized in both a trityl-on and trityl-off manner.

By "trityl-on" is meant, a molecule, for example an oligonucleotide, synthesized in a manner which leaves the 5'-terminal dimethoxytrityl protecting group or an equivalent protecting group intact.

By "trityl-off" is meant, a molecule, for example an oligonucleotide, synthesized in a manner which removes the 5'-terminal dimethoxytrityl protecting group or an equivalent protecting group.

By "solid phase" is meant, synthesis comprising a solid support (for example, polystyrene or controlled pore glass) which is used as a scaffold for the sequential addition of subunits in the synthesis of a polymeric molecule such as an oligonucleotide. The solid support can be exposed sequentially to reagents in solution, thereby eliminating the need for repeated purification and isolation steps during synthesis. A linker molecule can be used as an interface between the solid support and the growing polymer. Solid phase synthesis can be used for both phosphoramidite and H-phosphonate methods of oligonucleotide synthesis.

By "solution phase" is meant, synthesis comprising the combining of reactants and reagents in solution, such as in a solvent which provides a homogenious mixture. Solution phase synthesis can be a preferred method for the synthesis of molecules in large quantities in consideration of lower costs, more efficient reactivity of reagents, and engineering factors.

By "hybrid phase" is meant, synthesis comprising both solid phase and solution phase synthesis elements.

The instant invention also features a large scale deprotection method of molecules comprising one or more ribonucleotides (for example, 3 mmol synthesis scale or greater). More specifically rapid deprotection of molecules comprising one or more ribonucleotides in greater than multigram or kilogram quantities with high biological activity is featured. It will be recognized by those skilled in the art that modifications concerning time and temperature parameters can be used to optimize deprotection conditions for reactions of differing scale and/or molecules of differing composition. The use of different time and temperature parameters for varying molecular content and/or different reaction scale applications is hence within the scope of the invention.

In a preferred embodiment, the invention features a method for the purification of nucleic acid molecules of the instant invention. Specifically, the invention features the use of ethanol or acetonitrile, with ethanol preferred, as an organic modifier in the purification of oligonucleotides with anion exchange chromatography. In an additional aspect, the instant invention features the use of ethanol as an organic modifier used in the purification of oligonucleotide molecules, including but not limited to short interfering RNA (siRNA), enzymatic nucleic acids, antisense nucleic acids, and/or aptamers. In another embodiment, the use of an organic modifier is not employed during large scale purification to avoid the use of organic solvents and a solution of about 20 mM sodium phosphate and about 0.1 M NaCl is used instead.

In additional embodiments, the media used for the purification of nucleic acid molecules of the instant invention comprises Pharmacia Source Q15 and Biorad Macroprep 25Q type media, or the equivalent thereof such as Pharmacia Q-sepharose, Perceptive POROS HQ, TOSOHAAS Q-5PW-HR, Q-5PW, or super Q-5PW. In another embodiment, the purification media is equilibrated with a buffer comprising about 20 mM sodium phosphate and about 0.1 M NaCl. In yet another embodiment, the purification media is equilibrated with a buffer comprising either 20% ethanol or acetonitrile in about 20 mM sodium phosphate and about 0.1 M NaCl.

In one embodiment, the invention features a loading buffer for oligonucleotide purification comprising about 20 mM sodium phosphate and about 0.1 M NaCl. In another embodiment, the invention features a loading buffer for oligonucleotide purification comprising either 20% ethanol or acetonitrile in about 20 mM sodium phosphate and about 0.1 M NaCl. In one aspect, the invention concerns applying a suitable gradient of about 1.0 M NaCl as an elution buffer for the purification of nucleic acid molecules of the instant invention. In another embodiment, the invention features the analysis of the fractions resulting from the purification process described herein, by a suitable technique (for example, UV, HPLC, and/or CGE), and allowing for the pure fractions to be pooled and desalted via tangential flow filtration or the equivalent thereof, by using membranes comprising such membranes as those selected from the group consisting of Sartorius or Pall Filtron PES 1 K membranes. In yet another preferred embodiment, the invention features the use of lyophilization as a means to concentrate the purified material.

In one embodiment, a method of purification of siRNA oligonucleotides of the invention further comprises the step of hybridizing two purified oligonucleotide strands together to form a siRNA duplex.

By "RNA" is meant a molecule comprising at least one ribonucleotide residue. By "ribonucleotide" is meant a nucleotide with a hydroxyl group at the 2' position of a β-D-ribofuranose moiety. The terms include double-stranded RNA, single-stranded RNA, isolated RNA such as partially purified RNA, essentially pure RNA, synthetic RNA, recombinantly produced RNA, as well as altered RNA that differs from naturally occurring RNA by the addition, deletion, substitution and/or alteration of one or more nucleotides. Such alterations can include addition of non-nucleotide material, such as to the end(s) of the siNA or internally, for example at one or more nucleotides of the RNA. Nucleotides in the RNA molecules of the instant invention can also comprise non-standard nucleotides, such as non-naturally occurring nucleotides or chemically synthesized nucleotides or deoxynucleotides. These altered RNAs can be referred to as analogs or analogs of naturally-occurring RNA. The RNA can be a siRNA, an enzymatic nucleic acid, antisense nucleic acid, decoy RNA, aptamer RNA, triplex forming oligonucleotide, chimeric RNA, 2-5A antisense chimera, agonist RNA, antagonist RNA, or any other RNA species. RNA can be used for purposes including but not limited to use as therapeutic agents, diagnostic reagents, and research reagents.

By "nucleic acid", "nucleic acid molecule" or "oligonucleotide" as used herein is meant a molecule having two or more nucleotides. The nucleic acid can be single, double, or multiple stranded and may comprise modified or unmodified nucleotides or non-nucleotides or various mixtures and combinations thereof.

In one embodiment, a process of the invention is used for the synthesis, deprotection, and purification of an enzymatic nucleic acid molecule, preferably in the hammerhead, AH ribozyme, NCH (Inozyme), G-cleaver, amberzyme, and/or zinzyme motif.

In one embodiment, a process of the invention is used for the synthesis, deprotection, and purification of a siRNA molecule.

In one embodiment, the synthesis of a double-stranded siRNA molecule of the invention, which can include one or more chemical modifications, comprises: (a) synthesis of two complementary strands of the siRNA molecule; (b) annealing the two complementary strands together under conditions suitable to obtain a double-stranded siRNA molecule. In another embodiment, synthesis of the two complementary strands of the siRNA molecule is by solid phase oligonucleotide synthesis. In yet another embodiment, synthesis of the two complementary strands of the siRNA molecule is by solid phase tandem oligonucleotide synthesis.

In one embodiment, the invention features a method for synthesizing a double-stranded siRNA duplex molecule comprising: (a) synthesizing a first oligonucleotide sequence strand of the siRNA molecule, wherein the first oligonucleotide sequence strand comprises a cleavable linker molecule that can be used as a scaffold for the synthesis of the second oligonucleotide sequence strand of the siRNA; (b) synthesizing the second oligonucleotide sequence strand of siRNA on the scaffold of the first oligonucleotide sequence strand, wherein the second oligonucleotide sequence strand further comprises a chemical moiety than can be used to purify the siRNA duplex; (c) cleaving the linker molecule of (a) under conditions suitable for the two siRNA oligonucleotide strands to hybridize and form a stable duplex; and (d) purifying the siRNA duplex utilizing the chemical moiety of the second oligonucleotide sequence strand. In one embodiment, cleavage of the linker molecule in (c) above takes place during deprotection of the oligonucleotide, for example under hydrolysis conditions using an alkylamine base such as methylamine. In one embodiment, the method of synthesis comprises solid phase synthesis on a solid support such as controlled pore glass (CPG) or polystyrene, wherein the first sequence of (a) is synthesized on a cleavable linker, such as a succinyl linker, using the solid support as a scaffold. The cleavable linker in (a) used as a scaffold for synthesizing the second strand can comprise similar reactivity as the solid support derivatized linker, such that cleavage of the solid support derivatized linker and the cleavable linker of (a) takes place concomitantly. In another embodiment, the chemical moiety of (b) that can be used to isolate the attached oligonucleotide sequence comprises a trityl group, for example a dimethoxytrityl group, which can be employed in a trityl-on synthesis strategy as described herein. In yet another embodiment, the chemical moiety, such as a dimethoxytrityl group, is removed during purification, for example, using acidic conditions.

In a further embodiment, the method for double-stranded siRNA synthesis is a solution phase synthesis or hybrid phase synthesis wherein both strands of the siRNA duplex are synthesized in tandem using a cleavable linker attached to the first sequence which acts a scaffold for synthesis of the second sequence. Cleavage of the linker under conditions suitable for hybridization of the separate siRNA sequence strands results in formation of the double-stranded siRNA molecule.

In another embodiment, the invention features a method for synthesizing a double-stranded siRNA duplex molecule comprising: (a) synthesizing one oligonucleotide sequence strand of the siRNA molecule, wherein the sequence comprises a cleavable linker molecule that can be used as a scaffold for the synthesis of another oligonucleotide sequence; (b) synthesizing a second oligonucleotide sequence having complementarity to the first sequence strand on the scaffold of (a), wherein the second sequence comprises the other strand of the double-stranded siRNA molecule and wherein the second sequence further comprises a chemical moiety than can be used to isolate the attached oligonucleotide sequence; (c) purifying the product of (b) utilizing the chemical moiety of the second oligonucleotide sequence strand under conditions suitable for isolating the full-length sequence comprising both siRNA oligonucleotide strands connected by the cleavable linker and under conditions suitable for the two siRNA oligonucleotide strands to hybridize and form a stable duplex. In one embodiment, cleavage of the linker molecule in (c) above takes place during deprotection of the oligonucleotide, for example under hydrolysis conditions. In another embodiment, cleavage of the linker molecule in (c) above takes place after deprotection of the oligonucleotide. In another embodiment, the method of synthesis comprises solid phase synthesis on a solid support such as controlled pore glass (CPG) or polystyrene, wherein the first sequence of (a) is synthesized on a cleavable linker, such as a succinyl linker, using the solid support as a scaffold. The cleavable linker in (a) used as a scaffold for synthesizing the second strand can comprise similar reactivity or differing reactivity as the solid support derivatized linker, such that cleavage of the solid support derivatized linker and the cleavable linker of (a) takes place either concomitantly or sequentially. In one embodiment, the chemical moiety of (b) that can be used to isolate the attached oligonucleotide sequence comprises a trityl group, for example a dimethoxytrityl group.

In another embodiment, the invention features a method for making a double-stranded siRNA molecule in a single synthetic process comprising: (a) synthesizing an oligonucleotide having a first and a second sequence, wherein the first sequence is complementary to the second sequence, and the first oligonucleotide sequence is linked to the second sequence via a cleavable linker, and wherein a terminal 5'-protecting group, for example, a 5'-O-dimethoxytrityl group (5'-O-DMT) remains on the oligonucleotide having the second sequence; (b) deprotecting the oligonucleotide whereby the deprotection results in the cleavage of the linker joining the two oligonucleotide sequences; and (c) purifying the product of (b) under conditions suitable for isolating the double-stranded siRNA molecule, for example using a trityl-on synthesis strategy as described herein.

The term "short interfering nucleic acid", "siNA", "short interfering RNA", "siRNA", "short interfering nucleic acid molecule", "short interfering oligonucleotide molecule", or "chemically-modified short interfering nucleic acid molecule" as used herein refers to any nucleic acid molecule capable of inhibiting or down regulating gene expression or viral replication, for example by mediating RNA interference "RNAi" or gene silencing in a sequence-specific manner; see for example Bass, 2001, *Nature*, 411, 428-429; Elbashir et al., 2001, *Nature*, 411, 494-498; and Kreutzer et al., International PCT Publication No. WO 00/44895; Zernicka-Goetz et al., International PCT Publication No. WO 01/36646; Fire, International PCT Publication No. WO 99/32619; Plaetinck et al., International PCT Publication No. WO 00/01846; Mello and Fire, International PCT Publication No. WO 01/29058; Deschamps-Depaillette, International PCT Publication No. WO 99/07409; and Li et al., International PCT Publication No. WO 00/44914; Allshire, 2002, *Science*, 297, 1818-1819; Volpe et al., 2002, *Science*, 297, 1833-1837; Jenuwein, 2002, *Science*, 297, 2215-2218; and Hall et al., 2002, *Science*, 297, 2232-2237; Hutvagner and Zamore, 2002, *Science*, 297, 2056-60; McManus et al., 2002, *RNA*, 8, 842-850; Reinhart et al., 2002, *Gene & Dev.*, 16, 1616-1626; and Reinhart & Bartel, 2002, *Science*, 297, 1831). Non limiting examples of siNA molecules of the invention are described in Beigelman et al., U.S. Ser. No. 10/444,853, incorporated by reference herein in its entirety including the drawings. For example the siNA can be a double-stranded polynucleotide molecule comprising self-complementary sense and antisense regions, wherein the antisense region comprises nucleotide sequence that is complementary to nucleotide sequence in a target nucleic acid molecule or a portion thereof and the sense region having nucleotide sequence corresponding to the target nucleic acid sequence or a portion thereof. The siNA can be assembled from two separate oligonucleotides, where one strand is the sense strand and the other is the antisense strand, wherein the antisense and sense strands are self-complementary (i.e. each strand comprises nucleotide sequence that is complementary to nucleotide sequence in the other strand; such as where the antisense strand and sense strand form a duplex or double stranded structure, for example wherein the double stranded region is about 19 base pairs); the antisense strand comprises nucleotide sequence that is complementary to nucleotide sequence in a target nucleic acid molecule or a portion thereof and the sense strand comprises nucleotide sequence corresponding to the target nucleic acid sequence or a portion thereof. Alternatively, the siNA is assembled from a single oligonucleotide, where the self-complementary sense and antisense regions of the siNA are linked by means of a nucleic acid based or non-nucleic acid-based linker(s). The siNA can be a polynucleotide with a duplex, asymmetric duplex, hairpin or asymmetric hairpin secondary structure, having self-complementary sense and antisense regions, wherein the antisense region comprises nucleotide sequence that is complementary to nucleotide sequence in a separate target nucleic acid molecule or a portion thereof and the sense region having nucleotide sequence corresponding to the target nucleic acid sequence or a portion thereof. The siNA can be a circular single-stranded polynucleotide having two or more loop structures and a stem comprising self-complementary sense and antisense regions, wherein the antisense region comprises nucleotide sequence that is complementary to nucleotide sequence in a target nucleic acid molecule or a portion thereof and the sense region having nucleotide sequence corresponding to the target nucleic acid sequence or a portion thereof, and wherein the circular polynucleotide can be processed either in vivo or in vitro to generate an active siNA molecule capable of mediating RNAi. The siNA can also comprise a single stranded polynucleotide having nucleotide sequence complementary to nucleotide sequence in a target nucleic acid molecule or a portion thereof (for example, where such siNA molecule does not require the presence within the siNA molecule of nucleotide sequence corresponding to the target nucleic acid sequence or a portion thereof), wherein the single stranded polynucleotide can further comprise a terminal phosphate group, such as a 5'-phosphate (see for example Martinez et al., 2002, *Cell.*, 110, 563-574 and Schwarz et al., 2002, *Molecular Cell*, 10, 537-568), or 5',3'-diphosphate. In certain embodiment, the siNA molecule of the invention comprises separate sense and antisense sequences or regions, wherein the sense and antisense regions are covalently linked by nucleotide or non-nucleotide linkers molecules as is known in the art, or are alternately non-covalently linked by ionic interactions, hydrogen bonding, van der waals interactions, hydrophobic interactions, and/or stacking interactions. In certain embodiments, the siNA molecules of the invention comprise nucleotide sequence that is complementary to nucleotide sequence of a target gene. In another embodiment, the siNA molecule of the invention interacts with nucleotide sequence of a target gene in a manner that causes inhibition of expression of the target gene. As used herein, siNA molecules need not be limited to those molecules containing only RNA, but further encompasses chemically-modified nucleotides and non-nucleotides. In certain embodiments, the short interfering nucleic acid molecules of the invention lack 2'-hydroxy (2'-OH) containing nucleotides. Applicant describes in certain embodiments short interfering nucleic acids that do not require the presence of nucleotides having a 2'-hydroxy group for mediating RNAi and as such, short interfering nucleic acid molecules of the invention optionally do not include any ribonucleotides (e.g., nucleotides having a 2'-OH group). Such siNA molecules that do not require the presence of ribonucleotides within the siNA molecule to support RNAi can however have an attached linker or linkers or other attached or associated groups, moieties, or chains containing one or more nucleotides with 2'-OH groups. Optionally, siNA molecules can comprise ribonucleotides at about 5, 10, 20, 30, 40, or 50% of the nucleotide positions. The modified short interfering nucleic acid molecules of the invention can also be referred to as short interfering modified oligonucleotides "siMON." As used herein, the term siNA is meant to be equivalent to other terms used to describe nucleic acid molecules that are capable of mediating sequence specific RNAi, for example short interfering RNA (siRNA), double-stranded RNA (dsRNA), micro-RNA (miRNA), short hairpin RNA (shRNA), short interfering oligonucleotide, short interfering nucleic acid, short interfering modified oligonucleotide, chemically-modified siRNA, post-transcriptional gene silencing RNA (ptgsRNA), and others. In addition, as used herein, the term RNAi is meant to be equivalent to other terms used to describe sequence specific RNA interference, such as post transcriptional gene silencing, translational inhibition, or epigenetics. For example, siNA molecules of the invention can be used to epigenetically silence genes at both the post-transcriptional level or the pre-transcriptional level. In a non-limiting example, epigenetic regulation of gene expression by siNA molecules of the invention can result from siNA mediated modification of chromatin structure to alter gene expression (see, for example, Allshire, 2002, *Science*, 297, 1818-1819; Volpe et al., 2002, *Science*, 297, 1833-1837; Jenuwein, 2002, *Science*, 297, 2215-2218; and Hall et al., 2002, *Science*, 297, 2232-2237).

By "asymmetric hairpin" as used herein is meant a linear siNA molecule comprising an antisense region, a loop portion that can comprise nucleotides or non-nucleotides, and a sense region that comprises fewer nucleotides than the antisense region to the extent that the sense region has enough complimentary nucleotides to base pair with the antisense region and form a duplex with loop. For example, an asymmetric hairpin siNA molecule of the invention can comprise an antisense region having length sufficient to mediate RNAi in a cell or in vitro system (e.g. about 19 to about 22 (e.g., about 19, 20, 21, or 22 nucleotides) and a loop region comprising about 4 to about 8 nucleotides, and a sense region having about 3 to about 18 (e.g., about 3, 4, 5, 6, 7, 8, 9, 10, 11, 12, 13, 14, 15, 16, 17, or 18) nucleotides that are complementary to the antisense region. The asymmetric hairpin siNA molecule can also comprise a 5'-terminal phosphate group that can be chemically modified. The loop portion of the asymmetric hairpin siNA molecule can comprise nucleotides, non-nucleotides, linker molecules, or conjugate molecules as described herein.

By "asymmetric duplex" as used herein is meant a siNA molecule having two separate strands comprising a sense region and an antisense region, wherein the sense region comprises fewer nucleotides than the antisense region to the extent that the sense region has enough complimentary nucleotides to base pair with the antisense region and form a duplex. For example, an asymmetric duplex siNA molecule of the invention can comprise an antisense region having length sufficient to mediate RNAi in a cell or in vitro system (e.g. about 19 to about 22 nucleotides) and a sense region having about 3 to about 18 nucleotides that are complementary to the antisense region.

By "enzymatic nucleic acid molecule" it is meant a nucleic acid molecule that has complementarity in a substrate binding region to a specified gene target, and also has an enzymatic activity which is active to specifically cleave target RNA. That is, the enzymatic nucleic acid molecule is able to intermolecularly cleave RNA and thereby inactivate a target RNA molecule. These complementary regions allow sufficient hybridization of the enzymatic nucleic acid molecule to the target RNA and thus permit cleavage. One hundred percent complementarity is preferred, but complementarity as low as 50-75% may also be useful in this invention. The nucleic acids may be modified at the base, sugar, and/or phosphate groups. The term enzymatic nucleic acid is used interchangeably with phrases such as ribozymes, catalytic RNA, enzymatic RNA, catalytic DNA, aptazyme or aptamer-binding ribozyme, regulatable ribozyme, catalytic oligonucleotides, nucleozyme, DNAzyme, RNA enzyme, endoribonuclease, endonuclease, minizyme, leadzyme, oligozyme or DNA enzyme. All of these terminologies describe nucleic acid molecules with enzymatic activity. The specific enzymatic nucleic acid molecules described in the instant application are not meant to be limiting and those skilled in the art will recognize that all that is important in an enzymatic nucleic acid molecule of this invention is that it have a specific substrate binding site which is complementary to one or more of the target nucleic acid regions, and that it have nucleotide sequences within or surrounding that substrate binding site which impart a nucleic acid cleaving activity to the molecule (Cech et al., U.S. Pat. No. 4,987,071; Cech et al., 1988, JAMA).

By "antisense nucleic acid" it is meant a non-enzymatic nucleic acid molecule that binds to target RNA by means of RNA-RNA or RNA-DNA or RNA-PNA (protein nucleic acid; Egholm et al., 1993 Nature 365, 566) interactions and alters the activity of the target RNA (for a review see Stein and Cheng, 1993 Science 261, 1004). Typically, antisense molecules will be complementary to a target sequence along a single contiguous sequence of the antisense molecule. However, in certain embodiments, an antisense molecule may bind to substrate such that the substrate molecule forms a loop, and/or an antisense molecule may bind such that the antisense molecule forms a loop. Thus, the antisense molecule may be complementary to two (or even more) non-contiguous substrate sequences or two (or even more) non-contiguous sequence portions of an antisense molecule may be complementary to a target sequence or both.

By "AH ribozyme" motif is meant, an enzymatic nucleic acid molecule comprising a motif as described in Kore et al., 1998, *Nucleic Acids Research*, 26(18), 4116-4120.

By "NCH" or "Inozyme" motif is meant, an enzymatic nucleic acid molecule comprising a motif as described in Ludwig et al., U.S. Ser. No. 09/406,643, filed Sep. 27, 1999, entitled "COMPOSITIONS HAVING RNA CLEAVING ACTIVITY", and International PCT publication Nos. WO 98/58058 and WO 98/58057, all incorporated by reference herein in their entirety including the drawings.

By "G-cleaver" motif is meant, an enzymatic nucleic acid molecule comprising a motif as described in Eckstein et al., International PCT publication No. WO 99/16871, incorporated by reference herein in its entirety including the drawings.

By "zinzyme" motif is meant, a class II enzymatic nucleic acid molecule comprising a motif as described in Beigelman et al., International PCT publication No. WO 99/55857, incorporated by reference herein in its entirety including the drawings. Zinzymes represent a non-limiting example of an enzymatic nucleic acid molecule that does not require a ribonucleotide (2'-OH) group within its own nucleic acid sequence for activity.

By "amberzyme" motif is meant, a class I enzymatic nucleic acid molecule comprising a motif as described in Beigelman et al., International PCT publication No. WO 99/55857, incorporated by reference herein in its entirety including the drawings. Amberzymes represent a non-limiting example of an enzymatic nucleic acid molecule that does not require a ribonucleotide (2'-OH) group within its own nucleic acid sequence for activity.

By "2-5A antisense chimera" it is meant, an antisense oligonucleotide containing a 5' phosphorylated 2'-5'-linked adenylate residues. These chimeras bind to target RNA in a sequence-specific manner and activate a cellular 2-5A-dependent ribonuclease which, in turn, cleaves the target RNA (Torrence et al., 1993 *Proc. Natl. Acad. Sci. USA* 90, 1300).

By "triplex forming oligonucleotide" it is meant an oligonucleotide that can bind to a double-stranded DNA in a sequence-specific manner to form a triple-strand helix. Formation of such triple helix structure has been shown to inhibit transcription of the targeted gene (Duval-Valentin et al., 1992 *Proc. Natl. Acad. Sci. USA* 89, 504).

By "decoy RNA" is meant an RNA molecule that mimics the natural binding domain for a ligand. The decoy RNA therefore competes with natural binding target for the binding of a specific ligand. For example, it has been shown that over-expression of HIV trans-activation response (TAR) RNA can act as a "decoy" and efficiently binds HIV tat protein, thereby preventing it from binding to TAR sequences encoded in the HIV RNA (Sullenger et al., 1990, *Cell*, 63, 601-608). This is meant to be a specific example. Those in the art will recognize that this is but one example, and other embodiments can be readily generated using techniques generally known in the art.

By "agonist RNA" is meant an RNA molecule that can bind to protein receptors with high affinity and cause the stimulation of specific cellular pathways.

By "antagonist RNA" is meant an RNA molecule that can bind to cellular proteins and prevent it from performing its normal biological function (for example, see Tsai et al., 1992 *Proc. Natl. Acad. Sci. USA* 89, 8864-8868).

By "aptamer" or "nucleic acid aptamer" as used herein is meant a nucleic acid molecule that binds specifically to a target molecule wherein the nucleic acid molecule has sequence that comprises a sequence recognized by the target molecule in its natural setting. Alternately, an aptamer can be a nucleic acid molecule that binds to a target molecule where the target molecule does not naturally bind to a nucleic acid. The target molecule can be any molecule of interest. For example, the aptamer can be used to bind to a ligand-binding domain of a protein, thereby preventing interaction of the naturally occurring ligand with the protein. This is a non-limiting example and those in the art will recognize that other embodiments can be readily generated using techniques generally known in the art. (See, for example, Gold et al., 1995, *Annu. Rev. Biochem.*, 64, 763; Brody and Gold, 2000, *J. Biotechnol.*, 74, 5; Sun, 2000, *Curr. Opin. Mol. Ther.*, 2, 100; Kusser, 2000, *J. Biotechnol.*, 74, 27; Hermann and Patel, 2000, *Science*, 287, 820; and Jayasena, 1999, *Clinical Chemistry*, 45, 1628).

By "comprising" is meant including, but not limited to, whatever follows the word "comprising". Thus, use of the term "comprising" indicates that the listed elements are required or mandatory, but that other elements are optional and may or may not be present. By "consisting of" is meant including, and limited to, whatever follows the phrase "consisting of". Thus, the phrase "consisting of" indicates that the listed elements are required or mandatory, and that no other elements may be present. By "consisting essentially of" is meant including any elements listed after the phrase, and limited to other elements that do not interfere with or contribute to the activity or action specified in the disclosure for the listed elements. Thus, the phrase "consisting essentially of" indicates that the listed elements are required or mandatory, but that other elements are optional and may or may not be present depending upon whether or not they affect the activity or action of the listed elements.

Other features and advantages of the invention will be apparent from the following description of the preferred embodiments thereof, and from the claims.

BRIEF DESCRIPTION OF THE DRAWINGS

The drawings will first briefly be described.

Drawings:

FIG. 1 is a schematic representation of a one pot deprotection of nucleic acid molecules comprising one or more ribonucleotides synthesized using the phosphoramidite approach.

FIG. 2 is schematic representation of incomplete N-phthaloyl deprotection products. Compound A represents intact N-phthaloyl protection, compound B represents partially cleaved N-phthaloyl protection, and compound C represents a free 2'-amino group after complete cleavage of N-phthaloyl protection.

FIG. 3 shows a comparison of different one pot deprotection methods based on electrospray mass spectrometry (ESMS) data. FIG. 3A shows a ESMS chromatogram of a purified full length oligonucleotide containing ribonucleotide functions (TBDMS protection) and two 2'-amino functions (N-phthaloyl protection) following a deprotection method which utilized anhydrous methylamine/DMSO/TEA.3HF. FIG. 3B shows a ESMS chromatogram of a purified full length oligonucleotide containing ribonucleotide functions (TBDMS protection) and two 2'-amino functions (N-phthaloyl protection) following a deprotection method which utilized aqueous methylamine/DMSO/TEA.3HF. The three peaks seen in FIG. 3A represents the masses of the fully deprotected oligo, the deprotected oligo with one partially deprotected phthaloyl group intact, and the deprotected oligo with two partially deprotected phthaloyl groups intact. The single peak shown in FIG. 3B represents the mass of the fully deprotected oligo only.

FIG. 4 shows a comparison of different one pot deprotection methods based on capillary gel electrophoresis data. FIG. 4A shows a CE chromatogram of the purified full length oligonucleotide shown in FIG. 3A, which results in a broad peak due to partially cleaved phthaloyl group contaminants. FIG. 4B shows a CE chromatogram of the purified full length oligonucleotide shown in FIG. 3B, which results in a single narrow peak consistent with a homogenous oligonucleotide species.

FIG. 5 shows a non-limiting example of a scheme for the synthesis of double-stranded siNA molecules. The complementary siNA sequence strands, strand 1 and strand 2, are synthesized in tandem and are connected by a cleavable linkage, such as a nucleotide succinate or abasic succinate, which can be the same or different from the cleavable linker used for solid phase synthesis on a solid support. The synthesis can be either solid phase or solution phase, in the example shown, the synthesis is a solid phase synthesis. The synthesis is performed such that a protecting group, such as a dimethoxytrityl group, remains intact on the terminal nucleotide of the tandem oligonucleotide. Upon cleavage and deprotection of the oligonucleotide, the two siNA strands spontaneously hybridize to form a siNA duplex, which allows the purification of the duplex by utilizing the properties of the terminal protecting group, for example by applying a trityl on purification method wherein only duplexes/oligonucleotides with the terminal protecting group are isolated.

DETAILED DESCRIPTION OF THE INVENTION

Figure 6:
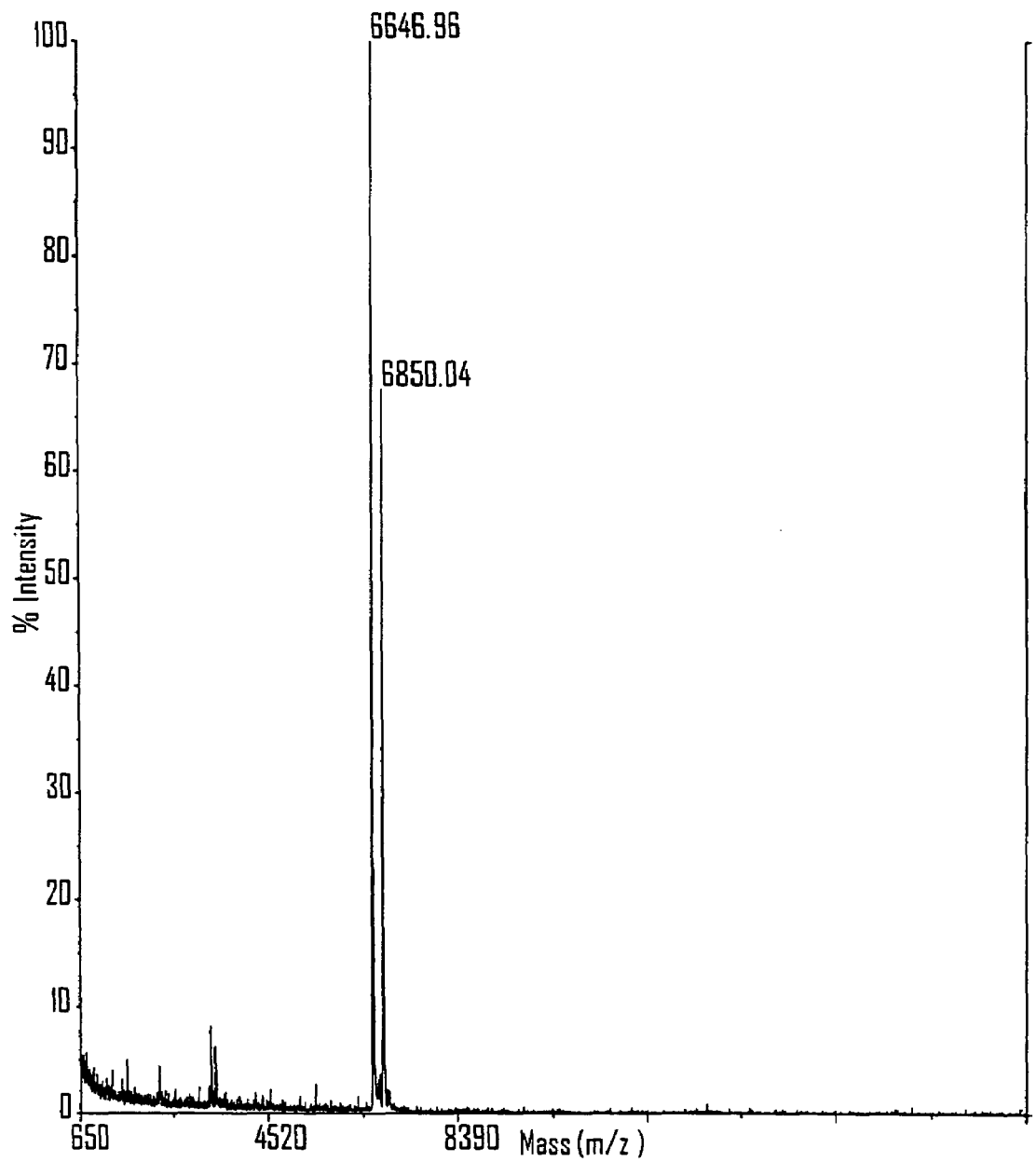
FIG. 6 shows a MALDI-TOF mass spectrum of a purified double-stranded siNA duplex synthesized by a method of the invention. The two peaks shown correspond to the predicted mass of the separate siNA sequence strands. This result demonstrates that the siNA duplex generated from tandem synthesis can be purified as a single entity using a simple trityl-on purification methodology.
Figure 7:
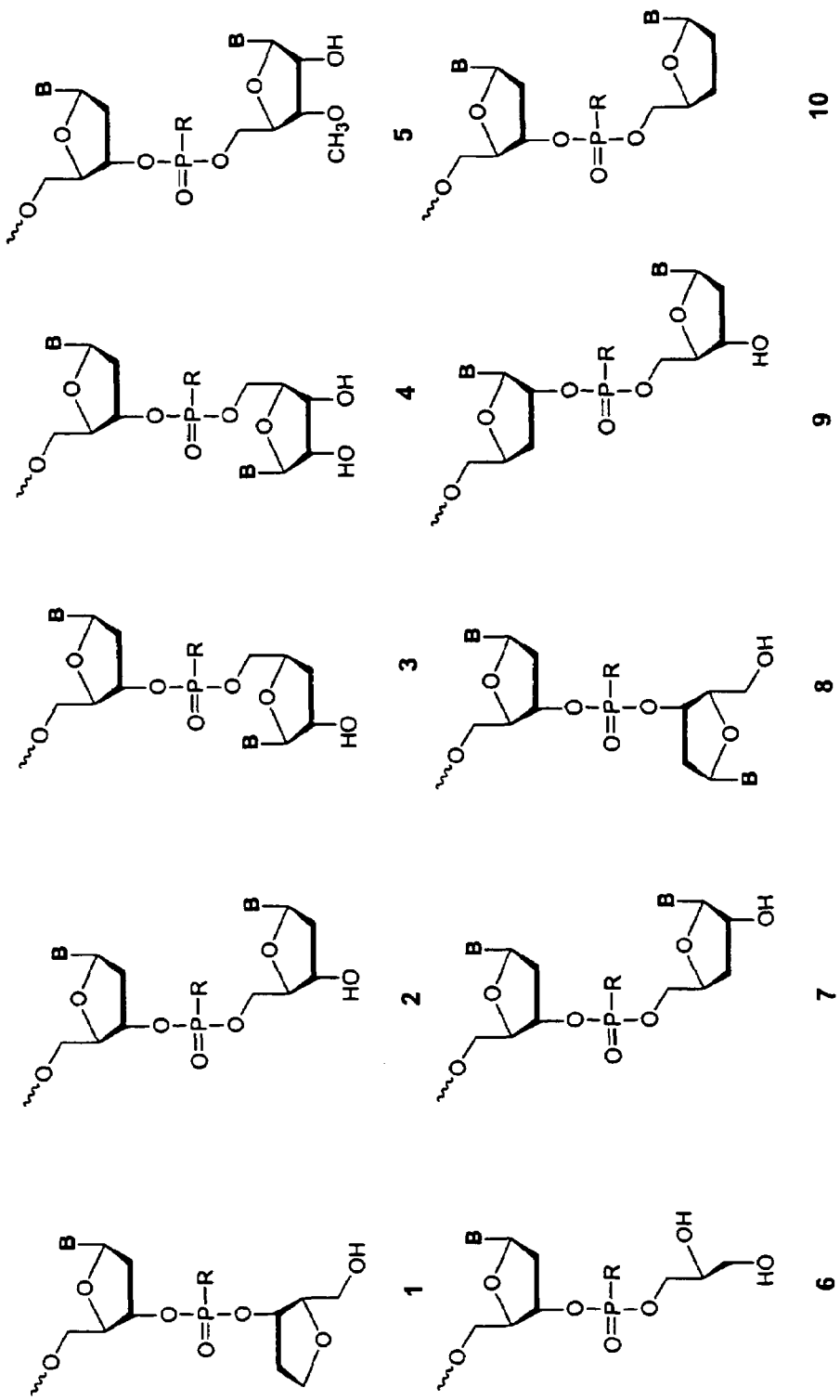
FIG. 7 shows non-limiting examples of different stabilization chemistries (1-10) that can be used, for example, to stabilize the 3'-end of siNA sequences of the invention, including (1) [3-3']-inverted deoxyribose; (2) deoxyribonucleotide; (3) [5'-3']-3'-deoxyribonucleotide; (4) [5'-3']-ribonucleotide; (5) [5'-3']-3'-O-methyl ribonucleotide; (6) 3'-glyceryl; (7) [3'-5']-3'-deoxyribonucleotide; (8) [3'-3']-deoxyribonucleotide; (9) [5'-2']-deoxyribonucleotide; and (10) [5-3']-dideoxyribonucleotide. In addition to modified and unmodified backbone chemistries indicated in the figure, these chemistries can be combined with different backbone modifications as described herein, for example, backbone modifications having Formula I. In addition, the 2'-deoxy nucleotide shown 5' to the terminal modifications shown can be another modified or unmodified nucleotide or non-nucleotide.

Nucleic Acid Molecule Mediating RNA Interference (RNAi)

RNA interference refers to the process of sequence specific post-transcriptional gene silencing in animals mediated by short interfering RNAs (siRNAs) (Fire et al., 1998, *Nature*, 391, 806). The corresponding process in plants is commonly referred to as post-transcriptional gene silencing or RNA silencing and is also referred to as quelling in fungi. The process of post-transcriptional gene silencing is thought to be an evolutionarily-conserved cellular defense mechanism used to prevent the expression of foreign genes which is commonly shared by diverse flora and phyla (Fire et al., 1999, *Trends Genet.*, 15, 358). Such protection from foreign gene expression may have evolved in response to the production of double-stranded RNAs (dsRNAs) derived from viral infection or the random integration of transposon elements into a host genome via a cellular response that specifically destroys homologous single-stranded RNA or viral genomic RNA. The presence of dsRNA in cells triggers the RNAi response though a mechanism that has yet to be fully characterized. This mechanism appears to be different from the interferon response that results from dsRNA-mediated activation of protein kinase PKR and 2', 5'-oligoadenylate synthetase resulting in non-specific cleavage of mRNA by ribonuclease L.

The presence of long dsRNAs in cells stimulates the activity of a ribonuclease III enzyme referred to as Dicer. Dicer is involved in the processing of the dsRNA into short pieces of dsRNA known as short interfering RNAs (siRNAs) (Berstein et al., 2001, *Nature*, 409, 363). Short interfering RNAs derived from Dicer activity are typically about 21 to about 23 nucleotides in length and comprise about 19 base pair duplexes. Dicer has also been implicated in the excision of 21- and 22-nucleotide small temporal RNAs (stRNAs) from precursor RNA of conserved structure that are implicated in translational control (Hutvagner et al., 2001, *Science*, 293, 834). The RNAi response also features an endonuclease complex containing a siRNA, commonly referred to as an RNA-induced silencing complex (RISC), which mediates cleavage of single-stranded RNA having sequence homologous to the siRNA. Cleavage of the target RNA takes place in the middle of the region complementary to the guide sequence of the siRNA duplex (Elbashir et al., 2001, *Genes Dev.*, 15, 188). In addition, RNA interference can also involve small RNA (e.g., micro-RNA or miRNA) mediated gene silencing, presumably though cellular mechanisms that regulate chromatin structure and thereby prevent transcription of target gene sequences (see for example Allshire, 2002, *Science*, 297, 1818-1819; Volpe et al., 2002, *Science*, 297, 1833-1837; Jenuwein, 2002, *Science*, 297, 2215-2218; and Hall et al., 2002, *Science*, 297, 2232-2237). As such, siNA molecules of the invention can be used to mediate gene silencing via interaction with RNA transcripts or alternately by interaction with particular gene sequences, wherein such interaction results in gene silencing either at the transcriptional level or post-transcriptional level.

RNAi has been studied in a variety of systems. Fire et al., 1998, *Nature*, 391, 806, were the first to observe RNAi in *C. elegans*. Wianny and Goetz, 1999, *Nature Cell Biol.*, 2, 70, describe RNAi mediated by dsRNA in mouse embryos. Hammond et al., 2000, *Nature*, 404, 293, describe RNAi in *Drosophila* cells transfected with dsRNA. Elbashir et al., 2001, *Nature*, 411, 494, describe RNAi induced by introduction of duplexes of synthetic 21-nucleotide RNAs in cultured mammalian cells including human embryonic kidney and HeLa cells. Recent work in *Drosophila* embryonic lysates has revealed certain requirements for siRNA length, structure, chemical composition, and sequence that are essential to mediate efficient RNAi activity. These studies have shown that 21 nucleotide siRNA duplexes are most active when containing two 2-nucleotide 3'-terminal nucleotide overhangs. Furthermore, substitution of one or both siRNA strands with 2'-deoxy or 2'-O-methyl nucleotides abolishes RNAi activity, whereas substitution of 3'-terminal siRNA nucleotides with deoxy nucleotides was shown to be tolerated. Mismatch sequences in the center of the siRNA duplex were also shown to abolish RNAi activity. In addition, these studies also indicate that the position of the cleavage site in the target RNA is defined by the 5'-end of the siRNA guide sequence rather than the 3'-end (Elbashir et al., 2001, *EMBO J.*, 20, 6877). Other studies have indicated that a 5'-phosphate on the target-complementary strand of a siRNA duplex is required for siRNA activity and that ATP is utilized to maintain the 5'-phosphate moiety on the siRNA (Nykanen et al., 2001, *Cell*, 107, 309); however, siRNA molecules lacking a 5'-phosphate are active when introduced exogenously, suggesting that 5'-phosphorylation of siRNA constructs may occur in vivo. The term short interfering RNA (siRNA) is used interchangeably with the terms short interfering nucleic acid (siNA), double-stranded RNA (dsRNA), micro-RNA (miRNA), and short hairpin RNA (shRNA), all of which are molecules capable of mediating RNA interference (RNAi)

Enzymatic Nucleic Acid Molecules:

The enzymatic RNA molecule is a nucleic acid molecule comprising one or more ribonucleotides. Enzymatic RNA molecule is able to intramolecularly or intermolecularly cleave RNA or DNA and thereby inactivate a target RNA or DNA molecule. The enzymatic RNA acid molecule that has complementarity in a substrate binding region to a specified gene target, also has an enzymatic activity that specifically cleaves RNA or DNA in that target. This complementarity functions to allow sufficient hybridization of the enzymatic RNA molecule to the target RNA or DNA to allow the cleavage to occur. 100% Complementarity is preferred, but complementarity as low as 50-75% may also be useful in this invention. The nucleic acids may be modified at the base, sugar, and/or phosphate groups.

The term enzymatic RNA acid is used interchangeably with phrases such as ribozymes, enzymatic nucleic acid, catalytic RNA, enzymatic RNA, nucleozyme, RNA enzyme, endoribonuclease, minizyme, leadzyme, oligozyme and the like.

By "complementarity" is meant a nucleic acid that can form hydrogen bond(s) with other RNA sequence by either traditional Watson-Crick or other non-traditional types (for example, Hoogsteen type) of base-paired interactions.

RNA molecules having an endonuclease enzymatic activity are able to repeatedly cleave other separate RNA molecules in a nucleotide base sequence-specific manner. Such enzymatic RNA molecules can be targeted to virtually any RNA transcript, and efficient cleavage achieved in vitro (Zaug et al., 324, *Nature* 429 1986; Kim et al., 84 *Proc. Natl. Acad. Sci. USA* 8788, 1987; Haseloff and Gerlach, 334 *Nature* 585, 1988; Cech, 260 *JAMA* 3030, 1988; and Jefferies et al., 17 *Nucleic Acids Research* 1371, 1989).

Because of their sequence-specificity, trans-cleaving ribozymes show promise as therapeutic agents for human disease (Usman & McSwiggen, 1995 *Ann. Rep. Med. Chem.* 30, 285-294; Christoffersen and Marr, 1995 *J. Med. Chem.* 38, 2023-2037). Ribozymes can be designed to cleave specific RNA targets within the background of cellular RNA. Such a cleavage event renders the mRNA non-functional and abrogates protein expression from that RNA. In this manner, synthesis of a protein associated with a disease state can be selectively inhibited.

Seven basic varieties of naturally-occurring enzymatic RNAs are known presently. Each can catalyze the hydrolysis of RNA phosphodiester bonds in trans (and thus can cleave other RNA molecules) under physiological conditions. In general, enzymatic RNA act by first binding to a target RNA. Such binding occurs through the target binding portion of a enzymatic nucleic acid which is held in close proximity to an enzymatic portion of the molecule that acts to cleave the target RNA. Thus, the enzymatic nucleic acid first recognizes and then binds a target RNA through complementary base-pairing, and once bound to the correct site, acts enzymatically to cut the target RNA. Strategic cleavage of such a target RNA will destroy its ability to direct synthesis of an encoded protein. After an enzymatic nucleic acid has bound and cleaved its RNA target, it is released from that RNA to search for another target and can repeatedly bind and cleave new targets. In addition, several in vitro selection (evolution) strategies (Orgel, 1979, *Proc. R. Soc. London, B* 205, 435) have been used to evolve new nucleic acid catalysts capable of catalyzing cleavage and ligation of phosphodiester linkages (Joyce, 1989, *Gene*, 82, 83-87; Beaudry et al., 1992, *Science* 257, 635-641; Joyce, 1992, *Scientific American* 267, 90-97; Breaker et al., 1994, *TIBTECH* 12, 268; Bartel et al., 1993, *Science* 261:1411-1418; Szostak, 1993, *TIBS* 17, 89-93; Kumar et al., 1995, *FASEB J.*, 9, 1183; Breaker, 1996, *Curr. Op. Biotech.*, 7, 442; Santoro et al., 1997, *Proc. Natl. Acad. Sci.*, 94, 4262; Tang et al., 1997, *RNA* 3, 914; Nakamaye & Eckstein, 1994, supra; Long & Uhlenbeck, 1994, supra; Ishizaka et al., 1995, supra; Vaish et al., 1997, *Biochemistry* 36, 6495; all of these are incorporated by reference herein). Each can catalyze a series of reactions including the hydrolysis of phosphodiester bonds in trans (and thus can cleave other RNA molecules) under physiological conditions.

The enzymatic nature of a ribozyme has significant advantages, such as the concentration of ribozyme necessary to affect a therapeutic treatment is lower. This advantage reflects the ability of the ribozyme to act enzymatically. Thus, a single ribozyme molecule is able to cleave many molecules of target RNA. In addition, the ribozyme is a highly specific inhibitor, with the specificity of inhibition depending not only on the base-pairing mechanism of binding to the target RNA, but also on the mechanism of target RNA cleavage. Single mismatches, or base-substitutions, near the site of cleavage can be chosen to completely eliminate catalytic activity of a ribozyme.

Nucleic acid molecules having an endonuclease enzymatic activity are able to repeatedly cleave other separate RNA molecules in a nucleotide base sequence-specific manner. Such enzymatic nucleic acid molecules can be targeted to virtually any RNA transcript, and achieve efficient cleavage in vitro (Zaug et al., 324, *Nature* 429 1986; Uhlenbeck, 1987 *Nature* 328, 596; Kim et al., 84 *Proc. Natl. Acad. Sci. USA* 8788, 1987; Dreyfus, 1988, *Einstein Quart. J. Bio. Med.*, 6, 92; Haseloff and Gerlach, 334 *Nature* 585, 1988; Cech, 260 *JAMA* 3030, 1988; and Jefferies et al., 17 *Nucleic Acids Research* 1371, 1989; Santoro et al., 1997 supra).

Because of their sequence specificity, trans-cleaving ribozymes show promise as therapeutic agents for human disease (Usman & McSwiggen, 1995 *Ann. Rep. Med. Chem.* 30, 285-294; Christoffersen and Marr, 1995 *J. Med. Chem.* 38, 2023-2037). Ribozymes can be designed to cleave specific RNA targets within the background of cellular RNA. Such a cleavage event renders the RNA non-functional and abrogates protein expression from that RNA. In this manner, synthesis of a protein associated with a disease state can be selectively inhibited (Warashina et al., 1999, *Chemistry and Biology*, 6, 237-250).

In one aspect, enzymatic nucleic acid molecules are formed in a hammerhead or hairpin motif, but may also be formed in the motif of a hepatitis delta virus (HDV), group I intron, RNaseP RNA (in association with an external guide sequence) or *Neurospora* VS RNA. Examples of such hammerhead motifs are described by Rossi et al., 1992, *Aids Research and Human Retroviruses* 8, 183; Usman et al., 1996, *Curr. Op. Struct. Biol.*, 1, 527; of hairpin motifs by Hampel et al., EP 0360257; Hampel and Tritz, 1989 *Biochemistry* 28, 4929; and Hampel et al., 1990 *Nucleic Acids Res.* 18, 299; Chowrira et al., U.S. Pat. No. 5,631,359; an example of the hepatitis delta virus motif is described by Perrotta and Been, 1992 *Biochemistry* 31, 16; Been et al., U.S. Pat. No. 5,625,047; of the RNaseP motif by Guerrier-Takada et al., 1983 *Cell* 35, 849; Forster and Altman, 1990 *Science* 249, 783; *Neurospora* VS RNA ribozyme motif is described by Collins (Saville and Collins, 1990 *Cell* 61, 685-696; Saville and Collins, 1991 *Proc. Natl. Acad. Sci. USA* 88, 8826-8830; Guo and Collins, 1995 *EMBO J.* 14, 368) and of the Group I intron by Zaug et al., 1986, *Nature*, 324, 429; Cech et al., U.S. Pat. No. 4,987,071. These specific motifs are not limiting in the invention and those skilled in the art will recognize that all that is important in an enzymatic nucleic acid molecule with endonuclease activity of this invention is that it has a specific substrate binding site which is complementary to one or more of the target gene RNA and that it have nucleotide sequences within or surrounding that substrate binding site which impart an RNA cleaving activity to the molecule. The length of the binding site varies for different ribozyme motifs, and a person skilled in the art will recognize that to achieve an optimal ribozyme activity the length of the binding arm should be of sufficient length to form a stable interaction with the target nucleic acid sequence.

Catalytic activity of the ribozymes described in the instant invention can be optimized as described by Draper et al., supra. The details will not be repeated here, but include altering the length of the ribozyme binding arms, or chemically synthesizing ribozymes with modifications (base, sugar and/or phosphate) that prevent their degradation by serum ribonucleases and/or enhance their enzymatic activity (see e.g., Eckstein et al., International Publication No. WO 92/07065; Perrault et al., 1990 *Nature* 344, 565; Pieken et al., 1991 *Science* 253, 314; Usman and Cedergren, 1992 *Trends in Biochem. Sci.* 17, 334; Usman et al., International Publication No. WO 93/15187; and Rossi et al., International Publication No. WO 91/03162; Sproat, U.S. Pat. No. 5,334,711; and Burgin et al., supra; all of these describe various chemical modifications that can be made to the base, phosphate and/or sugar moieties of enzymatic RNA molecules). Modifications which enhance their efficacy in cells, and removal of bases from stem loop structures to shorten RNA synthesis times and reduce chemical requirements are desired. (All these publications are hereby incorporated by reference herein).

Aptamers:

Nucleic acid aptamers can be selected to specifically bind to a particular ligand of interest (see for example Gold et al., U.S. Pat. No. 5,567,588 and U.S. Pat. No. 5,475,096, Gold et al., 1995, *Annu. Rev. Biochem.*, 64, 763; Brody and Gold, 2000, *J. Biotechnol.*, 74, 5; Sun, 2000, *Curr. Opin. Mol. Ther.*, 2, 100; Kusser, 2000, *J. Biotechnol.*, 74, 27; Hermann and Patel, 2000, *Science*, 287, 820; and Jayasena, 1999, *Clinical Chemistry*, 45, 1628). For example, the use of in vitro selection can be applied to evolve nucleic acid aptamers with binding specificity for HIV envelope glycoprotein gp41, gp120 or to any other portion of HIV that disrupts fusogenic activity of the virus. Nucleic acid aptamers can include chemical modifications and linkers as described herein. Nucleic apatmers of the invention can be double stranded or single stranded and can comprise one distinct nucleic acid sequence or more than one nucleic acid sequences complexed with one another. Aptamer molecules of the invention that bind to HIV envelope glycoprotein, for example gp41, can modulate the fusogenic activity of HIV and therefore modulate cell entry and infectivity of the virus.

Antisense:

Antisense molecules can be modified or unmodified RNA, DNA, or mixed polymer oligonucleotides and primarily function by specifically binding to matching sequences resulting in modulation of peptide synthesis (Wu-Pong, November 1994, *BioPharm*, 20-33). The antisense oligonucleotide binds to target RNA by Watson Crick base-pairing and blocks gene expression by preventing ribosomal translation of the bound sequences either by steric blocking or by activating RNase H enzyme. Antisense molecules may also alter protein synthesis by interfering with RNA processing or transport from the nucleus into the cytoplasm (Mukhopadhyay & Roth, 1996, *Crit. Rev. in Oncogenesis* 7, 151-190).

In addition, binding of single stranded DNA to RNA may result in nuclease degradation of the heteroduplex (Wu-Pong, supra; Crooke, supra). To date, the only backbone modified DNA chemistry which will act as substrates for RNase H are phosphorothioates, phosphorodithioates, and borontrifluoridates. Recently, it has been reported that 2'-arabino and 2'-fluoro arabino-containing oligos can also activate RNase H activity.

A number of antisense molecules have been described that utilize novel configurations of chemically modified nucleotides, secondary structure, and/or RNase H substrate domains (Woolf et al., U.S. Pat. No. 5,989,912; Thompson et al., U.S. Ser. No. 60/082,404 which was filed on Apr. 20, 1998; Hartmann et al., U.S. Ser. No. 60/101,174 which was filed on Sep. 21, 1998) all of these are incorporated by reference herein in their entirety.

Antisense DNA can be used to target RNA by means of DNA-RNA interactions, thereby activating RNase H, which digests the target RNA in the duplex. Antisense DNA can be chemically synthesized or can be expressed via the use of a single stranded DNA intracellular expression vector or the equivalent thereof.

Chemically synthesizing nucleic acid molecules with modifications (base, sugar and/or phosphate) that prevent their degradation by serum ribonucleases can increase their potency (see e.g., Eckstein et al., International Publication No. WO 92/07065; Perrault et al., 1990 *Nature* 344, 565; Pieken et al., 1991, *Science* 253, 314; Usman and Cedergren, 1992, *Trends in Biochem. Sci.* 17, 334; Usman et al., International Publication No. WO 93/15187; Rossi et al., International Publication No. WO 91/03162; Sproat, U.S. Pat. No. 5,334,711; and Burgin et al., supra; all of these describe various chemical modifications that can be made to the base, phosphate and/or sugar moieties of the nucleic acid molecules described herein. All these references are incorporated by reference herein. Modifications which enhance their efficacy in cells, and removal of bases from nucleic acid molecules to shorten oligonucleotide synthesis times and reduce chemical requirements are desired.

There are several examples in the art describing sugar, base and phosphate modifications that can be introduced into nucleic acid molecules with significant enhancement in their nuclease stability and efficacy. For example, oligonucleotides are modified to enhance stability and/or enhance biological activity by modification with nuclease resistant groups, for example, 2'-amino, 2'-C-allyl, 2'-flouro, 2'-O-methyl, 2'-H, nucleotide base modifications (for a review see Usman and Cedergren, 1992, *TIBS.* 17, 34; Usman et al., 1994, *Nucleic Acids Symp. Ser.* 31, 163; Burgin et al., 1996, *Biochemistry*, 35, 14090). Sugar modifications of nucleic acid molecules have been extensively described in the art (see Eckstein et al., International Publication PCT No. WO 92/07065; Perrault et al. *Nature*, 1990, 344, 565-568; Pieken et al. *Science*, 1991, 253, 314-317; Usman and Cedergren, *Trends in Biochem. Sci.*, 1992, 17, 334-339; Usman et al. International Publication PCT No. WO 93/15187; Sproat, U.S. Pat. No. 5,334,711 and Beigelman et al., 1995, *J. Biol. Chem.*, 270, 25702; Beigelman et al., International PCT publication No. WO 97/26270; Beigelman et al., U.S. Pat. No. 5,716,824; Usman et al., U.S. Pat. No. 5,627,053; Woolf et al., International PCT Publication No. WO 98/13526; Thompson et al., U.S. Ser. No. 60/082,404 which was filed on Apr. 20, 1998; Karpeisky et al., 1998, *Tetrahedron Lett.*, 39, 1131; Earnshaw and Gait, 1998, *Biopolymers (Nucleic acid Sciences)*, 48, 39-55; Verma and Eckstein, 1998, *Annu. Rev. Biochem.*, 67, 99-134; and Burlina et al., 1997, *Bioorg. Med. Chem.*, 5, 1999-2010; all of the references are hereby incorporated by reference herein in their totalities). Such publications describe general methods and strategies to determine the location of incorporation of sugar, base and/or phosphate modifications and the like into ribozymes without inhibiting catalysis. In view of such teachings, similar modifications can be used as described herein to modify the nucleic acid molecules of the instant invention.

While chemical modification of oligonucleotide internucleotide linkages with phosphorothioate, phosphorothioate, and/or 5'-methylphosphonate linkages improves stability, too many of these modifications may cause some toxicity. Therefore when designing nucleic acid molecules the amount of these internucleotide linkages should be minimized. The reduction in the concentration of these linkages should lower toxicity resulting in increased efficacy and higher specificity of these molecules.

Nucleic acid molecules having chemical modifications which maintain or enhance activity are provided. Such nucleic acid is also generally more resistant to nucleases than unmodified nucleic acid. Thus, in a cell and/or in vivo the activity may not be significantly lowered. Therapeutic nucleic acid molecules delivered exogenously must optimally be stable within cells until translation of the target RNA has been inhibited long enough to reduce the levels of the undesirable protein. This period of time varies between hours to days depending upon the disease state. Clearly, nucleic acid molecules must be resistant to nucleases in order to function as effective intracellular therapeutic agents. Improvements in the chemical synthesis of RNA and DNA (Wincott et al., 1995 *Nucleic Acids Res.* 23, 2677; Caruthers et al., 1992, *Methods in Enzymology* 211, 3-19 (incorporated by reference herein) have expanded the ability to modify nucleic acid molecules by introducing nucleotide modifications to enhance their nuclease stability as described above.

Use of these the nucleic acid-based molecules of the invention will lead to better treatment of disease progression by affording the possibility of combination therapies (e.g., multiple antisense or enzymatic nucleic acid molecules targeted to different genes, nucleic acid molecules coupled with known small molecule inhibitors, or intermittent treatment with combinations of molecules (including different motifs) and/or other chemical or biological molecules). The treatment of patients with nucleic acid molecules may also include combinations of different types of nucleic acid molecules.

Therapeutic nucleic acid molecules (e.g., enzymatic nucleic acid molecules and antisense nucleic acid molecules) delivered exogenously must optimally be stable within cells until translation of the target RNA has been inhibited long enough to reduce the levels of the undesirable protein. This period of time varies between hours to days depending upon the disease state. Clearly, these nucleic acid molecules must be resistant to nucleases in order to function as effective intracellular therapeutic agents. Improvements in the chemical synthesis of nucleic acid molecules described in the instant invention and in the art have expanded the ability to modify nucleic acid molecules by introducing nucleotide modifications to enhance their nuclease stability as described above.

By "enhanced enzymatic activity" is meant to include activity measured in cells and/or in vivo where the activity is a reflection of both catalytic activity and ribozyme stability. In this invention, the product of these properties is increased or not significantly (less than 10-fold) decreased in vivo compared to an all RNA ribozyme or all DNA enzyme.

In yet another preferred embodiment, nucleic acid catalysts having chemical modifications which maintain or enhance enzymatic activity are provided. Such nucleic acid is also generally more resistant to nucleases than unmodified nucleic acid. Thus, in a cell and/or in vivo the activity may not be significantly lowered. As exemplified herein such nucleic acid molecules are useful in a cell and/or in vivo even if activity over all is reduced 10 fold (see for example Burgin et al., 1996, *Biochemistry*, 35, 14090). Such nucleic acids herein are said to "maintain" the activity of an all RNA nucleic acid molecule, such as a ribozyme or siRNA.

In another aspect the nucleic acid molecules comprise a 5' and/or a 3'-cap structure.

By "cap structure" is meant chemical modifications, which have been incorporated at either terminus of the oligonucleotide (see, for example, Wincott et al., WO 97/26270, incorporated by reference herein). These terminal modifications protect the nucleic acid molecule from exonuclease degradation, and may help in delivery and/or localization within a cell. The cap may be present at the 5'-terminus (5'-cap) or at the 3'-terminus (3'-cap) or may be present on both termini. In non-limiting examples the 5'-cap is selected from the group comprising inverted abasic residue (moiety), 4',5'-methylene nucleotide; 1-(beta-D-erythrofuranosyl) nucleotide, 4'-thio nucleotide, carbocyclic nucleotide; 1,5-anhydrohexitol nucleotide; L-nucleotides; alpha-nucleotides; modified base nucleotide; phosphorodithioate linkage; threo-pentofuranosyl nucleotide; acyclic 3',4'-seco nucleotide; acyclic 3,4-dihydroxybutyl nucleotide; acyclic 3,5-dihydroxypentyl nucleotide, 3'-3'-inverted nucleotide moiety; 3'-3'-inverted abasic moiety; 3'-2'-inverted nucleotide moiety; 3'-2'-inverted abasic moiety; 1,4-butanediol phosphate; 3'-phosphoramidate; hexylphosphate; aminohexyl phosphate; 3'-phosphate; 3'-phosphorothioate; phosphorodithioate; or bridging or non-bridging methylphosphonate moiety (for more details see Wincott et al., International PCT publication No. WO 97/26270, incorporated by reference herein).

In yet another preferred embodiment, the 3'-cap is selected from a group comprising, 4',5'-methylene nucleotide; 1-(beta-D-erythrofuranosyl) nucleotide; 4'-thio nucleotide, carbocyclic nucleotide; 5'-amino-alkyl phosphate; 1,3-diamino-2-propyl phosphate, 3-aminopropyl phosphate; 6-aminohexyl phosphate; 1,2-aminododecyl phosphate; hydroxypropyl phosphate; 1,5-anhydrohexitol nucleotide; L-nucleotide; alpha-nucleotide; modified base nucleotide; phosphorodithioate; threo-pentofuranosyl nucleotide; acyclic 3',4'-seco nucleotide; 3,4-dihydroxybutyl nucleotide; 3,5-dihydroxypentyl nucleotide, 5'-5'-inverted nucleotide moiety; 5'-5'-inverted abasic moiety; 5'-phosphoramidate; 5'-phosphorothioate; 1,4-butanediol phosphate; 5'-amino; bridging and/or non-bridging 5'-phosphoramidate, phosphorothioate and/or phosphorodithioate, bridging or non bridging methylphosphonate and 5'-mercapto moieties (for more details, see Beaucage and Iyer, 1993, *Tetrahedron* 49, 1925; incorporated by reference herein).

By the term "non-nucleotide" is meant any group or compound which can be incorporated into a nucleic acid chain in the place of one or more nucleotide units, including either sugar and/or phosphate substitutions, and allows the remaining bases to exhibit their enzymatic activity. The group or compound is abasic in that it does not contain a commonly recognized nucleotide base, such as adenosine, guanine, cytosine, uracil or thymine.

An "alkyl" group refers to a saturated aliphatic hydrocarbon, including straight-chain, branched-chain, and cyclic alkyl groups. Preferably, the alkyl group has 1 to 12 carbons. More preferably it is a lower alkyl of from 1 to 7 carbons, more preferably 1 to 4 carbons. The alkyl group may be substituted or unsubstituted. When substituted the substituted group(s) is preferably, hydroxyl, cyano, alkoxy, =O, =S, $NO_2$ or $N(CH_3)_2$, amino, or SH. The term also includes alkenyl groups which are unsaturated hydrocarbon groups containing at least one carbon-carbon double bond, including straight-chain, branched-chain, and cyclic groups. Preferably, the alkenyl group has 1 to 12 carbons. More preferably it is a lower alkenyl of from 1 to 7 carbons, more preferably 1 to 4 carbons. The alkenyl group may be substituted or unsubstituted. When substituted the substituted group(s) is preferably, hydroxyl, cyano, alkoxy, =O, =S, $NO_2$, halogen, $N(CH_3)_2$, amino, or SH. The term "alkyl" also includes alkynyl groups which have an unsaturated hydrocarbon group containing at least one carbon-carbon triple bond, including straight-chain, branched-chain, and cyclic groups. Preferably, the alkynyl group has 1 to 12 carbons. More preferably it is a lower alkynyl of from 1 to 7 carbons, more preferably 1 to 4 carbons. The alkynyl group may be substituted or unsubstituted. When substituted the substituted group(s) is preferably, hydroxyl, cyano, alkoxy, =O, =S, $NO_2$ or $N(CH_3)_2$, amino or SH.

Such alkyl groups may also include aryl, alkylaryl, carbocyclic aryl, heterocyclic aryl, amide and ester groups. An "aryl" group refers to an aromatic group which has at least one ring having a conjugated π electron system and includes carbocyclic aryl, heterocyclic aryl and biaryl groups, all of which may be optionally substituted. The preferred substituent(s) of aryl groups are halogen, trihalomethyl, hydroxyl, SH, OH, cyano, alkoxy, alkyl, alkenyl, alkynyl, and amino groups. An "alkylaryl" group refers to an alkyl group (as described above) covalently joined to an aryl group (as described above). Carbocyclic aryl groups are groups wherein the ring atoms on the aromatic ring are all carbon atoms. The carbon atoms are optionally substituted. Heterocyclic aryl groups are groups having from 1 to 3 heteroatoms as ring atoms in the aromatic ring and the remainder of the ring atoms are carbon atoms. Suitable heteroatoms include oxygen, sulfur, and nitrogen, and include furanyl, thienyl, pyridyl, pyrrolyl, N-lower alkyl pyrrolo, pyrimidyl, pyrazinyl, imidazolyl and the like, all optionally substituted. An "amide" refers to an —C(O)—NH—R, where R is either alkyl, aryl, alkylaryl or hydrogen. An "ester" refers to an —C(O)—OR', where R is either alkyl, aryl, alkylaryl or hydrogen.

By "nucleotide" as used herein is as recognized in the art to include natural bases (standard), and modified bases well known in the art. Such bases are generally located at the 1' position of a nucleotide sugar moiety. Nucleotides generally comprise a base, sugar and a phosphate group. The nucleotides can be unmodified or modified at the sugar, phosphate and/or base moiety, (also referred to interchangeably as nucleotide analogs, chemically modified nucleotides, modified nucleotides, non-natural nucleotides, non-standard nucleotides and other; see for example, Usman and McSwiggen, supra; Eckstein et al., International PCT Publication No. WO 92/07065; Usman et al., International PCT Publication No. WO 93/15187; Uhlman & Peyman, supra all are hereby incorporated by reference herein). There are several examples of modified nucleic acid bases known in the art as summarized by Limbach et al., 1994, *Nucleic Acids Res.* 22, 2183. Some of the non-limiting examples of base modifications that can be introduced into nucleic acid molecules include, inosine, purine, pyridin-4-one, pyridin-2-one, phenyl, pseudouracil, 2,4,6-trimethoxy benzene, 3-methyl uracil, dihydrouridine, naphthyl, aminophenyl, 5-alkylcytidines (e.g., 5-methylcytidine), 5-alkyluridines (e.g., ribothymidine), 5-halouridine (e.g., 5-bromouridine) or 6-azapyrimidines or 6-alkylpyrimidines (e.g. 6-methyluridine), propyne, and others (Burgin et al., 1996, *Biochemistry*, 35, 14090; Uhlman & Peyman, supra). By "modified bases" in this aspect is meant nucleotide bases other than adenine, guanine, cytosine and uracil at 1' position or their equivalents; such bases may be used at any position, for example, within the catalytic core of an enzymatic nucleic acid molecule and/or in the substrate-binding regions of the nucleic acid molecule.

In a preferred embodiment, the invention features modified ribozymes with phosphate backbone modifications comprising one or more phosphorothioate, phosphorodithioate, methylphosphonate, morpholino, amidate carbamate, carboxymethyl, acetamidate, polyamide, sulfonate, sulfonamide, sulfamate, formacetal, thioformacetal, and/or alkylsilyl, substitutions. For a review of oligonucleotide backbone modifications see Hunziker and Leumann, 1995, *Nucleic Acid Analogues: Synthesis and Properties*, in *Modern Synthetic Methods*, VCH, 331-417, and Mesmaeker et al., 1994, *Novel Backbone Replacements for Oligonucleotides*, in *Car-* bohydrate Modifications in Antisense Research, ACS, 24-39. These references are hereby incorporated by reference herein.

By "abasic" is meant sugar moieties lacking a base or having other chemical groups in place of a base at the 1' position, (for more details, see Wincott et al., International PCT publication No. WO 97/26270).

By "modified nucleoside" or "chemically modified" is meant any nucleotide which contains a modification in the chemical structure of an unmodified or naturally occurring nucleotide base, sugar and/or phosphate.

In connection with 2'-modified nucleotides as described for the present invention, by "amino" is meant 2'-$NH_2$ or 2'-O—$NH_2$, which may be modified or unmodified. Such modified groups are described, for example, in Eckstein et al., U.S. Pat. No. 5,672,695 and Matulic-Adamic et al., WO 98/28317, respectively, which are both incorporated by reference herein in their entireties.

Various modifications to nucleic acid (e.g., antisense and ribozyme) structure can be made to enhance the utility of these molecules. Such modifications will enhance shelf-life, half-life in vitro, stability, and ease of introduction of such oligonucleotides to the target site, e.g., to enhance penetration of cellular membranes, and confer the ability to recognize and bind to targeted cells.

Use of these molecules will lead to better treatment of the disease progression by affording the possibility of combination therapies (e.g., multiple ribozymes targeted to different genes, ribozymes coupled with known small molecule inhibitors, or intermittent treatment with combinations of ribozymes (including different ribozyme motifs) and/or other chemical or biological molecules). The treatment of patients with nucleic acid molecules may also include combinations of different types of nucleic acid molecules. Therapies may be devised which include a mixture of ribozymes (including different ribozyme motifs), antisense and/or 2-5A chimera molecules to one or more targets to alleviate symptoms of a disease.

Synthesis and Purification of Oligonucleotides Comprising One or More Ribonucleotide Synthesis of nucleic acids greater than 100 nucleotides in length is difficult using automated methods, and the therapeutic cost of such molecules is prohibitive. In this invention, small nucleic acid motifs "small" refers to nucleic acid motifs no more than 100 nucleotides in length, preferably no more than 80 nucleotides in length, and most preferably no more than 50 nucleotides in length; (e.g., individual siNA oligonucleotide sequences or siNA sequences synthesized in tandem) are preferably used for exogenous delivery. The simple structure of these molecules increases the ability of the nucleic acid to invade targeted regions of protein and/or RNA structure. Exemplary molecules of the instant invention are chemically synthesized, and others can similarly be synthesized.

Oligonucleotides (e.g., certain modified oligonucleotides or portions of oligonucleotides lacking ribonucleotides) are synthesized using protocols known in the art, for example as described in Caruthers et al., 1992, Methods in Enzymology 211, 3-19, Thompson et al., International PCT Publication No. WO 99/54459, Wincott et al., 1995, Nucleic Acids Res. 23, 2677-2684, Wincott et al., 1997, Methods Mol. Bio., 74, 59, Brennan et al., 1998, Biotechnol Bioeng., 61, 33-45, and Brennan, U.S. Pat. No. 6,001,311. All of these references are incorporated herein by reference. The synthesis of oligonucleotides makes use of common nucleic acid protecting and coupling groups, such as dimethoxytrityl at the 5'-end, and phosphoramidites at the 3'-end. In a non-limiting example, small scale syntheses are conducted on a 394 Applied Biosystems, Inc. synthesizer using a 0.2 µmol scale protocol with a 2.5 minute coupling step for 2'-O-methylated nucleotides and a 45 second coupling step for 2'-deoxy nucleotides or 2'-deoxy-2'-fluoro nucleotides. Table I outlines the amounts and the contact times of the reagents used in the synthesis cycle. Alternatively, syntheses at the 0.2 µmol scale can be performed on a 96-well plate synthesizer, such as the instrument produced by Protogene (Palo Alto, Calif.) with minimal modification to the cycle. A 33-fold excess (60 µL of 0.11 M=6.6 µmol) of 2'-O-methyl phosphoramidite and a 105-fold excess of S-ethyl tetrazole (60 µL of 0.25 M=15 µmol) can be used in each coupling cycle of 2'-O-methyl residues relative to polymer-bound 5'-hydroxyl. A 22-fold excess (40 µL of 0.11 M=4.4 µmol) of deoxy phosphoramidite and a 70-fold excess of S-ethyl tetrazole (40 µL of 0.25 M=10 µmol) can be used in each coupling cycle of deoxy residues relative to polymer-bound 5'-hydroxyl. Average coupling yields on the 394 Applied Biosystems, Inc. synthesizer, determined by colorimetric quantitation of the trityl fractions, are typically 97.5-99%. Other oligonucleotide synthesis reagents for the 394 Applied Biosystems, Inc. synthesizer include the following: detritylation solution is 3% TCA in methylene chloride (ABI); capping is performed with 16% N-methyl imidazole in THF (ABI) and 10% acetic anhydride/10% 2,6-lutidine in THF (ABI); and oxidation solution is 16.9 mM $I_2$, 49 mM pyridine, 9% water in THF (PERSEPTIVE™). Burdick & Jackson Synthesis Grade acetonitrile is used directly from the reagent bottle. S-Ethyltetrazole solution (0.25 M in acetonitrile) is made up from the solid obtained from American International Chemical, Inc. Alternately, for the introduction of phosphorothioate linkages, Beaucage reagent (3H-1,2-Benzodithiol-3-one 1,1-dioxide, 0.05 M in acetonitrile) is used.

Deprotection of the DNA-based oligonucleotides is performed as follows: the polymer-bound trityl-on oligoribonucleotide is transferred to a 4 mL glass screw top vial and suspended in a solution of 40% aqueous methylamine (1 mL) at 65° C. for 10 minutes. After cooling to −20° C., the supernatant is removed from the polymer support. The support is washed three times with 1.0 mL of EtOH:MeCN:H2O/3:1:1, vortexed and the supernatant is then added to the first supernatant. The combined supernatants, containing the oligoribonucleotide, are dried to a white powder.

The method of synthesis used for RNA including certain siNA molecules of the invention follows the procedure as described in Usman et al., 1987, J. Am. Chem. Soc., 109, 7845; Scaringe et al., 1990, Nucleic Acids Res., 18, 5433; and Wincott et al., 1995, Nucleic Acids Res. 23, 2677-2684 Wincott et al., 1997, Methods Mol. Bio., 74, 59, and makes use of common nucleic acid protecting and coupling groups, such as dimethoxytrityl at the 5'-end, and phosphoramidites at the 3'-end. In a non-limiting example, small scale syntheses are conducted on a 394 Applied Biosystems, Inc. synthesizer using a 0.2 µmol scale protocol with a 7.5 minute coupling step for alkylsilyl protected nucleotides and a 2.5 minute coupling step for 2'-O-methylated nucleotides. Table I outlines the amounts and the contact times of the reagents used in the synthesis cycle. Alternatively, syntheses at the 0.2 µmol scale can be done on a 96-well plate synthesizer, such as the instrument produced by Protogene (Palo Alto, Calif.) with minimal modification to the cycle. A 33-fold excess (60 µL of 0.11 M=6.6 µmol) of 2'-O-methyl phosphoramidite and a 75-fold excess of S-ethyl tetrazole (60 µL of 0.25 M=15 µmol) can be used in each coupling cycle of 2'-O-methyl residues relative to polymer-bound 5'-hydroxyl. A 66-fold excess (120 μL of 0.11 M=13.2 μmol) of alkylsilyl (ribo) protected phosphoramidite and a 150-fold excess of S-ethyl tetrazole (120 μL of 0.25 M=30 μmol) can be used in each coupling cycle of ribo residues relative to polymer-bound 5'-hydroxyl. Average coupling yields on the 394 Applied Biosystems, Inc. synthesizer, determined by colorimetric quantitation of the trityl fractions, are typically 97.5-99%. Other oligonucleotide synthesis reagents for the 394 Applied Biosystems, Inc. synthesizer include the following: detritylation solution is 3% TCA in methylene chloride (ABI); capping is performed with 16% N-methyl imidazole in THF (ABI) and 10% acetic anhydride/10% 2,6-lutidine in THF (ABI); oxidation solution is 16.9 mM $I_2$, 49 mM pyridine, 9% water in THF (PERSEPTIVE™). Burdick & Jackson Synthesis Grade acetonitrile is used directly from the reagent bottle. S-Ethyltetrazole solution (0.25 M in acetonitrile) is made up from the solid obtained from American International Chemical, Inc. Alternately, for the introduction of phosphorothioate linkages, Beaucage reagent (3H-1,2-Benzodithiol-3-one 1,1-dioxide 0.05 M in acetonitrile) is used.

Deprotection of the oligonucleotide comprising one or more ribonucleotides is performed according to the present invention. Oligonucleotides are purified according to the present invention, and/or by gel electrophoresis using general methods or are purified by high pressure liquid chromatography (HPLC; See Stinchcomb et al., International PCT Publication No. WO 95/23225, the totality of which is hereby incorporated herein by reference) and are resuspended in water. For purification of the trityl-on oligomers, the quenched $NH_4HCO_3$ solution is loaded onto a C-18 containing cartridge that had been prewashed with acetonitrile followed by 50 mM TEAA. After washing the loaded cartridge with water, the RNA is detritylated with 0.5% TFA for 13 minutes. The cartridge is then washed again with water, salt exchanged with 1 M NaCl and washed with water again. The oligonucleotide is then eluted with 30% acetonitrile.

The average stepwise coupling yields are typically >98% (Wincott et al., 1995 *Nucleic Acids Res.* 23, 2677-2684). Those of ordinary skill in the art will recognize that the scale of synthesis can be adapted to be larger or smaller than the example described above including but not limited to 96-well format.

Alternatively, the nucleic acid molecules of the present invention can be synthesized separately and joined together post-synthetically, for example, by ligation (Moore et al., 1992, *Science* 256, 9923; Draper et al., International PCT publication No. WO 93/23569; Shabarova et al., 1991, *Nucleic Acids Research* 19, 4247; Bellon et al., 1997, *Nucleosides & Nucleotides*, 16, 951; Bellon et al., 1997, *Bioconjugate Chem.* 8, 204), or by hybridization following synthesis and/or deprotection.

The nucleic acid molecules (e.g. siNA molecules) of the invention can also be synthesized via a tandem synthesis methodology, wherein both siNA strands are synthesized as a single contiguous oligonucleotide fragment or strand separated by a cleavable linker which is subsequently cleaved to provide separate siNA fragments or strands that hybridize and permit purification of the siNA duplex (see McSwiggen et al., U.S. Ser. No. (10/444,853), filed May 23, 2003). The linker can be a polynucleotide linker or a non-nucleotide linker. The tandem synthesis of siNA as described herein can be readily adapted to both multiwell/multiplate synthesis platforms such as 96 well or similarly larger multi-well platforms. The tandem synthesis of siNA as described herein can also be readily adapted to large scale synthesis platforms employing batch reactors, synthesis columns and the like.

A nucleic acid molecule (e.g. siNA molecule) can also be assembled from two distinct nucleic acid strands or fragments wherein one fragment includes the sense region and the second fragment includes the antisense region of the RNA molecule.

The nucleic acid molecules of the present invention can be modified extensively to enhance stability by modification with nuclease resistant groups, for example, 2'-amino, 2'-C-allyl, 2'-fluoro, 2'-O-methyl, 2'-H (for a review see Usman and Cedergren, 1992, *TIBS* 17, 34; Usman et al., 1994, *Nucleic Acids Symp. Ser.* 31, 163). siNA constructs can be purified by gel electrophoresis using general methods or can be purified by high pressure liquid chromatography (HPLC; see Wincott et al., supra, the totality of which is hereby incorporated herein by reference) and re-suspended in water.

Deprotection of Oligonucleotides Comprising One or More Ribonucleotides

For large scale and high throughput chemical synthesis of oligoribonucleotides, it is important that the two main steps involved in the deprotection of oligoribonucleotides (i.e. basic treatment to remove amino protecting groups and phosphate protecting groups and fluoride treatment to remove the 2'-OH alkylsilyl protecting groups such as the t-butyldimethylsilyl group) are condensed.

Stinchcomb et al., supra describe a time-efficient (approximately 2 hours) one-pot deprotection protocol based on anhydrous methylamine and triethylamine trihydrogen fluoride. Since it has been reported that water contamination during fluoride treatment may be detrimental to the efficiency of the desilylation reaction (Hogrefe et al, 1993, *Nucleic Acids Res.*, 21, 4739-4741), and since the use of aqueous methylamine in combination with TEA.3HF results in ribonucleotide degradation (see Example 3), it has previously been thought necessary to use an anhydrous solution of base such as 33% methylamine in absolute ethanol followed by neat triethylamine trihydrofluoride to effectively deprotect oligoribonucleotides in a one-pot fashion. However, these conditions have proven less than stellar for the complete deprotection of 2'-N-phthaloyl protecting groups, as are used to protect the 2'-amino function of 2'-deoxy-2'-amino nucleoside containing nucleic acid molecules since incomplete deprotection products result (see FIG. 2, compound B). Attempts to force the anhydrous deprotection reaction conditions with longer times and/or higher temperatures for the complete removal of phthaloyl groups results in marked degradation of the ribonucleotide species. Therefore, applicant investigated the use of aqueous methylamine in conjunction with TEA.3HF and DMSO as a one pot method for oligonucleotide deprotection. This method, surprisingly, does not cause the presumed alkaline hydrolysis of ribonucleotide linkages when used in the presence of DMSO. Application of the method without DMSO results in lower yields of full length nucleic acid, presumably from alkaline hydrolysis of ribonucleotide linkages (see Example 3). The one pot aqueous method described herein provides a significantly shorter time for oligonucleotide deprotection and provides material with increased yield and purity when compared to existing two pot aqueous and one pot anhydrous methods.

EXAMPLES

The following are non-limiting examples showing the deprotection of oligonucleotides.

Example 1

Small Scale Deprotection of an Oligonucleotide Comprising One or More Ribonucleotides with 2'-O-TBDMS/N-phthaloyl Protection Using a One-Pot Anhydrous Deprotection Method A ribozyme sequence (Table II) (200 μmole) containing two N-phthaloyl protected 2'-amino nucleosides was synthesized as described herein, on CPG support with a Pharmacia OPII synthesizer. After the synthesis, the support was dried for 15 to 30 min. Approximately 20 mg of the support was transferred to a 5 ml screw capped vial. A 1:1 mixture of 33% methylamine/ethanol (800 μl) and dry DMSO (800 μl) was added to the support and the mixture was heated at 65° C. using a heating block for 15 min. The solution was cooled to rt and then filtered through a 0.5 micron filter into another 5 ml screw capped vial. TEA.3HF (600 μl) was added to the reaction mixture followed by heating at 65° C. for 15 min. The mixture was then cooled and quenched with 50 mM NaOAc (2 ml). The corresponding deprotected, purified full length oligonucleotide was analyzed by Capillary Gel Electrophoresis and ES Mass Spec. The mass spectrum revealed three peaks with masses corresponding to the fully deprotected oligonucleotide, the oligonucleotide with one partially cleaved phthaloyl group intact, and the oligonucleotide with two partially cleaved phthaloyl groups intact (FIG. 3A). The CGE chromatograph indicated a single broad peak (FIG. 4A). A similar approach can be utilized to deprotect other oligonucleotides, such as siRNA, antisense, and aptamer oligonucleotides.

Example 2

Small Scale Deprotection of an Oligonucleotide Comprising One or More Ribonucleotides with 2'-O-TBDMS/N-phthaloyl Protection Using a One-Pot Aqueous Deprotection Method A ribozyme sequence (Table II) (200 μmole) was synthesized as described herein on CPG support with a Pharmacia OPII synthesizer. After the synthesis, the support was dried for 15 to 30 min. Approximately 20 mg of the support was transferred to a 5 ml screw capped vial and the support was heated with aqueous methylamine (1 ml) at 65° C. using a heating block for 15 min. The solution was cooled to rt and then filtered through a 0.5 micron filter into another 5 ml screw capped vial. DMSO (1.6 ml) and TEA.3HF (600 μl) were added to the reaction mixture followed by heating at 65° C. for 15 min. The mixture was then cooled and quenched with 50 mM NaOAc (2 ml). The corresponding deprotected, purified full-length oligonucleotide was analyzed by Capillary Gel Electrophoresis and ES Mass Spec. The mass spectrum revealed one peak with a mass corresponding to the fully deprotected oligonucleotide (FIG. 3B). The CGE chromatograph indicated a single narrow peak (FIG. 4B). A similar approach can be utilized to deprotect other oligonucleotides, such as siRNA, antisense and aptamer oligonucleotides containing ribonucleotides and/or having chemical modifications. Additionally, deprotection conditions can be modified to provide the best possible yield and purity of the oligonucleotide constructs. For example, applicant has observed that oligonucleotides comprising 2'-deoxy-2'-fluoro nucleotides can degrade under inappropriate deprotection conditions. Such oligonucleotides are deprotected using aqueous methylamine at about 35° C. for 30 minutes. If the 2'-deoxy-2'-fluoro containing oligonucleotide also comprises ribonucleotides, after deprotection with aqueous methylamine at about 35° C. for 30 minutes, TEA-HF is added and the reaction maintained at about 65° C. for an additional 15 minutes.

Example 3

Small Scale Deprotection of an Oligonucleotide Comprising One or More Ribonucleotides with 2'-O-TBDMS/N-phthaloyl Protection Using a One-Pot Aqueous Deprotection Method Without DMSO A ribozyme sequence (Table II) (200 μmole) was synthesized as described herein on CPG support with a Pharmacia OPII synthesizer. After the synthesis, the support was dried for 15 to 30 min. Approximately 20 mg of the support was transferred to a 5 ml screw capped vial and the support was heated with aqueous methylamine (1 ml) at 65° C. using a heating block for 15 min. The solution was cooled to rt and then filtered through a 0.5 micron filter into another 5 ml screw capped vial. TEA.3HF (600 μl) was added to the reaction mixture followed by heating at 65° C. for 15 min. The mixture was then cooled and quenched with 50 mM NaOAc (2 ml). The corresponding deprotected, purified full-length oligonucleotide was analyzed by ion exchange HPLC. The HPLC trace revealed significant degradation corresponding to cleavage of ribonucleotide linkages within the oligonucleotide when compared to material from example 2 in which DMSO was used in the deprotection. A similar approach can be utilized to deprotect other oligonucleotides, such as siRNA, antisense and aptamer oligonucleotides containing ribonucleotides and/or having chemical modifications. Additionally, deprotection conditions can be modified to provide the best possible yield and purity of the oligonucleotide constructs. For example, applicant has observed that oligonucleotides comprising 2'-deoxy-2'-fluoro nucleotides can degrade under inappropriate deprotection conditions. Such oligonucleotides are deprotected using aqueous methylamine at about 35° C. for 30 minutes. If the 2'-deoxy-2'-fluoro containing oligonucleotide also comprises ribonucleotides, after deprotection with aqueous methylamine at about 35° C. for 30 minutes, TEA-HF is added and the reaction maintained at about 65° C. for an additional 15 minutes.

Example 4

Large Scale Deprotection of an Oligonucleotide Comprising One or More Ribonucleotides with 2'-O-TBDMS Protection Using a One-Pot Anhydrous Deprotection Method A ribozyme sequence (Table II) (200 μmole) was synthesized as described herein on CPG support with a Pharmacia OPII synthesizer. After the synthesis, the support was dried for 15 to 30 min and transferred to a 500 ml Schott bottle. A 1:1 mixture of 33% methylamine/ethanol (75 ml) and dry DMSO (75 ml) was added to the support and the mixture was heated at 35° C. in an incubated shaker for 4 h. The solution was cooled to rt (15 min) and then filtered through a sintered glass funnel. The support was washed with DMSO (4×15 ml) and the combined filtrate was cooled in an ice bath for 30 min. TEA.3HF (30 ml) was added to the reaction mixture followed by heating at 65° C. for 1 h. The mixture was then cooled at −78° C. for 30 min and quenched with 50 mM NaOAc (200

Example 5

Large Scale Deprotection of an Oligonucleotide Comprising One or More Ribonucleotides with 2'-O-TBDMS Protection Using a One-Pot Aqueous Deprotection Method

A ribozyme sequence (Table II) (200 µmole) was synthesized described herein on CPG support with a Pharmacia OPII synthesizer. After the synthesis, the support was dried for 15 to 30 min and transferred to a 250 ml Schott bottle. 40% Aqueous methylamine (75 ml) was added to the support and the mixture was heated at 35° C. in an incubated shaker for 1 h. The solution was cooled to rt (15 min) and then filtered through a sintered glass funnel. The support was washed with DMSO (4×18.75 ml) and the combined filtrate was cooled in an ice bath for 30 min. TEA.3HF (45 ml) was added to the reaction mixture followed by heating at 65° C. for 1 h. The mixture was then cooled at −78° C. for 30 min and quenched with 50 mM NaOAc (195 ml). A similar approach can be utilized to deprotect other oligonucleotides, such as siRNA, antisense and aptamer oligonucleotides containing ribonucleotides and/or having chemical modifications. Additionally, deprotection conditions can be modified to provide the best possible yield and purity of the oligonucleotide constructs. For example, applicant has observed that oligonucleotides comprising 2'-deoxy-2'-fluoro nucleotides can degrade under inappropriate deprotection conditions. Such oligonucleotides are deprotected using aqueous methylamine at about 35° C. for 30 minutes. If the 2'-deoxy-2'-fluoro containing oligonucleotide also comprises ribonucleotides, after deprotection with aqueous methylamine at about 35° C. for 30 minutes, TEA-HF is added and the reaction maintained at about 65° C. for an additional 15 minutes.

Example 6

Large Scale Deprotection of an Oligonucleotide Comprising One or More Ribonucleotides with 2'-O-TBDMS/N-phthaloyl Protection Using a One-Pot Aqueous Deprotection Method

A ribozyme sequence (Table II) (200 µmole) was synthesized as described herein on CPG support with a Pharmacia OPII synthesizer. After the synthesis, the support was dried for 15 to 30 min and transferred to a 250 ml Schott bottle. 40% Aqueous methylamine (75 ml) was added to the support and the mixture was heated at 65° C. in an incubated shaker for 1 h. The solution was cooled to rt (15 min) and then filtered through a sintered glass funnel. The support was washed with DMSO (4×18.75 ml) and the combined filtrate was cooled at −78° C. for 30 min. TEA.3HF (45 ml) was added to the reaction mixture followed by heating at 65° C. for 1 h. The mixture was then cooled in an ice bath for 30 min and quenched with 50 mM NaOAc (195 ml). A similar approach can be utilized to deprotect other oligonucleotides, such as siRNA, antisense and aptamer oligonucleotides containing ribonucleotides and/or having chemical modifications. Additionally, deprotection conditions can be modified to provide the best possible yield and purity of the oligonucleotide constructs. For example, applicant has observed that oligonucleotides comprising 2'-deoxy-2'-fluoro nucleotides can degrade under inappropriate deprotection conditions. Such oligonucleotides are deprotected using aqueous methylamine at about 35° C. for 30 minutes. If the 2'-deoxy-2'-fluoro containing oligonucleotide also comprises ribonucleotides, after deprotection with aqueous methylamine at about 35° C. for 30 minutes, TEA-HF is added and the reaction maintained at about 65° C. for an additional 15 minutes.

Example 7

Large Scale Ion Exchange Purification of an Oligonucleotide Comprising One or More Ribonucleotides

Oligonucleotide comprising one or more ribonucleotides (e.g., siRNA, antisense, or aptamer oligonucleotides) are purified by ion exchange chromatography following deprotection. The ion-exchange purification process can be performed on both Pharmacia Source Q15 and Biorad Macroprep 25Q type media. The buffer used for equilibration of the purification media is either 0-20% ethanol (200 proof USP grade) or acetonitrile, in 20 mmolar sodium phosphate and 0.1 M NaCl. The same buffer can be used for loading the nucleic acid molecule onto the purification media, or alternatively, water can be used. The crude oligonucleotide material is loaded on the column in concentrations up to 10 mg/mL. Application of a suitable gradient of an elution buffer such as 1.0 M NaCl can be used to isolate fractions. Following purification, the fractions are analyzed for purity by a suitable method (for example UV, HPLC and/or CGE). The pure fractions are pooled and desalting is performed via tangential flow filtration using membranes such as Sartorius or Pall Filtron PES 1 K membranes. The concentrated material is then lyophilized. A similar approach can be used to purify siRNA constructs of the invention, such as single stranded, haipin, and duplex siRNA. For duplex siRNA, each strand is synthesized, deprotected, and purified separately, then hybridized under conditions suitable for duplex formation. In a non-limiting example, siRNA strands are annealed in 100 mM potassium acetate, 30 mM HEPES-KOH at pH 7.4, 2 mM magnesium acetate at 20 µM each strand. The annealing mixture is first heated to 90° C. for 1 minute and then is transferred to 37° C. for 60 minutes. Annealing is confirmed by non-denaturing PAGE. Alternately, duplex siRNA can be synthesized using a tandem synthesis approach as described in Example 8 below.

Example 8

Tandem Synthesis of siRNA Constructs

Exemplary siRNA molecules of the invention are synthesized in tandem using a cleavable linker, for example, a succinyl-based linker. Tandem synthesis as described herein is followed by a one-step purification process that provides RNAi molecules in high yield. This approach is highly amenable to siNA synthesis in support of high throughput RNAi screening, and can be readily adapted to multi-column or multi-well synthesis platforms.

After completing a tandem synthesis of a siNA oligo and its complement in which the 5'-terminal dimethoxytrityl (5'-O-DMT) group remains intact (trityl on synthesis), the oligonucleotides are deprotected as described above, for example as described in Example 2. Following deprotection, the siNA sequence strands are allowed to spontaneously hybridize. This hybridization yields a duplex in which one strand has retained the 5'-O-DMT group while the complementary strand comprises a terminal 5'-hydroxyl. The newly formed duplex behaves as a single molecule during routine solid-phase extraction purification (Trityl-On purification) even though only one molecule has a dimethoxytrityl group. Because the strands form a stable duplex, this dimethoxytrityl group (or an equivalent group, such as other trityl groups or other hydrophobic moieties) is all that is required to purify the pair of oligos, for example, by using a C18 cartridge.

Standard phosphoramidite synthesis chemistry is used up to the point of introducing a tandem linker, such as an inverted deoxy abasic succinate or glyceryl succinate linker (see FIG. 5) or an equivalent cleavable linker. A non-limiting example of linker coupling conditions that can be used includes a hindered base such as diisopropylethylamine (DIPA) and/or DMAP in the presence of an activator reagent such as Bromotripyrrolidinophosphoniumhexafluorophosphate (PyBrOP). After the linker is coupled, standard synthesis chemistry is utilized to complete synthesis of the second sequence leaving the terminal the 5'-O-DMT intact. Following synthesis, the resulting oligonucleotide is deprotected according to the procedures described herein and quenched with a suitable buffer, for example with 50 mM NaOAc or 1.5M $NH_4H_2CO_3$.

Purification of the siRNA duplex can be readily accomplished using solid phase extraction, for example using a Waters C18 SepPak 1 g cartridge conditioned with 1 column volume (CV) of acetonitrile, 2 CV H2O, and 2 CV 50 mM NaOAc. The sample is loaded and then washed with 1 CV H2O or 50 mM NaOAc. Failure sequences are eluted with 1 CV 14% ACN (Aqueous with 50 mM NaOAc and 50 mM NaCl). The column is then washed, for example with 1 CV H2O followed by on-column detritylation, for example by passing 1 CV of 1% aqueous trifluoroacetic acid (TFA) over the column, then adding a second CV of 1% aqueous TFA to the column and allowing to stand for approximately 10 minutes. The remaining TFA solution is removed and the column washed with H2O followed by 1 CV 1M NaCl and additional H2O. The siNA duplex product is then eluted, for example, using 1 CV 20% aqueous CAN.

FIG. 6 provides an example of MALDI-TOF mass spectrometry analysis of a purified siNA construct in which each peak corresponds to the calculated mass of an individual siNA strand of the siNA duplex. The same purified siNA provides three peaks when analyzed by capillary gel electrophoresis (CGE), one peak presumably corresponding to the duplex siNA, and two peaks presumably corresponding to the separate siNA sequence strands. Ion exchange HPLC analysis of the same siNA contract only shows a single peak. Testing of the purified siNA construct using a luciferase reporter assay described below demonstrated the same RNAi activity compared to siNA constructs generated from separately synthesized oligonucleotide sequence strands.

Other Uses

The nucleic acid molecules of this invention (e.g., ribozymes) may be used as therapeutic agents to treat a broad spectrum of diseases and conditions. Ribozymes are RNA molecules having an enzymatic activity which is able to repeatedly cleave other separate RNA molecules in a nucleotide base sequence specific manner. Such enzymatic RNA molecules can be targeted to virtually any RNA transcript, and efficient cleavage achieved in vitro. Kim et al., 1987, *Proc. Nat. Acad. of Sci. USA,* 84, 8788, Hazeloff et al., 1988 *Nature,* 234, 585, Cech, 1988, *JAMA,* 260, 3030, and Jefferies et al., 1989, *Nucleic Acid Research,* 17, 1371. Ribozymes act by first binding to a target RNA. Such binding occurs through the target RNA binding portion of a ribozyme which is held in close proximity to an enzymatic portion of the RNA which acts to cleave the target RNA. Thus, the ribozyme first recognizes and then binds a target RNA through complementary base-pairing, and once bound to the correct site, acts enzymatically to cut the target RNA. Strategic cleavage of such a target RNA will destroy its ability to direct synthesis of an encoded protein. After a ribozyme has bound and cleaved its RNA target it is released from that RNA to search for another target and can repeatedly bind and cleave new targets.

The nucleic acid molecules of the invention may be used as diagnostic tools to examine genetic drift and mutations within diseased cells or to detect the presence of a particular RNA in a cell. The close relationship between ribozyme activity and the structure of the target RNA allows the detection of mutations in any region of the molecule which alters the base-pairing and three-dimensional structure of the target RNA. By using multiple ribozymes described in this invention, one may map nucleotide changes which are important to RNA structure and function in vitro, as well as in cells and tissues. Cleavage of target RNAs with ribozymes may be used to inhibit gene expression and define the role (essentially) of specified gene products in the progression of disease. In this manner, other genetic targets may be defined as important mediators of the disease. These experiments will lead to better treatment of disease progression by affording the possibility of combinational therapies (e.g., multiple ribozymes targeted to different genes, ribozymes coupled with known small molecule inhibitors, or intermittent treatment with combinations of ribozymes and/or other chemical or biological molecules). Other in vitro uses of ribozymes of this invention are well known in the art, and include detection of the presence of mRNAs associated with a RNA-related condition. Such RNA is detected by determining the presence of a cleavage product after treatment with a ribozyme using standard methodology.

In a specific example, ribozymes which can cleave only wild-type or mutant forms of the target RNA are used for the assay. The first ribozyme is used to identify wild-type RNA present in the sample and the second ribozyme will be used to identify mutant RNA in the sample. As reaction controls, synthetic substrates of both wild-type and mutant RNA will be cleaved by both ribozymes to demonstrate the relative ribozyme efficiencies in the reactions and the absence of cleavage of the "non-targeted" RNA species. The cleavage products from the synthetic substrates will also serve to generate size markers for the analysis of wild-type and mutant RNAs in the sample population. Thus, each analysis can require two ribozymes, two substrates and one unknown sample, which will be combined into six reactions. The presence of cleavage products will be determined using an RNAse protection assay so that full-length and cleavage fragments of each RNA can be analyzed in one lane of a polyacrylamide gel. It is not absolutely required to quantify the results to gain insight into the expression of mutant RNAs and putative risk of the desired phenotypic changes in target cells. The expression of mRNA whose protein product is implicated in the development of the phenotype is adequate to establish risk. If probes of comparable specific activity are used for both transcripts, then a qualitative comparison of RNA levels will be adequate and will decrease the cost of the initial diagnosis. Higher mutant form to wild-type ratios will be correlated with higher risk whether RNA levels are compared qualitatively or quantitatively.

All patents and publications mentioned in the specification are indicative of the levels of skill of those skilled in the art to which the invention pertains. All references cited in this disclosure are incorporated by reference to the same extent as if each reference had been incorporated by reference in its entirety individually.

One skilled in the art would readily appreciate that the present invention is well adapted to carry out the objects and obtain the ends and advantages mentioned, as well as those inherent therein. The methods and compositions described herein as presently representative of preferred embodiments are exemplary and are not intended as limitations on the scope of the invention. Changes therein and other uses will occur to those skilled in the art, which are encompassed within the spirit of the invention, are defined by the scope of the claims.

It will be readily apparent to one skilled in the art that varying substitutions and modifications may be made to the invention disclosed herein without departing from the scope and spirit of the invention. Thus, such additional embodiments are within the scope of the present invention and the following claims.

The invention illustratively described herein suitably may be practiced in the absence of any element or elements, limitation or limitations which is not specifically disclosed herein. Thus, for example, in each instance herein any of the terms "comprising", "consisting essentially of", and "consisting of" may be replaced with either of the other two terms. The terms and expressions which have been employed are used as terms of description and not of limitation, and there is no intention that in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments, optional features, modification and variation of the concepts herein disclosed may be resorted to by those skilled in the art, and that such modifications and variations are considered to be within the scope of this invention as defined by the description and the appended claims.

In addition, where features or aspects of the invention are described in terms of Markush groups or other grouping of alternatives, those skilled in the art will recognize that the invention is also thereby described in terms of any individual member or subgroup of members of the Markush group or other group.

Thus, additional embodiments are within the scope of the invention and within the following claims:

Other embodiments are within the following claims.

TABLE II

Nucleic Acid Sequence used in Deprotection Studies

| Sequence | Compound No. | Seq ID No. |
|---|---|---|
| g$_s$c$_s$a$_s$g$_s$ug GccgaaagGCGaGuGaGGuCu agcuca B | 19292 | 1 |

Lower case = 2'-O-methyl
Upper Case = ribonucleotide
C = 2'-deoxy-2'-amino Cytidine
s = phosphorothioate internucleotide linkage
B = inverted deoxy abasic moiety

TABLE III

Non-limiting examples of Stabilization Chemistries for chemically modified siNA constructs

| Chemistry | pyrimidine | Purine | cap | p = S | Strand |
|---|---|---|---|---|---|
| "Stab 00" | Ribo | Ribo | TT at 3'-ends | — | S/AS |
| "Stab 1" | Ribo | Ribo | — | 5 at 5'-end 1 at 3'-end | S/AS |
| "Stab 2" | Ribo | Ribo | — | All linkages | Usually AS |
| "Stab 3" | 2'-fluoro | Ribo | — | 4 at 5'-end 4 at 3'-end | Usually S |

TABLE I

| Reagent | Equivalents | Amount | Wait Time* DNA | Wait Time* 2'-O-methyl | Wait Time* RNA |
|---|---|---|---|---|---|
| A. 2.5 μmol Synthesis Cycle ABI 394 Instrument | | | | | |
| Phosphoramidites | 6.5 | 163 μL | 45 sec | 2.5 min | 7.5 min |
| S-Ethyl Tetrazole | 23.8 | 238 μL | 45 sec | 2.5 min | 7.5 min |
| Acetic Anhydride | 100 | 233 μL | 5 sec | 5 sec | 5 sec |
| N-Methyl Imidazole | 186 | 233 μL | 5 sec | 5 sec | 5 sec |
| TCA | 176 | 2.3 mL | 21 sec | 21 sec | 21 sec |
| Iodine | 11.2 | 1.7 mL | 45 sec | 45 sec | 45 sec |
| Beaucage | 12.9 | 645 μL | 100 sec | 300 sec | 300 sec |
| Acetonitrile | NA | 6.67 mL | NA | NA | NA |
| B. 0.2 μmol Synthesis Cycle ABI 394 Instrument | | | | | |
| Phosphoramidites | 15 | 31 μL | 45 sec | 233 sec | 465 sec |
| S-Ethyl Tetrazole | 38.7 | 31 μL | 45 sec | 233 min | 465 sec |
| Acetic Anhydride | 655 | 124 μL | 5 sec | 5 sec | 5 sec |
| N-Methyl Imidazole | 1245 | 124 μL | 5 sec | 5 sec | 5 sec |
| TCA | 700 | 732 μL | 10 sec | 10 sec | 10 sec |
| Iodine | 20.6 | 244 μL | 15 sec | 15 sec | 15 sec |
| Beaucage | 7.7 | 232 μL | 100 sec | 300 sec | 300 sec |
| Acetonitrile | NA | 2.64 mL | NA | NA | NA |

| Reagent | Equivalents: DNA/2'-O-methyl/Ribo | Amount: DNA/2'-O-methyl/Ribo | Wait Time* DNA | Wait Time* 2'-O-methyl | Wait Time* Ribo |
|---|---|---|---|---|---|
| C. 0.2 μmol Synthesis Cycle 96 well Instrument | | | | | |
| Phosphoramidites | 22/33/66 | 40/60/120 μL | 60 sec | 180 sec | 360 sec |
| S-Ethyl Tetrazole | 70/105/210 | 40/60/120 μL | 60 sec | 180 min | 360 sec |
| Acetic Anhydride | 265/265/265 | 50/50/50 μL | 10 sec | 10 sec | 10 sec |
| N-Methyl Imidazole | 502/502/502 | 50/50/50 μL | 10 sec | 10 sec | 10 sec |
| TCA | 238/475/475 | 250/500/500 μL | 15 sec | 15 sec | 15 sec |
| Iodine | 6.8/6.8/6.8 | 80/80/80 μL | 30 sec | 30 sec | 30 sec |
| Beaucage | 34/51/51 | 80/120/120 μL | 100 sec | 200 sec | 200 sec |
| Acetonitrile | NA | 1150/1150/1150 μL | NA | NA | NA |

*Wait time does not include contact time during delivery.

TABLE III-continued

Non-limiting examples of Stabilization Chemistries for chemically modified siNA constructs

| Chemistry | pyrimidine | Purine | cap | p = S | Strand |
|---|---|---|---|---|---|
| "Stab 4" | 2'-fluoro | Ribo | 5' and 3'-ends | — | Usually S |
| "Stab 5" | 2'-fluoro | Ribo | — | 1 at 3'-end | Usually AS |
| "Stab 6" | 2'-O-Methyl | Ribo | 5' and 3'-ends | — | Usually S |
| "Stab 7" | 2'-fluoro | 2'-deoxy | 5' and 3'-ends | — | Usually S |
| "Stab 8" | 2'-fluoro | 2'-O-Methyl | — | 1 at 3'-end | S/AS |
| "Stab 9" | Ribo | Ribo | 5' and 3'-ends | — | Usually S |
| "Stab 10" | Ribo | Ribo | — | 1 at 3'-end | Usually AS |
| "Stab 11" | 2'-fluoro | 2'-deoxy | — | 1 at 3'-end | Usually AS |
| "Stab 12" | 2'-fluoro | LNA | 5' and 3'-ends | — | Usually S |
| "Stab 13" | 2'-fluoro | LNA | — | 1 at 3'-end | Usually AS |
| "Stab 14" | 2'-fluoro | 2'-deoxy | — | 2 at 5'-end 1 at 3'-end | Usually AS |
| "Stab 15" | 2'-deoxy | 2'-deoxy | — | 2 at 5'-end 1 at 3'-end | Usually AS |
| "Stab 16" | Ribo | 2'-O-Methyl | 5' and 3'-ends | — | Usually S |
| "Stab 17" | 2'-O-Methyl | 2'-O-Methyl | 5' and 3'-ends | — | Usually S |
| "Stab 18" | 2'-fluoro | 2'-O-Methyl | 5' and 3'-ends | — | Usually S |
| "Stab 19" | 2'-fluoro | 2'-O-Methyl | 3'-end | — | S/AS |
| "Stab 20" | 2'-fluoro | 2'-deoxy | 3'-end | — | Usually AS |
| "Stab 21" | 2'-fluoro | Ribo | 3'-end | — | Usually AS |
| "Stab 22" | Ribo | Ribo | 3'-end | — | Usually AS |
| "Stab 23" | 2'-fluoro* | 2'-deoxy* | 5' and 3'-ends | — | Usually S |
| "Stab 24" | 2'-fluoro* | 2'-O-Methyl* | — | 1 at 3'-end | S/AS |
| "Stab 25" | 2'-fluoro* | 2'-O-Methyl* | — | 1 at 3'-end | S/AS |
| "Stab 26" | 2'-fluoro* | 2'-O-Methyl* | — | — | S/AS |
| "Stab 27" | 2'-fluoro* | 2'-O-Methyl* | 3'-end | — | S/AS |
| "Stab 28" | 2'-fluoro* | 2'-O-Methyl* | 3'-end | — | S/AS |
| "Stab 29" | 2'-fluoro* | 2'-O-Methyl* | — | 1 at 3'-end | S/AS |
| "Stab 30" | 2'-fluoro* | 2'-O-Methyl* | — | — | S/AS |
| "Stab 31" | 2'-fluoro* | 2'-O-Methyl* | 3'-end | — | S/AS |
| "Stab 32" | 2'-fluoro | 2'-O-Methyl | — | — | S/AS |
| "Stab 33" | 2'-fluoro | 2'-deoxy* | 5' and 3'-ends | — | Usually S |
| "Stab 34" | 2'-fluoro | 2'-O-Methyl* | 5' and 3'-ends | — | Usually S |
| "Stab 3F" | 2'-OCF3 | Ribo | — | 4 at 5'-end 4 at 3'-end | Usually S |
| "Stab 4F" | 2'-OCF3 | Ribo | 5' and 3'-ends | — | Usually S |
| "Stab 5F" | 2'-OCF3 | Ribo | — | 1 at 3'-end | Usually AS |
| "Stab 7F" | 2'-OCF3 | 2'-deoxy | 5' and 3'-ends | — | Usually S |
| "Stab 8F" | 2'-OCF3 | 2'-O-Methyl | — | 1 at 3'-end | S/AS |
| "Stab 11F" | 2'-OCF3 | 2'-deoxy | — | 1 at 3'-end | Usually AS |
| "Stab 12F" | 2'-OCF3 | LNA | 5' and 3'-ends | — | Usually S |
| "Stab 13F" | 2'-OCF3 | LNA | — | 1 at 3'-end | Usually AS |
| "Stab 14F" | 2'-OCF3 | 2'-deoxy | — | 2 at 5'-end 1 at 3'-end | Usually AS |
| "Stab 15F" | 2'-OCF3 | 2'-deoxy | — | 2 at 5'-end 1 at 3'-end | Usually AS |
| "Stab 18F" | 2'-OCF3 | 2'-O-Methyl | 5' and 3'-ends | — | Usually S |
| "Stab 19F" | 2'-OCF3 | 2'-O-Methyl | 3'-end | — | S/AS |
| "Stab 20F" | 2'-OCF3 | 2'-deoxy | 3'-end | — | Usually AS |
| "Stab 21F" | 2'-OCF3 | Ribo | 3'-end | — | Usually AS |
| "Stab 23F" | 2'-OCF3* | 2'-deoxy* | 5' and 3'-ends | — | Usually S |
| "Stab 24F" | 2'-OCF3* | 2'-O-Methyl* | — | 1 at 3'-end | S/AS |
| "Stab 25F" | 2'-OCF3* | 2'-O-Methyl* | — | 1 at 3'-end | S/AS |
| "Stab 26F" | 2'-OCF3* | 2'-O-Methyl* | — | — | S/AS |
| "Stab 27F" | 2'-OCF3* | 2'-O-Methyl* | 3'-end | — | S/AS |
| "Stab 28F" | 2'-OCF3* | 2'-O-Methyl* | 3'-end | — | S/AS |
| "Stab 29F" | 2'-OCF3* | 2'-O-Methyl* | — | 1 at 3'-end | S/AS |
| "Stab 30F" | 2'-OCF3* | 2'-O-Methyl* | — | — | S/AS |
| "Stab 31F" | 2'-OCF3* | 2'-O-Methyl* | 3'-end | — | S/AS |
| "Stab 32F" | 2'-OCF3 | 2'-O-Methyl | — | — | S/AS |
| "Stab 33F" | 2'-OCF3 | 2'-deoxy* | 5' and 3'-ends | — | Usually S |
| "Stab 34F" | 2'-OCF3 | 2'-O-Methyl* | 5' and 3'-ends | — | Usually S |

CAP = any terminal cap, see for example FIG. 10.
All Stab 00-34 chemistries can comprise 3'-terminal thymidine (TT) residues
All Stab 00-34 chemistries typically comprise about 21 nucleotides, but can vary as described herein.
S = sense strand
AS = antisense strand
*Stab 23 has a single ribonucleotide adjacent to 3'-CAP
*Stab 24 and Stab 28 have a single ribonucleotide at 5'-terminus
*Stab 25, Stab 26, and Stab 27 have three ribonucleotides at 5'-terminus
*Stab 29, Stab 30, Stab 31, Stab 33, and Stab 34 any purine at first three nucleotide positions from 5'-terminus are ribonucleotides
p = phosphorothioate linkage

What we claim is:

1. A process comprising the steps of:
   a) synthesizing a nucleic acid molecule comprising one or more ribonucleotides, using a method selected from the group consisting of solid phase phosphoramidite, solution phase phosphoramidite, solid phase H-phosphonate, solution phase H-phosphonate, hybrid phase phosphoramidite, and hybrid phase H-phosphonate-based synthetic methods;
   b) contacting said nucleic acid molecule from step (a) with aqueous alkylamine, trialkylamine, or alkylamine and trialkylamine, under conditions suitable for the removal of any 2'-amino protecting groups, exocyclic amino (base) protecting groups and/or phosphate protecting groups, which may be individually present or absent, from said molecule;
   c) contacting reaction mixture having said nucleic acid molecule from step (b) with a polar solvent and trialkylamine.hydrogen fluoride under conditions suitable for the removal of a 2'-OH protecting group;
   d) loading reaction mixture having said nucleic acid molecule from step (c) onto a media selected from the group consisting of Pharmacia Source Q15, Biorad Macroprep 25Q, Pharmacia Q-sepharose, Perceptive POROS HQ, TOSOHAAS Q-5PW-HR, Q-5PW, and super Q-5PW media in a suitable buffer comprising buffers selected from the group consisting of water, 20% ethanol in about 20 mM sodium phosphate and about 0.1 M NaCl and acetonitrile in about 20 mM sodium phosphate and about 0.1 M NaCl;

e) applying a purification gradient using a suitable elution buffer, analyzing the fractions and allowing for the pure fractions to be pooled and desalted.

2. The process of claim 1, wherein said nucleic acid molecule comprising one or more ribonucleotides is a siRNA molecule.

3. The process of claim 2, wherein said siRNA molecule further comprises one or more 2'-deoxy-2'-fluoro nucleotides.

4. The process of claim 1, wherein said aqueous alkylamine is aqueous methylamine.

5. The process of claim 1, wherein said aqueous alkylamine is 40% aqueous methylamine.

6. The process of claim 1, wherein said trialkylamine.trihydrofluoride is triethylamine.trihydrofluoride (TEA.3HF).

7. The process of claim 1, wherein said 2'-OH protecting group comprises the t-butyldimethylsilyl (TBDMSi) protecting group.

8. The process of claim 1, wherein said nucleic acid molecule comprises one or more chemical modifications.

9. A process of purifying a nucleic acid molecule, comprising the steps of:

a) loading said nucleic acid molecule onto a media selected from the group consisting of Pharmacia Source Q15, Biorad Macroprep 25Q, Pharmacia Q-sepharose, Perceptive POROS HQ, TOSOHAAS Q-5PW-HR, Q-5PW, and super Q-5PW media in a loading buffer comprising buffers selected from the group consisting of water, 20% ethanol in about 20 mM sodium phosphate and about 0.1 M NaCl and acetonitrile in about 20 mM sodium phosphate and about 0.1 M NaCl;

b) applying a purification gradient using a suitable elution buffer, analyzing the fractions and allowing for the pure fractions to be pooled and desalted.

10. The process of claim 9, wherein said nucleic acid molecule comprises one or more ribonucleotides.

11. The process of claim 9, wherein said nucleic acid molecule comprises one or more chemical modifications.

12. The process of claims 1 or 9, wherein said nucleic acid molecule is a single stranded nucleic acid molecule.

13. The process of claims 1 or 9, wherein said nucleic acid molecule is a double stranded nucleic acid molecule.

14. The process of claim 13, wherein said double stranded nucleic acid molecule comprises one or more chemical modifications.

15. The process of claim 13, wherein said each strand of the double stranded nucleic acid molecule is of length between 19 and 23 nucleotides.

16. The process of claims 8 or 11, wherein said chemical modification is a sugar modification.

17. The process of claim 16, wherein said sugar modification is a 2'-sugar modification.

18. The process of claims 8 or 11, wherein said chemical modification is a base modification.

19. The process of claims 8 or 11, wherein said chemical modification is a phosphate backbone modification.

20. The process of claim 19, wherein said phosphate backbone modification is phosphorothioate.

21. The process of claims 8 or 11, wherein said chemical modification is a terminal end modification.

22. The process of claim 21, wherein said end modification is at the 5'-end of said nucleic acid molecule.

23. The process of claim 21, wherein said end modification is at the 3'-end of said nucleic acid molecule.

24. The process of claim 21, wherein said end modification is at both the 5'- and 3'-end of said nucleic acid molecule.

* * * * *

UNITED STATES PATENT AND TRADEMARK OFFICE
CERTIFICATE OF CORRECTION

PATENT NO.        : 7,655,790 B2                                       Page 1 of 1
APPLICATION NO.   : 11/036694
DATED             : February 2, 2010
INVENTOR(S)       : Vargeese et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 667 days.

Signed and Sealed this

Twenty-eighth Day of December, 2010

David J. Kappos
*Director of the United States Patent and Trademark Office*